(12) United States Patent
Kim et al.

(10) Patent No.: US 8,906,632 B2
(45) Date of Patent: Dec. 9, 2014

(54) USE OF INHIBITORS OF LEUKOTRIENE B4 RECEPTOR BLT2 FOR TREATING ASTHMA

(75) Inventors: Jae-Hong Kim, Goyang Gyeonggi-Do (KR); Kyung-Jin Cho, Busan (KR); Min-Hyuk Yoo, Seoul (KR)

(73) Assignee: Korea University Research & Business Foundation, Seoul (KR)

( * ) Notice: Subject to any disclaimer, the term of this patent is extended or adjusted under 35 U.S.C. 154(b) by 391 days.

(21) Appl. No.: 13/316,015

(22) Filed: Dec. 9, 2011

(65) Prior Publication Data

US 2012/0164149 A1    Jun. 28, 2012

Related U.S. Application Data

(63) Continuation of application No. 12/450,342, filed as application No. PCT/KR2008/001650 on Mar. 24, 2008, now abandoned.

(60) Provisional application No. 60/896,501, filed on Mar. 23, 2007, provisional application No. 60/896,502, filed on Mar. 23, 2007.

(51) Int. Cl.
*C07K 16/28* (2006.01)
*G01N 33/88* (2006.01)

(52) U.S. Cl.
USPC ...... 435/7.1; 424/130.1; 424/143.1; 435/331; 530/387.9; 530/388.22; 530/391.1

(58) Field of Classification Search
USPC ................. 435/6, 91.1, 91.31, 455, 7.1, 331; 514/1, 2, 44; 530/300, 350, 387.9, 530/388.22; 536/23.1, 24.5; 424/130.1, 424/143.1

See application file for complete search history.

(56) References Cited

U.S. PATENT DOCUMENTS

2004/0138209 A1    7/2004  Kucharik et al.
2005/0049252 A1    3/2005  Carter et al.
2005/0130197 A1    6/2005  Do et al.

FOREIGN PATENT DOCUMENTS

KR    10-2005-0120471 A    12/2005

OTHER PUBLICATIONS

Lundeen et al, J. of Immunology, vol. 177, No. 5, pp. 3439-3447 (2006).*
Deshpande et al., Cell Signalling, vol. 18, pp. 2105-2120 (2006).*
International Search Report for International Application PCT/KR2008/001650. (May 2, 2008).
Yokomizo T et al., "Hydroxyeicosanoids bind to and activate the low affinity leukotriene B4 receptor, BLT2", J. Biol Chem. Apr. 13, 2001;276(15):12454-12459. Epub Jan. 18, 2001.
Cho SH et al., "Rae and protein kinase C-delta regulate ERKs and cytosolic phospholipase A2 in FcepsilonRI signaling to cysteinyl leukotriene synthesis in mast cells," J. Immunol. Jul. 1, 2004; 173(1): 624-631.
NCBI GenBank Accession No. NM_019839 2799 bp mRNA linear PRI Nov. 17, 2006. Homo sapiens leukotriene B4 receptor 2 (LTB4R2), mRNA.
Deshpande DA et al., "Targeting G protein-coupled receptor signaling in asthma," Cell Signal. Dec. 2006; 18(12): 2105-2120. Epub Jul. 7, 2006.
Shin EH et al., "Leukotriene B4 stimulates human monocyte-derived dendritic cell chemotaxis," Biochem Biophys Res Commun. Sep. 22, 2006; 348(2): 606-611. Epub. Jul. 28, 2006.
Lundeen KA et al., "Leukotriene B4 receptors BLT1 and BLT2:expression and function in human and murine mast cells," J Immunol. Sep. 1, 2006; 177(5): 3439-3447.
Qiu H et al., "Differential induction of BLT receptor expression on human endothelial cells by lipopolysaccharide, cytokines, and leukotriene B4," Proc Natl Acad Sci U S A May 2, 2006; 103(18): 6913-6918. Epub Apr. 19, 2006.
Yokomizo T et al., "A second leukotriene B(4) receptor, BLT2. A new therapeutic target in inflammation and immunological disorders," J Exp Med. Aug. 7, 2007; 192(3): 421-432.

* cited by examiner

*Primary Examiner* — Jane Zara
(74) *Attorney, Agent, or Firm* — Edwards Wildman Palmer LLP; Kongsik Kim

(57) ABSTRACT

The present invention relates to the use of inhibitors of leukotriene B4 receptor BLT2 for treating asthma. More particularly, the present invention relates to a pharmaceutical composition for treating asthma comprising BLT2 inhibitors and a method for treating asthma using BLT2 inhibitors.

10 Claims, 25 Drawing Sheets

Saline provocation

OVA, saline

OVA, antisense Rac (1.25 mg/kg)

OVA, sense Rac (1.25 mg/kg)

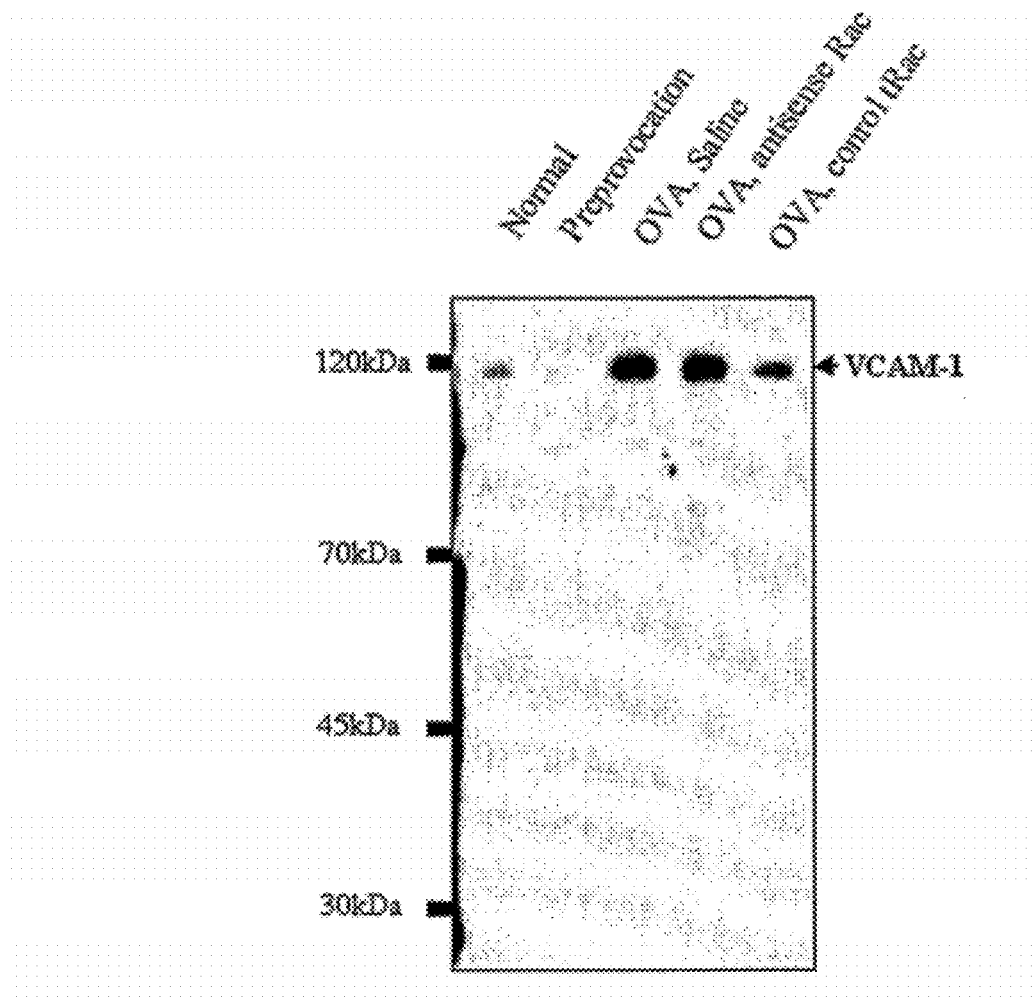

a b

Transient transfection CHO cell
3.0X10⁴ cells/well
$LTB_4$ 300 nM for 3 hrs

Transient transfection CHO cell
3.0X10⁴ cells/well
$LTB_4$ 300 nM for 3 hrs a b

SEQUENCE LISTING

```
<160> NUMBER OF SEQ ID NOS: 27

<210> SEQ ID NO 1
<211> LENGTH: 2798
<212> TYPE: DNA
<213> ORGANISM: homo sapiens

<400> SEQUENCE: 1
aaactggccc tggccctgaa ccaaatacct tgaaccctcg taaactccat accctgaccc      60
ccttgttttg gatatacccca ggtagaacaa ctctctctca ctgtctgttg tgaggatacg     120
ctgtagccca ctcattaagt acattctcct aataaatgct ttggactgat caccctgcca     180
gtcttttgtc ttgggcaatc tatactttc tcagaggttc ccaaggccta ctgaagggac      240
ttaacatact cttaatggct ttcctctctc ttgttttacc ttatgccctc acttcctgag     300
ttaacctccc aaatacagga tcacctgtac ccaagccctt agctcaagaa tacaggatca    360
```

-continued

```
cctgtaccca agcccttagc tcaagctctg ctttggaaga acccaaacta agacagtgct    420
cctggtgccc tccccaagca acctcaagtt ctggctgtta cttgagcaga ggcctttctt    480
ttcccttccc ccagctctat ccatctgcca ggccccctc aaatctcttc atttccaagt     540
tttgcttgac ttttccaaga ggagagggct gcttcttagt atgtccctac tcatcctttc    600
ctttcttgtc ttgtatcctg gtgcagcctg gtaatggggc ctcttcatgg ttgtgtgtca    660
tgactcccta accattatgc ctccatgcat cccctgttcc tcctggaacc tagcaccatg    720
ccttacatgg aaaagctgtc attgacagcc cggtgagagc cctgagggtg gagtgactgg    780
ggcagggcct gaggcaagag gtgggaggag gtaggaggcc aggggctcag ccggaccagg    840
agactggaaa caggcaagga taaggcaggt gggggactga gttgtttggg tcacctctgc    900
aggccagaga gaccaggcaa catacacact gcagaaggtg ggctgggagg attggggcca    960
gagctggggg agggatgaga acagaagcag gaccaggatt cagcagagtc ctcctatttc   1020
cttccaccac cagggaatct tactgcccca cttcagcttg tgctgtttcc tggcaaggca   1080
ggctctcaca tgcctggacg cctgggtgcg ttggtgatgg aaggagcag ggtgagggag    1140 gggcccagg agaggcccag gatgagcctc atcttgtccc tccccattct tgtcttaccc    1200
tctgcaaatg tgataggcac aggacaggag taggcacctc gcctactgct gcttaacctt   1260
tcagcttctc caggccccca atcctgcttg ctcccagctt ggtaagtaga tctgtgcacg   1320 tcccttttaca ccccaccatc cagttttgcc cagatgtgct agaatggggc tggacaaaga  1380
aggaggggcc agactagagg agtggtggta gagatagtga cagcctgggg tgaggacttt   1440
atgcctgttt accactgagc tctgggaagg aggccaggag tggggcaggt caactgactg   1500
ggagcagggg atctgggttc caagaaggag ttgtgtttga ggtggggtct gggtcctcgt   1560
ggaagtcagg actcccaggc agaaaagagg caggctgcag ggaagtaagg aggaggcatg   1620 gcacttctc atcgggcatc acaggtgggg ttttgcccca cccctgaacg ccctctgtgg    1680
cgccttccac ccacctgtag gcccagaagg atgtcggtct gctaccgtcc cccagggaac   1740
gagacactgc tgagctggaa gacttcgcgg gccacaggca cagccttcct gctgctggcg   1800
gcgctgctgg ggctgcctgg caacggcttc gtggtgtgga gcttgcgggc ctggcggcct   1860 gcacggggc gaccgctggc ggccacgctt gtgctgcacc tggcgctggc cgacggcgcg   1920
gtgctgctgc tcacgccgct cttgtgtggcc ttcctgaccc ggcaggcctg gccgctgggc   1980
caggcgggct gcaaggcggt gtactacgtg tgcgcgctca gcatgtacgc cagcgtgctg   2040
ctcaccggcc tgctcagcct gcagcgctgc ctcgcagtca cccgcccctt cctggcgcct   2100
cggctgcgca gcccggccct ggcccgccgc ctgctgctgg cggtctggct ggccgccctg   2160
ttgctcgccg tccggccgc cgtctaccgc cacctgtgga gggaccgcgt atgccagctg   2220
tgccacccgt cgccggtcca cgccgccgcc cacctgagcc tggagactct gaccgctttc   2280
gtgcttcctt tcgggctgat gctcggctgc tacagcgtga cgctggcacg gctgcggggc   2340
gcccgctggg gctccgggcg gcacggggcg cgggtgggcc ggctggtgag cgccatcgtg   2400
cttgccttcg gcttgctctg gccccctac cacgcagtca accttctgca ggcggtcgca   2460
gcgctggctc caccggaagg ggccttggcg aagctgggcg gagccggcca ggcggcgcga   2520
gcgggaacta cggccttggc cttcttcagt tctagcgtca accggtgct ctacgtcttc    2580 accgctggag atctgctgcc ccgggcaggt ccccgtttcc tcacgcggct cttcgaaggc   2640
tctggggagg cccgagggggg cggccgctct agggaaggga ccatggagct ccgaactacc   2700
```

```
cctcagctga aagtggtggg gcagggccgc ggcaatggag acccgggggg tgggatggag    2760
aaggacggtc cggaatggga cctttgacag cagaccct                           2798

<210> SEQ ID NO 2
<211> LENGTH: 1170
<212> TYPE: DNA
<213> ORGANISM: homo sapiens
<220> FEATURE:
<221> NAME/KEY: CDS
<222> LOCATION: (1)..(1167)

<400> SEQUENCE: 2 atg gca cct tct cat cgg gca tca cag gtg ggg ttt tgc ccc acc cct    48
Met Ala Pro Ser His Arg Ala Ser Gln Val Gly Phe Cys Pro Thr Pro
 1               5                  10                  15 gaa cgc cct ctg tgg cgc ctt cca ccc acc tgt agg ccc aga agg atg    96
Glu Arg Pro Leu Trp Arg Leu Pro Pro Thr Cys Arg Pro Arg Arg Met
            20                  25                  30 tcg gtc tgc tac cgt ccc cca ggg aac gag aca ctg ctg agc tgg aag    144
Ser Val Cys Tyr Arg Pro Pro Gly Asn Glu Thr Leu Leu Ser Trp Lys
        35                  40                  45 act tcg cgg gcc aca ggc aca gcc ttc ctg ctg ctg gcg gcg ctg ctg    192
Thr Ser Arg Ala Thr Gly Thr Ala Phe Leu Leu Leu Ala Ala Leu Leu
    50                  55                  60 ggg ctg cct ggc aac ggc ttc gtg gtg tgg agc ttg gcg ggc tgg cgg    240
Gly Leu Pro Gly Asn Gly Phe Val Val Trp Ser Leu Ala Gly Trp Arg
65                  70                  75                  80 cct gca cgg ggg cga ccg ctg gcg gcc acg ctt gtg ctg cac ctg gcg    288
Pro Ala Arg Gly Arg Pro Leu Ala Ala Thr Leu Val Leu His Leu Ala
                85                  90                  95 ctg gcc gac ggc gcg gtg ctg ctc acg ccg ctc ttt gtg gcc ttc        336
Leu Ala Asp Gly Ala Val Leu Leu Thr Pro Leu Phe Val Ala Phe
            100                 105                 110 ctg acc cgg cag gcc tgg ccg ctg ggc cag gcg ggc tgc aag gcg gtg    384
Leu Thr Arg Gln Ala Trp Pro Leu Gly Gln Ala Gly Cys Lys Ala Val
        115                 120                 125 tac tac gtg tgc gcg ctc agc atg tac gcc agc gtg ctg ctc acc ggc    432
Tyr Tyr Val Cys Ala Leu Ser Met Tyr Ala Ser Val Leu Leu Thr Gly
    130                 135                 140 ctg ctc agc ctg cag cgc tgc ctc gca gtc acc cgc ccc ttc ctg gcg    480
Leu Leu Ser Leu Gln Arg Cys Leu Ala Val Thr Arg Pro Phe Leu Ala
145                 150                 155                 160 cct cgg ctg cgc agc ccg gcc ctg gcc cgc cgc ctg ctg gcg gtc        528
Pro Arg Leu Arg Ser Pro Ala Leu Ala Arg Arg Leu Leu Leu Ala Val
                165                 170                 175 tgg ctg gcc gcc ctg ttg ctc gcc gtc ccg gcc gcc gtc tac cgc cac    576
Trp Leu Ala Ala Leu Leu Leu Ala Val Pro Ala Ala Val Tyr Arg His
            180                 185                 190 ctg tgg agg gac cgc gta tgc cag ctg tgc cac ccg tcg ccg gtc cac    624
Leu Trp Arg Asp Arg Val Cys Gln Leu Cys His Pro Ser Pro Val His
        195                 200                 205 gcc gcc gcc cac ctg agc ctg gag act ctg acc gct ttc gtg ctt cct    672
Ala Ala Ala His Leu Ser Leu Glu Thr Leu Thr Ala Phe Val Leu Pro
    210                 215                 220 ttc ggg ctg atg ctc ggc tgc tac agc gtg acg ctg gca cgg ctg cgg    720
Phe Gly Leu Met Leu Gly Cys Tyr Ser Val Thr Leu Ala Arg Leu Arg
225                 230                 235                 240 ggc gcc cgc tgg ggc tcc ggg cgg cac ggg gcg cgg gtg ggc cgg ctg    768
Gly Ala Arg Trp Gly Ser Gly Arg His Gly Ala Arg Val Gly Arg Leu
                245                 250                 255
```

```
gtg agc gcc atc gtg ctt gcc ttc ggc ttg ctc tgg gcc ccc tac cac    816
Val Ser Ala Ile Val Leu Ala Phe Gly Leu Leu Trp Ala Pro Tyr His
            260                 265                 270 gca gtc aac ctt ctg cag gcg gtc gca gcg ctg gct cca ccg gaa ggg    864
Ala Val Asn Leu Leu Gln Ala Val Ala Ala Leu Ala Pro Pro Glu Gly
        275                 280                 285 gcc ttg gcg aag ctg ggc gga gcc ggc cag gcg gcg cga gcg gga act    912
Ala Leu Ala Lys Leu Gly Gly Ala Gly Gln Ala Ala Arg Ala Gly Thr
    290                 295                 300 acg gcc ttg gcc ttc ttc agt tct agc gtc aac ccg gtg ctc tac gtc    960
Thr Ala Leu Ala Phe Phe Ser Ser Ser Val Asn Pro Val Leu Tyr Val
305                 310                 315                 320 ttc acc gct gga gat ctg ctg ccc cgg gca ggt ccc cgt ttc ctc acg   1008
Phe Thr Ala Gly Asp Leu Leu Pro Arg Ala Gly Pro Arg Phe Leu Thr
                325                 330                 335 cgg ctc ttc gaa ggc tct ggg gag gcc cga ggg ggc ggc cgc tct agg   1056
Arg Leu Phe Glu Gly Ser Gly Glu Ala Arg Gly Gly Gly Arg Ser Arg
            340                 345                 350 gaa ggg acc atg gag ctc cga act acc cct cag ctg aaa gtg gtg ggg   1104
Glu Gly Thr Met Glu Leu Arg Thr Thr Pro Gln Leu Lys Val Val Gly
        355                 360                 365 cag ggc cgc ggc aat gga gac ccg ggg ggt ggg atg gag aag gac ggt   1152
Gln Gly Arg Gly Asn Gly Asp Pro Gly Gly Gly Met Glu Lys Asp Gly
    370                 375                 380 ccg gaa tgg gac ctt tga                                            1170
Pro Glu Trp Asp Leu
385

<210> SEQ ID NO 3
<211> LENGTH: 389
<212> TYPE: PRT
<213> ORGANISM: homo sapiens

<400> SEQUENCE: 3

Met Ala Pro Ser His Arg Ala Ser Gln Val Gly Phe Cys Pro Thr Pro
  1               5                  10                  15

Glu Arg Pro Leu Trp Arg Leu Pro Pro Thr Cys Arg Pro Arg Arg Met
             20                  25                  30

Ser Val Cys Tyr Arg Pro Pro Gly Asn Glu Thr Leu Leu Ser Trp Lys
         35                  40                  45

Thr Ser Arg Ala Thr Gly Thr Ala Phe Leu Leu Ala Ala Leu Leu
     50                  55                  60

Gly Leu Pro Gly Asn Gly Phe Val Val Trp Ser Leu Ala Gly Trp Arg
 65                  70                  75                  80

Pro Ala Arg Gly Arg Pro Leu Ala Ala Thr Leu Val Leu His Leu Ala
                 85                  90                  95

Leu Ala Asp Gly Ala Val Leu Leu Leu Thr Pro Leu Phe Val Ala Phe
            100                 105                 110

Leu Thr Arg Gln Ala Trp Pro Leu Gly Gln Ala Gly Cys Lys Ala Val
        115                 120                 125

Tyr Tyr Val Cys Ala Leu Ser Met Tyr Ala Ser Val Leu Leu Thr Gly
    130                 135                 140

Leu Leu Ser Leu Gln Arg Cys Leu Ala Val Thr Arg Pro Phe Leu Ala
145                 150                 155                 160

Pro Arg Leu Arg Ser Pro Ala Leu Ala Arg Leu Leu Leu Ala Val
                165                 170                 175

Trp Leu Ala Ala Leu Leu Leu Ala Val Pro Ala Ala Val Tyr Arg His
            180                 185                 190
```

```
Leu Trp Arg Asp Arg Val Cys Gln Leu Cys His Pro Ser Pro Val His
            195                 200                 205
Ala Ala Ala His Leu Ser Leu Glu Thr Leu Thr Ala Phe Val Leu Pro
        210                 215                 220
Phe Gly Leu Met Leu Gly Cys Tyr Ser Val Thr Leu Ala Arg Leu Arg
225                 230                 235                 240
Gly Ala Arg Trp Gly Ser Gly Arg His Gly Ala Arg Val Gly Arg Leu
                245                 250                 255
Val Ser Ala Ile Val Leu Ala Phe Gly Leu Leu Trp Ala Pro Tyr His
            260                 265                 270
Ala Val Asn Leu Leu Gln Ala Val Ala Ala Leu Ala Pro Pro Glu Gly
        275                 280                 285
Ala Leu Ala Lys Leu Gly Gly Ala Gly Gln Ala Ala Arg Ala Gly Thr
    290                 295                 300
Thr Ala Leu Ala Phe Phe Ser Ser Ser Val Asn Pro Val Leu Tyr Val
305                 310                 315                 320
Phe Thr Ala Gly Asp Leu Leu Pro Arg Ala Gly Pro Arg Phe Leu Thr
                325                 330                 335
Arg Leu Phe Glu Gly Ser Gly Glu Ala Arg Gly Gly Arg Ser Arg
            340                 345                 350
Glu Gly Thr Met Glu Leu Arg Thr Thr Pro Gln Leu Lys Val Val Gly
        355                 360                 365
Gln Gly Arg Gly Asn Gly Asp Pro Gly Gly Gly Met Glu Lys Asp Gly
    370                 375                 380
Pro Glu Trp Asp Leu
385

<210> SEQ ID NO 4
<211> LENGTH: 1077
<212> TYPE: DNA
<213> ORGANISM: homo sapiens
<220> FEATURE:
<221> NAME/KEY: CDS
<222> LOCATION: (1)..(1074)

<400> SEQUENCE: 4 atg tcg gtc tgc tac cgt ccc cca ggg aac gag aca ctg ctg agc tgg      48
Met Ser Val Cys Tyr Arg Pro Pro Gly Asn Glu Thr Leu Leu Ser Trp
1               5                   10                  15 aag act tcg cgg gcc aca ggc aca gcc ttc ctg ctg ctg gcg gcg ctg      96
Lys Thr Ser Arg Ala Thr Gly Thr Ala Phe Leu Leu Leu Ala Ala Leu
            20                  25                  30 ctg ggg ctg cct ggc aac ggc ttc gtg gtg tgg agc ttg gcg ggc tgg     144
Leu Gly Leu Pro Gly Asn Gly Phe Val Val Trp Ser Leu Ala Gly Trp
        35                  40                  45 cgg cct gca cgg ggg cga ccg ctg gcg gcc acg ctt gtg ctg cac ctg     192
Arg Pro Ala Arg Gly Arg Pro Leu Ala Ala Thr Leu Val Leu His Leu
    50                  55                  60 gcg ctg gcc gac ggc gcg gtg ctg ctc acg ccg ctc ttt gtg gcc         240
Ala Leu Ala Asp Gly Ala Val Leu Leu Leu Thr Pro Leu Phe Val Ala
65                  70                  75                  80 ttc ctg acc cgg cag gcc tgg ccg ctg ggc cag gcg ggc tgc aag gcg     288
Phe Leu Thr Arg Gln Ala Trp Pro Leu Gly Gln Ala Gly Cys Lys Ala
                85                  90                  95 gtg tac tac gtg tgc gcg ctc agc atg tac gcc agc gtg ctg ctc acc     336
Val Tyr Tyr Val Cys Ala Leu Ser Met Tyr Ala Ser Val Leu Leu Thr
            100                 105                 110
```

```
ggc ctg ctc agc ctg cag cgc tgc ctc gca gtc acc cgc ccc ttc ctg      384
Gly Leu Leu Ser Leu Gln Arg Cys Leu Ala Val Thr Arg Pro Phe Leu
            115                 120                 125 gcg cct cgg ctg cgc agc ccg gcc ctg gcc cgc cgc ctg ctg ctg gcg      432
Ala Pro Arg Leu Arg Ser Pro Ala Leu Ala Arg Arg Leu Leu Leu Ala
        130                 135                 140 gtc tgg ctg gcc gcc ctg ttg ctc gcc gtc ccg gcc gcc gtc tac cgc      480
Val Trp Leu Ala Ala Leu Leu Leu Ala Val Pro Ala Ala Val Tyr Arg
145                 150                 155                 160 cac ctg tgg agg gac cgc gta tgc cag ctg tgc cac ccg tcg ccg gtc      528
His Leu Trp Arg Asp Arg Val Cys Gln Leu Cys His Pro Ser Pro Val
                165                 170                 175 cac gcc gcc gcc cac ctg agc ctg gag act ctg acc gct ttc gtg ctt      576
His Ala Ala Ala His Leu Ser Leu Glu Thr Leu Thr Ala Phe Val Leu
            180                 185                 190 cct ttc ggg ctg atg ctc ggc tgc tac agc gtg acg ctg gca cgg ctg      624
Pro Phe Gly Leu Met Leu Gly Cys Tyr Ser Val Thr Leu Ala Arg Leu
        195                 200                 205 cgg ggc gcc cgc tgg ggc tcc ggg cgc cac ggg gcg cgg gtg ggc cgg      672
Arg Gly Ala Arg Trp Gly Ser Gly Arg His Gly Ala Arg Val Gly Arg
    210                 215                 220 ctg gtg agc gcc atc gtg ctt gcc ttc ggc ttg ctc tgg gcc ccc tac      720
Leu Val Ser Ala Ile Val Leu Ala Phe Gly Leu Leu Trp Ala Pro Tyr
225                 230                 235                 240 cac gca gtc aac ctt ctg cag gcg gtc gca gcg ctg gct cca ccg gaa      768
His Ala Val Asn Leu Leu Gln Ala Val Ala Ala Leu Ala Pro Pro Glu
                245                 250                 255 ggg gcc ttg gcg aag ctg ggc gga gcc ggc cag gcg gcg cga gcg gga      816
Gly Ala Leu Ala Lys Leu Gly Gly Ala Gly Gln Ala Ala Arg Ala Gly
            260                 265                 270 act acg gcc ttg gcc ttc ttc agt tct agc gtc aac ccg gtg ctc tac      864
Thr Thr Ala Leu Ala Phe Phe Ser Ser Ser Val Asn Pro Val Leu Tyr
        275                 280                 285 gtc ttc acc gct gga gat ctg ctg ccc cgg gca ggt ccc cgt ttc ctc      912
Val Phe Thr Ala Gly Asp Leu Leu Pro Arg Ala Gly Pro Arg Phe Leu
    290                 295                 300 acg cgg ctc ttc gaa ggc tct ggg gag gcc cga ggg ggc ggc cgc tct      960
Thr Arg Leu Phe Glu Gly Ser Gly Glu Ala Arg Gly Gly Gly Arg Ser
305                 310                 315                 320 agg gaa ggg acc atg gag ctc cga act acc cct cag ctg aaa gtg gtg     1008
Arg Glu Gly Thr Met Glu Leu Arg Thr Thr Pro Gln Leu Lys Val Val
                325                 330                 335 ggg cag ggc cgc ggc aat gga gac ccg ggg ggt ggg atg gag aag gac     1056
Gly Gln Gly Arg Gly Asn Gly Asp Pro Gly Gly Gly Met Glu Lys Asp
            340                 345                 350 ggt ccg gaa tgg gac ctt tga                                         1077
Gly Pro Glu Trp Asp Leu
        355

<210> SEQ ID NO 5
<211> LENGTH: 358
<212> TYPE: PRT
<213> ORGANISM: homo sapiens

<400> SEQUENCE: 5

Met Ser Val Cys Tyr Arg Pro Pro Gly Asn Glu Thr Leu Leu Ser Trp
 1               5                  10                  15

Lys Thr Ser Arg Ala Thr Gly Thr Ala Phe Leu Leu Leu Ala Ala Leu
            20                  25                  30

Leu Gly Leu Pro Gly Asn Gly Phe Val Val Trp Ser Leu Ala Gly Trp
```

```
            35                  40                  45
Arg Pro Ala Arg Gly Arg Pro Leu Ala Ala Thr Leu Val Leu His Leu
 50                  55                  60

Ala Leu Ala Asp Gly Ala Val Leu Leu Leu Thr Pro Leu Phe Val Ala
 65                  70                  75                  80

Phe Leu Thr Arg Gln Ala Trp Pro Leu Gly Gln Ala Gly Cys Lys Ala
                 85                  90                  95

Val Tyr Tyr Val Cys Ala Leu Ser Met Tyr Ala Ser Val Leu Leu Thr
                100                 105                 110

Gly Leu Leu Ser Leu Gln Arg Cys Leu Ala Val Thr Arg Pro Phe Leu
                115                 120                 125

Ala Pro Arg Leu Arg Ser Pro Ala Leu Ala Arg Arg Leu Leu Leu Ala
130                 135                 140

Val Trp Leu Ala Ala Leu Leu Ala Val Pro Ala Ala Val Tyr Arg
145                 150                 155                 160

His Leu Trp Arg Asp Arg Val Cys Gln Leu Cys His Pro Ser Pro Val
                165                 170                 175

His Ala Ala Ala His Leu Ser Leu Glu Thr Leu Thr Ala Phe Val Leu
                180                 185                 190

Pro Phe Gly Leu Met Leu Gly Cys Tyr Ser Val Thr Leu Ala Arg Leu
                195                 200                 205

Arg Gly Ala Arg Trp Gly Ser Gly Arg His Gly Ala Arg Val Gly Arg
210                 215                 220

Leu Val Ser Ala Ile Val Leu Ala Phe Gly Leu Leu Trp Ala Pro Tyr
225                 230                 235                 240

His Ala Val Asn Leu Leu Gln Ala Val Ala Ala Leu Ala Pro Pro Glu
                245                 250                 255

Gly Ala Leu Ala Lys Leu Gly Gly Ala Gly Gln Ala Ala Arg Ala Gly
                260                 265                 270

Thr Thr Ala Leu Ala Phe Phe Ser Ser Ser Val Asn Pro Val Leu Tyr
                275                 280                 285

Val Phe Thr Ala Gly Asp Leu Leu Pro Arg Ala Gly Pro Arg Phe Leu
290                 295                 300

Thr Arg Leu Phe Glu Gly Ser Gly Glu Ala Arg Gly Gly Arg Ser
305                 310                 315                 320

Arg Glu Gly Thr Met Glu Leu Arg Thr Thr Pro Gln Leu Lys Val Val
                325                 330                 335

Gly Gln Gly Arg Gly Asn Gly Asp Pro Gly Gly Gly Met Glu Lys Asp
                340                 345                 350

Gly Pro Glu Trp Asp Leu
        355

<210> SEQ ID NO 6
<211> LENGTH: 15
<212> TYPE: DNA
<213> ORGANISM: Artificial Sequence
<220> FEATURE:
<223> OTHER INFORMATION: hBLT2 anti-sense sequence

<400> SEQUENCE: 6
cagcagtgtc tcgtt                                                       15

<210> SEQ ID NO 7
<211> LENGTH: 21
<212> TYPE: RNA
<213> ORGANISM: Artificial Sequence
```

```
<220> FEATURE:
<223> OTHER INFORMATION: hBLT2 siRNA sense sequence

<400> SEQUENCE: 7
gaaggauguc ggucugcuau u                                        21

<210> SEQ ID NO 8
<211> LENGTH: 21
<212> TYPE: RNA
<213> ORGANISM: Artificial Sequence
<220> FEATURE:
<223> OTHER INFORMATION: hBLT2 siRNA antisense sequence

<400> SEQUENCE: 8
uagcagaccg acauccuucu u                                        21

<210> SEQ ID NO 9
<211> LENGTH: 25
<212> TYPE: DNA
<213> ORGANISM: Artificial Sequence
<220> FEATURE:
<223> OTHER INFORMATION: forward primer for hBLT2

<400> SEQUENCE: 9
agcctggaga ctctgaccgc tttcg                                    25

<210> SEQ ID NO 10
<211> LENGTH: 25
<212> TYPE: DNA
<213> ORGANISM: Artificial Sequence
<220> FEATURE:
<223> OTHER INFORMATION: reverse primer for hBLT2

<400> SEQUENCE: 10
gacgtagagc accgggttga cgcta                                    25

<210> SEQ ID NO 11
<211> LENGTH: 20
<212> TYPE: DNA
<213> ORGANISM: Artificial Sequence
<220> FEATURE:
<223> OTHER INFORMATION: forward primer for re-hBLT2

<400> SEQUENCE: 11
tctcatcggg catcacaggt                                          20

<210> SEQ ID NO 12
<211> LENGTH: 20
<212> TYPE: DNA
<213> ORGANISM: Artificial Sequence
<220> FEATURE:
<223> OTHER INFORMATION: reverse primer for re-hBLT2

<400> SEQUENCE: 12
ccaagctcca caccacgaag                                          20

<210> SEQ ID NO 13
<211> LENGTH: 2398
<212> TYPE: DNA
<213> ORGANISM: homo sapiens
<220> FEATURE:
<221> NAME/KEY: CDS
<222> LOCATION: (242)..(874)

<400> SEQUENCE: 13
gggaggccgg atgtgagtgg agcggccatt tcctgtttct ctgcagtttt cctcagcttt    60
```

-continued

```
gggtggtggc cgctgccggg catcggcttc cagtccgcgg agggcgaggc ggcgtggaca    120
gcggccccgg cacccagcgc cccgccgccc gcaagccgcg cgcccgtccg ccgcgccccg    180
agcccgccgc ttcctatctc agcgccctgc cgccgccgcc gcggcccagc gagcggccct    240 g atg cag gcc atc aag tgt gtg gtg gtg gga gac gga gct gta    283
           Met Gln Ala Ile Lys Cys Val Val Val Gly Asp Gly Ala Val
             1               5                  10 ggt aaa act tgc cta ctg atc agt tac aca acc aat gca ttt cct gga     331
Gly Lys Thr Cys Leu Leu Ile Ser Tyr Thr Thr Asn Ala Phe Pro Gly
 15                  20                  25                  30 gaa tat atc cct act gtc ttt gac aat tat tct gcc aat gtt atg gta    379
Glu Tyr Ile Pro Thr Val Phe Asp Asn Tyr Ser Ala Asn Val Met Val
                 35                  40                  45 gat gga aaa ccg gtg aat ctg ggc tta tgg gat aca gct gga caa gaa    427
Asp Gly Lys Pro Val Asn Leu Gly Leu Trp Asp Thr Ala Gly Gln Glu
             50                  55                  60 gat tat gac aga tta cgc ccc cta tcc tat ccg caa aca gtt gga gaa    475
Asp Tyr Asp Arg Leu Arg Pro Leu Ser Tyr Pro Gln Thr Val Gly Glu
 65                  70                  75 acg tac ggt aag gat ata acc tcc cgg ggc aaa gac aag ccg att gcc    523
Thr Tyr Gly Lys Asp Ile Thr Ser Arg Gly Lys Asp Lys Pro Ile Ala
     80                  85                  90 gat gtg ttc tta att tgc ttt tcc ctt gtg agt cct gca tca ttt gaa    571
Asp Val Phe Leu Ile Cys Phe Ser Leu Val Ser Pro Ala Ser Phe Glu
 95                 100                 105                 110 aat gtc cgt gca aag tgg tat cct gag gtg cgg cac cac tgt ccc aac    619
Asn Val Arg Ala Lys Trp Tyr Pro Glu Val Arg His His Cys Pro Asn
                115                 120                 125 act ccc atc atc cta gtg gga act aaa ctt gat ctt agg gat gat aaa    667
Thr Pro Ile Ile Leu Val Gly Thr Lys Leu Asp Leu Arg Asp Asp Lys
            130                 135                 140 gac acg atc gag aaa ctg aag gag aag aag ctg act ccc atc acc tat    715
Asp Thr Ile Glu Lys Leu Lys Glu Lys Lys Leu Thr Pro Ile Thr Tyr
        145                 150                 155 ccg cag ggt cta gcc atg gct aag gag att ggt gct gta aaa tac ctg    763
Pro Gln Gly Leu Ala Met Ala Lys Glu Ile Gly Ala Val Lys Tyr Leu
    160                 165                 170 gag tgc tcg gcg ctc aca cag cga ggc ctc aag aca gtg ttt gac gaa    811
Glu Cys Ser Ala Leu Thr Gln Arg Gly Leu Lys Thr Val Phe Asp Glu
175                 180                 185                 190 gcg atc cga gca gtc ctc tgc ccg cct ccc gtg aag aag agg aag aga    859
Ala Ile Arg Ala Val Leu Cys Pro Pro Pro Val Lys Lys Arg Lys Arg
                195                 200                 205 aaa tgc ctg ctg ttg taaatg tctcagcccc tcgttcttgg tcctgtccct        910
Lys Cys Leu Leu Leu
                210 tggaacctttgtacgctttg ctcaaaaaaa aacaaaaaaa aaaacaaaa aaaaaaaaca     970 acggtggagc cttcgcactc aatgccaact ttttgttaca gattaatttt tccataaaac  1030
cattttttga accaatcagt aatttttaagg ttttgtttgt tctaaatgta agagttcaga  1090
ctcacattct attaaaattt agccctaaaa tgacaagcct tcttaaagcc ttattttttca 1150 aaagcgcccc ccccattctt gttcagatta agagttgcca aaataccttc tgaactacac  1210
tgcattgttg tgccgagaac accgagcact gaactttgca aagaccttcg tctttgagaa  1270
gacggtagct tctgcagtta ggaggtgcag acacttgctc tcctatgtag ttctcagatg  1330
cgtaaagcag aacagcctcc cgaatgaagc gttgccattg aactcaccag tgagttagca  1390
```

-continued

```
gcacgtgttc cgacataac attgtactgt aatggagtga gcgtagcagc tcagctcttt    1450
ggatcagtct ttgtgatttc atagcgagtt ttctgaccag cttttgcgga gattttgaac    1510
agaactgcta tttcctctaa tgaagaattc tgtttagctg tgggtgtgcc gggtggggtg    1570
tgtgtgatca aaggacaaag acagtatttt gacaaaatac gaagtggaga tttacactac    1630
attgtacaag gaatgaaagt gtcacgggta aaaactctaa aaggttaatt tctgtcaaat    1690
gcagtagatg atgaaagaaa ggttggtatt atcaggaaat gttttcttaa gcttttcctt    1750
tctcttacac ctgccatgcc tccccaaatt gggcatttaa ttcatcttta aactggttgt    1810
tctgttagtc gctaacttag taagtgcttt tcttatagaa ccccttctga ctgagcaata    1870
tgcctccttg tattataaaa tctttctgat aatgcattag aaggtttttt tgtcgattag    1930
taaaagtgct ttccatgtta ctttattcag agctaataag tgctttcctt agttttctag    1990
taactaggtg taaaaatcat gtgttgcagc tttatagttt ttaaaatatt ttagataatt    2050
cttaaactat gaaccttctt aacatcactg tcttgccaga ttaccgacac tgtcacttga    2110
ccaatactga ccctctttac ctcgcccacg cggacacacg cctcctgtag tcgctttgcc    2170
tattgatgtt cctttgggtc tgtgaggttc tgtaaactgt gctagtgctg acgatgttct    2230
gtacaactta actcactggc gagaatacag cgtgggaccc ttcagccact acaacagaat    2290
tttttaaatt gacagttgca gaattgtgga gtgttttac attgatcttt gctaatgca     2350 attagcatta tgttttgcat gtatgactta ataaatcctt gaatcata                 2398
```

<210> SEQ ID NO 14
<211> LENGTH: 211
<212> TYPE: PRT
<213> ORGANISM: homo sapiens

<400> SEQUENCE: 14

```
Met Gln Ala Ile Lys Cys Val Val Gly Asp Gly Ala Val Gly Lys
  1               5                  10                  15

Thr Cys Leu Leu Ile Ser Tyr Thr Thr Asn Ala Phe Pro Gly Glu Tyr
                 20                  25                  30

Ile Pro Thr Val Phe Asp Asn Tyr Ser Ala Asn Val Met Val Asp Gly
             35                  40                  45

Lys Pro Val Asn Leu Gly Leu Trp Asp Thr Ala Gly Gln Glu Asp Tyr
         50                  55                  60

Asp Arg Leu Arg Pro Leu Ser Tyr Pro Gln Thr Val Gly Glu Thr Tyr
 65                  70                  75                  80

Gly Lys Asp Ile Thr Ser Arg Gly Lys Asp Lys Pro Ile Ala Asp Val
                 85                  90                  95

Phe Leu Ile Cys Phe Ser Leu Val Ser Pro Ala Ser Phe Glu Asn Val
            100                 105                 110

Arg Ala Lys Trp Tyr Pro Glu Val Arg His His Cys Pro Asn Thr Pro
        115                 120                 125

Ile Ile Leu Val Gly Thr Lys Leu Asp Leu Arg Asp Asp Lys Asp Thr
    130                 135                 140

Ile Glu Lys Leu Lys Glu Lys Lys Leu Thr Pro Ile Thr Tyr Pro Gln
145                 150                 155                 160

Gly Leu Ala Met Ala Lys Glu Ile Gly Ala Val Lys Tyr Leu Glu Cys
                165                 170                 175

Ser Ala Leu Thr Gln Arg Gly Leu Lys Thr Val Phe Asp Glu Ala Ile
            180                 185                 190

Arg Ala Val Leu Cys Pro Pro Pro Val Lys Lys Arg Lys Arg Lys Cys
```

```
            195                 200                 205

Leu Leu Leu
    210
```

<210> SEQ ID NO 15
<211> LENGTH: 20
<212> TYPE: DNA
<213> ORGANISM: Artificial Sequence
<220> FEATURE:
<223> OTHER INFORMATION: hBLT2 anti-sense sequence

<400> SEQUENCE: 15
gctcagtagt gtctcattcc                                          20

<210> SEQ ID NO 16
<211> LENGTH: 20
<212> TYPE: DNA
<213> ORGANISM: Artificial Sequence
<220> FEATURE:
<223> OTHER INFORMATION: hBLT2 siRNA sense sequence

<400> SEQUENCE: 16
ggaatgagac actactgagc                                          20

<210> SEQ ID NO 17
<211> LENGTH: 20
<212> TYPE: DNA
<213> ORGANISM: Artificial Sequence
<220> FEATURE:
<223> OTHER INFORMATION: forward primer for mouse BLT2

<400> SEQUENCE: 17
cagcatgtac gccagcgtgc                                          20

<210> SEQ ID NO 18
<211> LENGTH: 19
<212> TYPE: DNA
<213> ORGANISM: Artificial Sequence
<220> FEATURE:
<223> OTHER INFORMATION: reverse primer for mouse BLT2

<400> SEQUENCE: 18
cgatggcgct caccagacg                                           19

<210> SEQ ID NO 19
<211> LENGTH: 20
<212> TYPE: DNA
<213> ORGANISM: Artificial Sequence
<220> FEATURE:
<223> OTHER INFORMATION: forward primer for mouse BLT1

<400> SEQUENCE: 19
gcatgtccct gtctctgttg                                          20

<210> SEQ ID NO 20
<211> LENGTH: 20
<212> TYPE: DNA
<213> ORGANISM: Artificial Sequence
<220> FEATURE:
<223> OTHER INFORMATION: reverse primer for mouse BLT1

<400> SEQUENCE: 20
cgggcaaagg ccttagtacg                                          20

<210> SEQ ID NO 21

```
<211> LENGTH: 17
<212> TYPE: DNA
<213> ORGANISM: Artificial Sequence
<220> FEATURE:
<223> OTHER INFORMATION: Rac siRNA sense sequence

<400> SEQUENCE: 21
gatcagtgca cacagtg                                                    17

<210> SEQ ID NO 22
<211> LENGTH: 17
<212> TYPE: DNA
<213> ORGANISM: Artificial Sequence
<220> FEATURE:
<223> OTHER INFORMATION: Rac anti-sense sequence

<400> SEQUENCE: 22
cacttgatgg cctgcat                                                    17

<210> SEQ ID NO 23
<211> LENGTH: 20
<212> TYPE: DNA
<213> ORGANISM: Artificial Sequence
<220> FEATURE:
<223> OTHER INFORMATION: forward primer for re-hBLT2

<400> SEQUENCE: 23
tctcatcggg catcacaggt                                                 20

<210> SEQ ID NO 24
<211> LENGTH: 20
<212> TYPE: DNA
<213> ORGANISM: Artificial Sequence
<220> FEATURE:
<223> OTHER INFORMATION: reverse primer for re-hBLT2

<400> SEQUENCE: 24
ccaagctcca caccacgaag                                                 20

<210> SEQ ID NO 25
<211> LENGTH: 19
<212> TYPE: DNA
<213> ORGANISM: Artificial Sequence
<220> FEATURE:
<223> OTHER INFORMATION: hBLT2 siRNA target sequence

<400> SEQUENCE: 25
gaaggatgtc ggtctgcta                                                  19

<210> SEQ ID NO 26
<211> LENGTH: 20
<212> TYPE: DNA
<213> ORGANISM: Artificial Sequence
<220> FEATURE:
<223> OTHER INFORMATION: forward primer for hBLT2 coding region fragment

<400> SEQUENCE: 26
cttctcatcg ggcatcacag                                                 20

<210> SEQ ID NO 27
<211> LENGTH: 20
<212> TYPE: DNA
<213> ORGANISM: Artificial Sequence
<220> FEATURE:
<223> OTHER INFORMATION: reverse primer for hBLT2 coding region fragment
```

```
<400> SEQUENCE: 27
atccttctgg gcctacaggt                                               20
```

USE OF INHIBITORS OF LEUKOTRIENE B4 RECEPTOR BLT2 FOR TREATING ASTHMA

CROSS-REFERENCE TO RELATED APPLICATIONS

This application is a continuation-in-part of U.S. application Ser. No. 12/450,342, filed on Sep. 22, 2009, and published as U.S. Patent Application Publication No. 2010/0034835, which is the U.S. national phase, pursuant to 35 U.S.C. §371, of International Application No. PCT/KR2008/001650, which was filed on Mar. 24, 2008, and published as International Publication No. WO 2008/117971, which claims the benefit of U.S. Provisional Application Nos. 60/896,501, which was filed on Mar. 23, 2007, and 60/896,502, which was filed on Mar. 23, 2007, the disclosures of which are hereby incorporated in their entireties.

FIELD OF INVENTION

The present invention relates to use of inhibitors of leukotriene B4 receptor BLT2 for treating asthma. More particularly, the present invention relates to a pharmaceutical composition for treating asthma comprising BLT2 inhibitors and a method for treating asthma using BLT2 inhibitors.

BACKGROUND OF THE INVENTION

Leukotriene B4 ($LTB_4$) is a key mediator of inflammatory processes, immune responses, and host defenses against infection (1-4). It stimulates chemotaxis, degranulation, release of lysosomal enzymes, and the production of reactive oxygen species (ROS) (5-7). In fact, $LTB_4$ is one of the most potent chemoattractants known, acting mainly on granulocytes and monocytes (8, 9). Recently, it was also shown to be a chemoattractant for effector CD4+ and CD8+ T lymphocytes, recruiting them to sites of acute inflammation (10-15). It also promotes cell adhesion to vascular endothelial cells and transmigration (8, 16), which amplifies inflammatory early responses. Although $LTB_4$-induced leukocyte recruitment is thought to play a protective role in host defense against various pathogens, it is also involved in a number of human inflammatory diseases such as asthma (17-20), a disease of chronic airway inflammation characterized by eosinophilic infiltration, mucus hypersecretion, and airway hyperresponsiveness (AHR). Thus, a significantly increased level of $LTB_4$ is detected in the airways of patients with asthma and also in experimental models of asthma (20).

$LTB_4$ produces its biological effects via specific G protein-coupled receptors known as BLT1 and BLT2 (21-24). To date, most studies of $LTB_4$ receptors have focused on the high-affinity $LTB_4$ receptor, BLT1, expressed exclusively in leukocytes, especially its role in inflammatory responses (22). For example, early recruitment of neutrophils and eosinophils into the airways in response to allergen inhalation is reduced in BLT1-deficient mice (8, 25), suggesting a role of BLT1 in the chemotaxis of granulocytes in allergic asthma. In addition, BLT1 is essential for the allergen-mediated early recruitment of CD4+ and CD8+ T cells into the lung airways and the development of allergen-induced AHR and inflammation under certain experimental conditions (26, 27). In contrast to BLT1, BLT2 has a low affinity for $LTB_4$ and is expressed in a wide variety of tissues, with highest levels in the spleen, leukocytes and ovary (23).

The role of BLT2 in the pathogenesis of asthma was investigated using a murine model. By employing antisense to block endogenous BLT2 expression, a critical role for BLT2 in the development of AHR and airway inflammation was demonstrated. In addition, without being bound to a particular theory, BLT2 causes asthmatic symptoms by elevating ROS generation and subsequent NF-κB activation. Furthermore, immunohistochmical analysis of clinical asthma samples revealed a significant elevation of expression of BLT2 mainly in the airway epithelial layers as well as in the microvascular endothelium, which is similar to the pattern observed in the murine model of asthma.

Asthma is thought to be caused by a combination of genetic and environmental factors. The prevalence of asthma has increased significantly since the 1970s. As of 2010, 300 million people were affected worldwide. In 2009 asthma caused 250,000 deaths globally. Symptoms of asthma can be prevented by avoiding triggers, such as allergens and irritants, and by inhaling corticosteroids. However, long-term corticosteroid use has the potential to cause severe side-effects including, e.g., hyperglycemia, insulin resistance, diabetes mellitus, osteoporosis, cataract, anxiety, depression, colitis, hypertension, ictus, erectile dysfunction, hypogonadism, hypothyroidism, amenorrhoea, and retinopathy. Accordingly, new compositions and methods for treating asthma are urgently required.

SUMMARY OF THE INVENTION

It is therefore an object of the present invention to provide use of a BLT2 inhibitor (e.g., an antibody against long form BLT2) in a medicament for the treatment of asthma.

Further, another object of the present invention is to provide a pharmaceutical composition for the treatment of asthma comprising a BLT2 inhibitor (e.g., an antibody against long form BLT2) as an active ingredient.

Further, another object of the present invention is to provide a method for treating a patient with asthma, which comprises administering an effective amount of BLT2 inhibitor (e.g., an antibody against long form BLT2) to the patient.

Further, another object of the present invention is to provide a method for screening a substance for treating asthma, which comprises determining whether to reduce the expression or signaling level of BLT2.

Further, another object of the present invention is to provide a kit for detecting asthma, which comprises a primer or probe for detecting a BLT2 nucleic acid molecule or an antibody for detecting BLT2 protein.

Further, another object of the present invention is to provide use of a Rac inhibitor in a medicament for the treatment of asthma.

Thus, the invention provides use of BLT2 inhibitors (e.g., anti-long form BLT2 antibody) for (1) suppressing an allergic response (e.g., asthma), (2) suppressing immune responses of mast cells, (3) suppressing Th2 cytokine IL-13 release, and (4) suppressing one or more of eosinophil infiltration into lung airway, airway inflammation, and airway hyperresponsiveness. Also, this invention include (4) a novel strategy for screening BLT2 signaling inhibitors by measuring the cell growth of Rat2-BLT2 stable cells. Thus, the invention claims the use of strategies targeting BLT2 overexpression or overactivation as a tool for developing therapeutic composition against asthma.

The invention is at least based in part on the discovery of a relationship between asthma and a BLT2-linked signaling cascade. Without being bound to a particular theory, $LTB_4$ exerts its effects through both BLT1- and BLT2-dependent signaling pathways and that the two may cooperate during the development of allergic asthma. Attenuation of either pathway suppressed asthmatic symptoms. A better understanding of the BLT2-linked pathway and possible cross-regulation between the BLT1 and BLT2 pathways should help to clarify their role in $LTB_4$-mediated allergic pathogenesis. The finding that a $LTB_4$-BLT2-ROS pathway is involved in asthma serves as the basis for the development of new diagnostic tools and treatments for allergic disease.

In one aspect, the invention provides, a method of treating asthma in a patient, the method comprising administering to the patient a therapeutically effective amount of an agent that inhibits the expression or intracellular signaling of long-form BLT2.

In another aspect, the invention provides a method of reducing expression or activity of long-form BLT2 in a lung cell or immune cell, the method comprising contacting the lung cell or immune cell with an effective amount of an agent that inhibits the expression or intracellular signaling of long-form BLT2.

In still another aspect, the invention provides a monoclonal antibody that inhibits expression or intracellular signaling of long-form BLT2 in a lung cell or immune cell. In various embodiments, the monoclonal antibody is used for the treatment of asthma.

In a related aspect, the invention provides a pharmaceutical composition contains a monoclonal antibody that inhibits expression or intracellular signaling of long-form BLT2 in a lung cell or immune cell and a pharmaceutical carrier.

In yet another aspect, the invention provides a method for screening an agent for treating asthma, the method involving contacting a lung cell or immune cell containing a long-form BLT2 gene or long-form BLT2 protein; and measuring the expression or activity of long-form BLT2, wherein a decrease in the expression or activity of long-form BLT2 indicates the agent can be used for treating asthma.

In an additional aspect, the invention provides a kit for the treatment of asthma, the kit comprising an agent that inhibits the expression or intracellular signaling of long-form BLT2.

In various embodiments of any of the aspects delineated herein, the agent selectively reduces the expression or intracellular signaling of long-form BLT2 while the expression or intracellular signaling of short-form BLT2 is not disrupted. In various embodiments of any of the aspects delineated herein, the asthma is characterized by the overexpression of long-form BLT2 in the lung airway. In various embodiments of any of the aspects delineated herein, the expression or activity of an asthma-associated Th2 cytokine selected from the group consisting of IL-13 is reduced. In various embodiments of any of the aspects delineated herein, one or more of eosinophil infiltration into lung airway, airway inflammation, or airway hyperresponsiveness (AHR) is reduced. In various embodiments of any of the aspects delineated herein, long-form BLT2 activation increases ROS generation and NF-κB activation. In various embodiments of any of the aspects delineated herein, the method further comprises administering a therapeutically effective amount of an agent that inhibits the expression or activity of Rac.

In various embodiments of any of the aspects delineated herein, the agent is an antibody or fragment thereof that specifically binds long-form BLT-2. In various embodiments, the antibody or fragment thereof specifically binds long-form BLT-2 in the region set forth by amino acids 1-31 of SEQ ID NO: 3. In particular embodiments, the antibody or fragment thereof specifically binds long-form BLT-2 in the region set forth by amino acids 14-27 of SEQ ID NO: 3. In various embodiments of any of the aspects delineated herein, the antibody is a polyclonal or monoclonal antibody.

In various embodiments of any of the aspects delineated herein, the agent is an inhibitory nucleic acid that is complementary to at least a portion of a long-form BLT2 nucleic acid molecule. In various embodiments, the inhibitory nucleic acid is complementary to at least a portion of a long-form BLT2 nucleic acid molecule in the region set forth by nucleotides 1-93 of SEQ ID NO: 2. In various embodiments of any of the aspects delineated herein, the inhibitory nucleic acid is selected from the group consisting of an antisense molecule, and siRNA, and an shRNA.

Other objects and advantage of the present invention will become apparent from the detailed description to follow taken in conjugation with the appended claims and drawings.

BRIEF DESCRIPTION OF THE DRAWINGS

FIG. 1a is a graph showing levels of $LTB_4$ in BAL fluid measured using an ELISA at the indicated times following OVA challenge. FIG. 1b shows semiquantitative RT-PCR analysis of BLT1 and BLT2. Levels of BLT2 mRNA in the lungs were measured in control (normal), pre-OVA challenged (pre-provocation) and OVA-challenged (OVA provocation) mice. GAPDH was used as quantitative control. FIG. 1c shows images of in situ hybridization of BLT2 mRNA in lung airways. The distributions of BLT2 mRNA in normal (panels i and ii) and OVA-induced asthmatic mouse lung airways (panels iii and iv) are shown (arrows). Data are means±SEM (n=4 in each group). Magnification, 100 (panels i and ii) or 200 (panels iii and iv).

FIG. 2a shows semiquantitative RT-PCR analysis of BLT2 mRNA levels in lung tissue. FIG. 2b is a graph showing quantitative analyses of BLT2 mRNA levels using real-time PCR. FIG. 2c shows histological analysis of lung airways from OVA-challenged mice 48 hr after the last 1% OVA challenge. Lungs were excised, fixed, and stained with HE. Mice were sensitized/challenged with PBS (Normal, panel A), OVA with DMSO pretreatment (OVA/DMSO, panel B), or OVA with LY255283 (2.5 mg/ml) pretreatment (OVA/LY255283, panel C). Scale Bars, 50 μm. FIG. 2d is a graph showing histological scores. The data are means±SEM (n=5 in each group). *P<0.05 vs. OVA/DMSO.

FIG. 3a shows semiquantitative RT-PCR analysis of BLT2 mRNA levels in lung tissue. Normal and OVA-challenged mice (C57BL/6) pretreated with sense (ss) BLT2 (1.6 mg/kg), antisense (as) BLT2 (1.6 mg/kg) or buffer (saline) 24 hr and 1 hr before 10% OVA challenge were sacrificed two days after the last OVA challenge, and their lungs were analyzed for levels of BLT1, BLT2 and control GAPDH mRNAs using semiquantitative RT-PCR analysis. FIG. 3b is a graph showing quantitative analyses of BLT2 mRNA levels using real-time PCR. FIG. 3c are images showing infiltration of eosinophils into BAL. Eosinophils (arrows) in BAL fluid were obtained using cytospin and stained with Diff-Quick. Scale Bars, 50 μm. FIG. 3d depicts histological analysis of lung airways from OVA-challenged mice 48 hr after OVA challenge. Lungs were excised, fixed, and stained with HE. For this experiment, mice were pretreated with sense BLT2 (1.6 mg/kg; panel c), antisense BLT2 (1.6 mg/kg; panel d) or buffer (saline; panel b) before OVA challenge. Normal lung tissue is shown at panel a. Scale Bars, 50 μm.

Data are means±SEM (n=5 in each group). *P<0.05 vs. OVA/ssBLT2; P<0.01 vs. OVA/ssBLT2; *P<0.001 vs. OVA/ssBLT2.

Figure 4A:
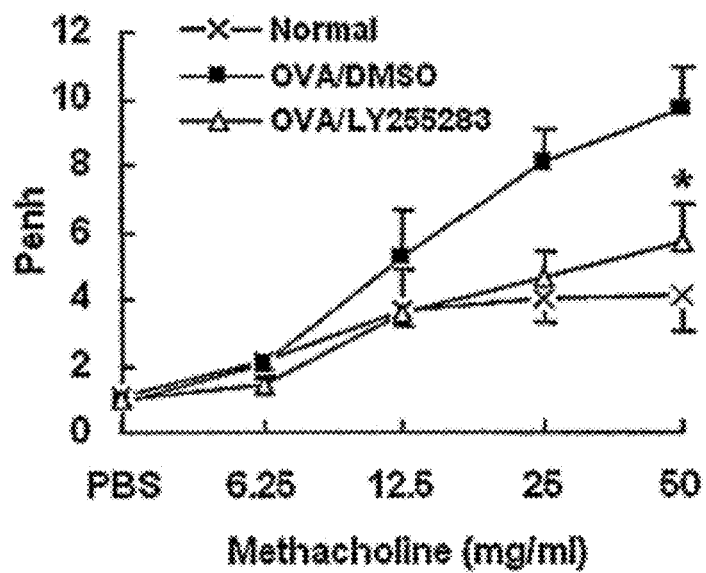
Figure 4B:
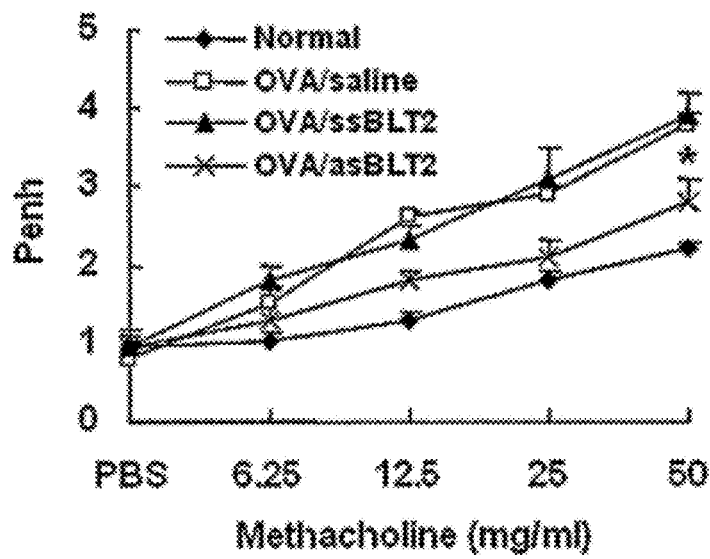

FIGS. 4a-4b show the effect of BLT2 inhibition on AHR. FIG. 4a shows the effect of LY255283 on AHR in OVA-challenged mice. FIG. 4b shows the effect of antisense BLT2 on AHR in OVA-challenged mice. AHR was measured 24 h after the last 1% OVA challenge, after which mice was placed in a chamber and nebulized with increasing doses of methacholine (6.25 mg/ml-50 mg/ml) for 3 min. Data are means±SEM (n=5 in each group). *P<0.05 vs. OVA/DMSO in A or OVA/ssBLT2 in B.

Figure 5A:
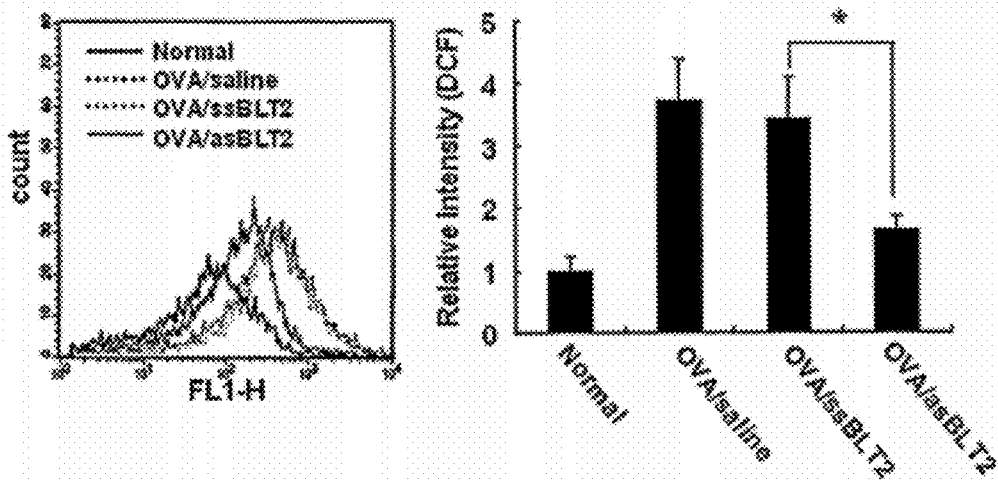
Figure 5B:
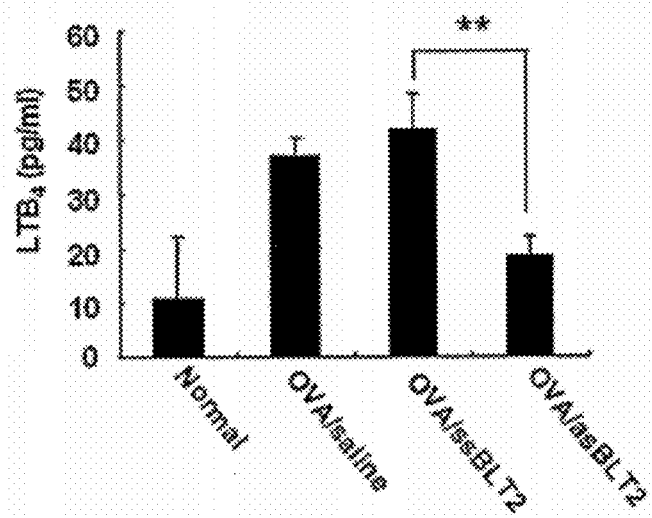

FIGS. 5a-5b show that antisense BLT2 attenuated ROS generation. FIG. 5a depicts FACS analysis of BLT2 expression in cells. BAL fluid was collected 48 h after 10% OVA challenge. Normal and OVA-challenged mice were pretreated with sense BLT2 (1.6 mg/kg), antisense BLT2 (1.6 mg/kg) or buffer (saline) 24 hr and 1 hr before 10% provocation and then sacrificed at 48 hr after the last OVA challenge. The cells present in the BAL fluid were washed and then immediately observed using a FACSCalibur™. FIG. 5b is a graph depicting measurement of $LTB_4$ levels in BAL fluid using a specific ELISA. Normal and OVA-challenged mice were pretreated with sense BLT2 (1.6 mg/kg), antisense BLT2 (1.6 mg/kg) or buffer (saline) 24 h and 1 h before 10% provocation and then sacrificed at 48 h after the last OVA challenge. BAL fluid was then collected for $LTB_4$ analysis. Data are means±SEM (n=5 in each group). *P<0.05 vs. OVA/ssBLT2; **P<0.01 vs. OVA/ssBLT2.

Figure 6A:
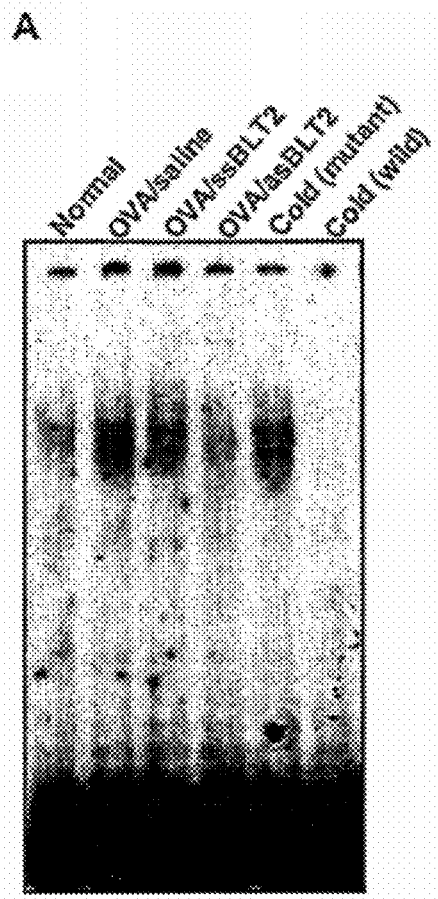
Figure 6B:
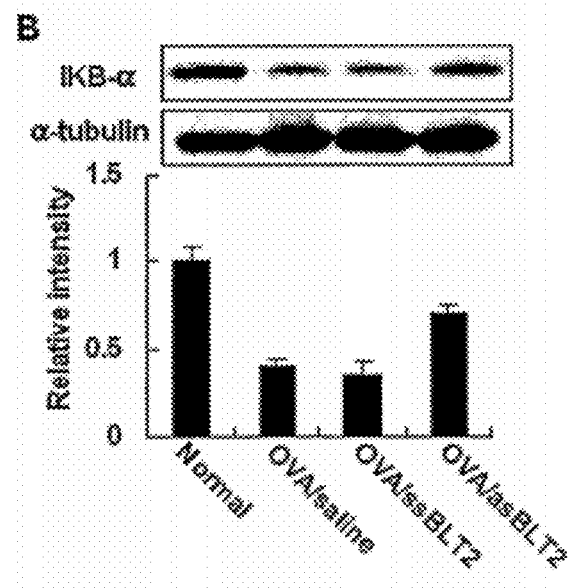
Figure 6C:
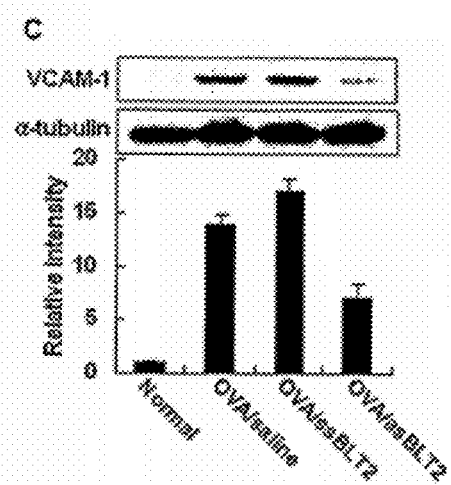
Figure 6D:
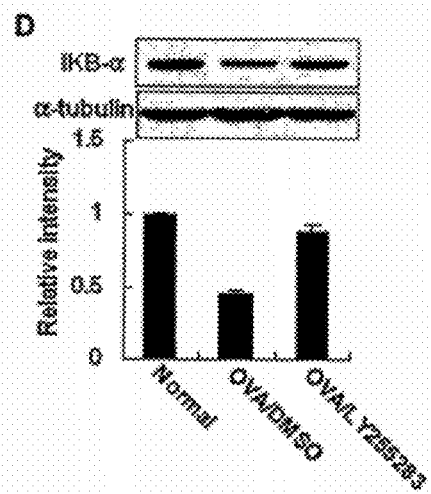
Figure 6E:
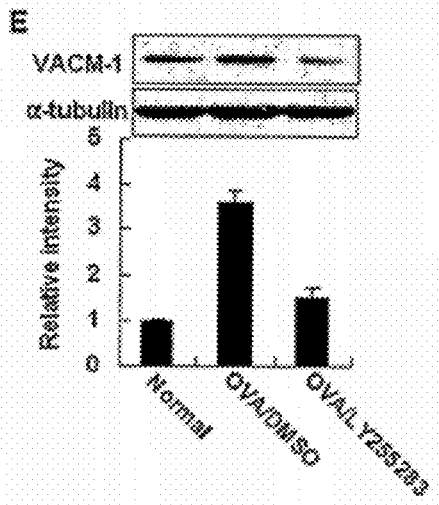

FIGS. 6a-6e show that BLT2 inhibition attenuated NF-κB activation and VCAM-1 expression. FIG. 6a depicts EMSA analysis of NF-κB activation following OVA-challenge. Normal and OVA-challenged mice were pretreated with sense BLT2 (1.6 mg/kg), antisense BLT2 (1.6 mg/kg) or buffer (saline) 24 hr and 1 hr before provocation and then sacrificed two days after the last OVA challenge. Nuclear extracts were then prepared from the lungs and incubated with labeled NF-κB-binding oligonucleotides. FIG. 6b depicts Western blot analysis of IKB-α expression in mouse model of asthma administered with asBLT2. FIG. 6c depicts Western blot analysis of VCAM-1 in mouse model of asthma administered with asBLT2. Lung tissue extracts were prepared from normal mice, OVA-challenged mice (OVA/saline), OVA-challenged mice administered sense BLT2 (1.6 mg/kg) or antisense BLT2 (1.6 mg/kg). Equal amounts of protein were then analyzed by immunoblotting with antibodies against 1κB-α (FIG. 6b) and VCAM-1 (FIG. 6c). Tubulin was used as a loading control. FIG. 6d depicts Western blot analysis of IκB-α expression in mouse model of asthma administered with LY255283. FIG. 6e depicts Western blot analysis of VCAM-1 expression in mouse model of asthma administered with LY255283. Normal and OVA-challenged mice were pretreated with DMSO or LY255283 (2.5 mg/kg) 1 hr before 1% OVA challenge and then sacrificed at 48 hr after the last OVA challenge. Lung tissue extracts were then prepared for Western blotting. Also shown the relative levels of 1κB-α (FIG. 6d) and VCAM-1 (FIG. 6e) obtained using densitometry. The data are means±SEM (n=5 in each group).

Figure 7:
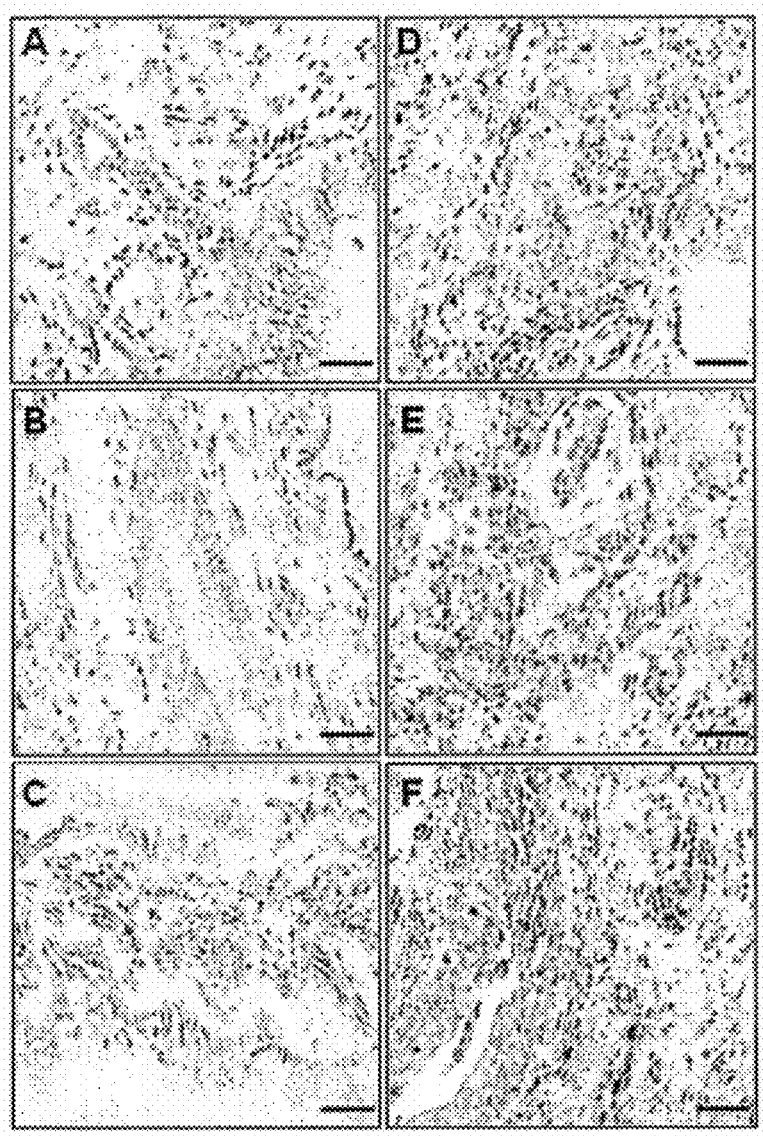
Figure 7:
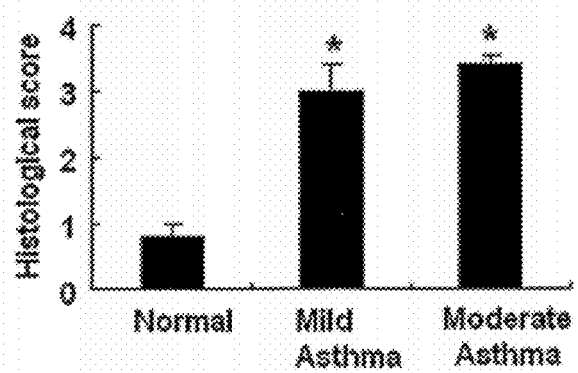
Figure 8A:
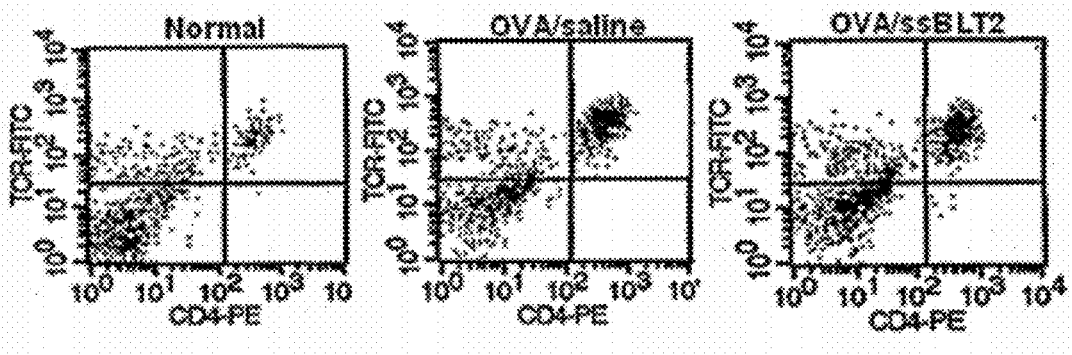
Figure 8A:
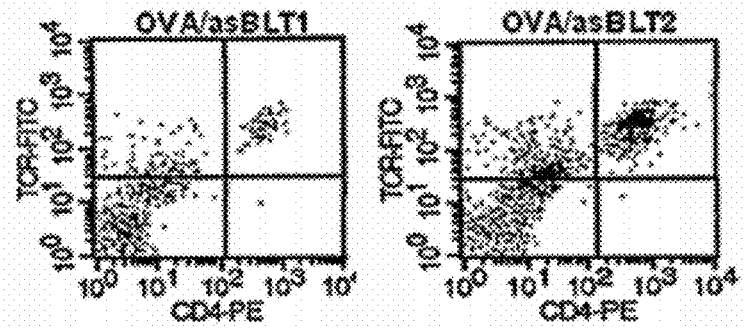
Figure 8A:
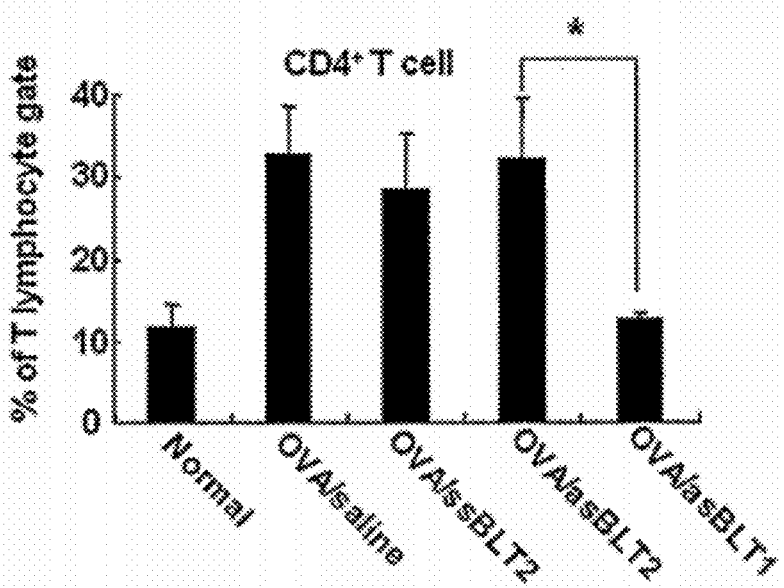
Figure 8B:
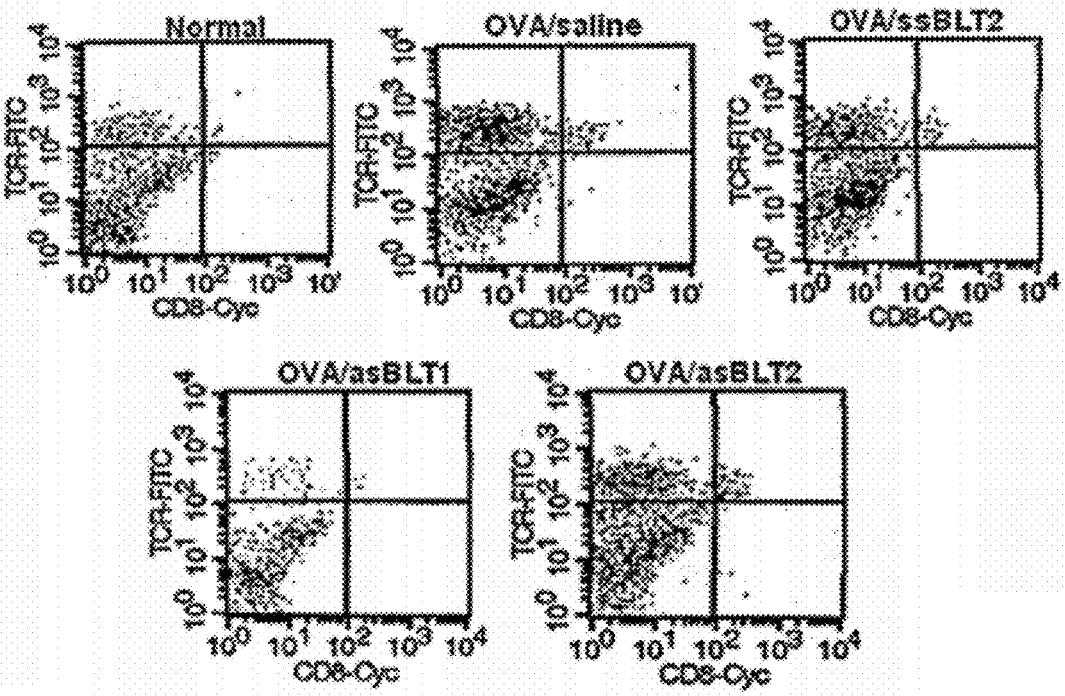
Figure 8B:
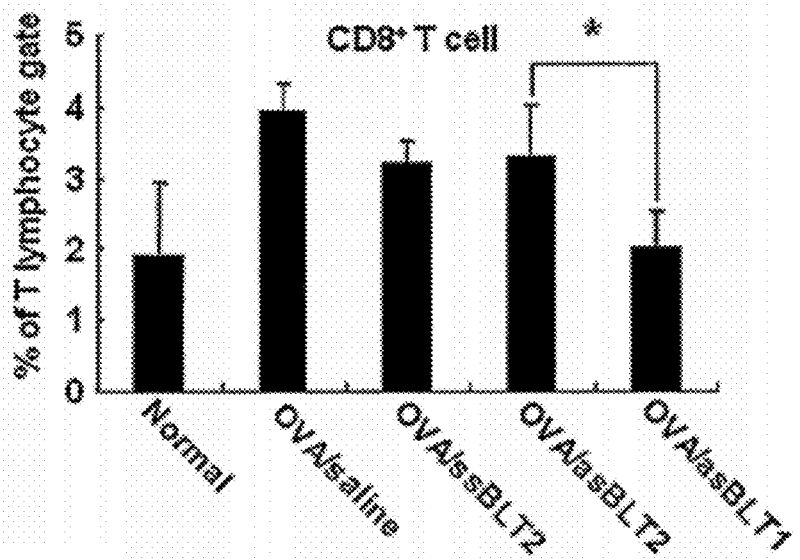

FIG. 7 shows increased expression of BLT2 in bronchial biopsy specimens. Biopsy specimens were obtained from healthy subjects (panels A-C) and subjects with mild (panels D-E) or moderate (panel F) bronchial asthma, after which the patterns of BLT2 expression in sections of mucosa were visualized immunohistochemically. Positive signals were colored red using a streptavidin-alkaline phosphatase system, and the cells were counter-stained using hematoxylin. The images shown are representative of experiments with similar results (n=4 for healthy controls and mild bronchial asthma patients; n=5 for moderate bronchial asthma patients). Scale bars, 50 μm. *P<0.05 vs. Normal FIGS. 8a and 8b show recruitment of T lymphocytes into airways. FIG. 8a depicts FACS analysis showing recruitment of CD4+ T cells into the BAL fluid of mice 12 hr after aerosol OVA challenge. FIG. 8b depicts FACS analysis showing recruitment of CD8+ T cells into the BAL fluid of mice 12 hr after aerosol OVA challenge. BAL fluid was collected 12 hr after 10% OVA challenge and washed with PBS. The leukocytes present were stained with FITC-conjugated anti-mouse TCR chain and PE-cy5 anti-mouse CD8a or PE rat anti-mouse CD4 after blocking with anti-FcRyantibody. Samples were then analyzed by flow cytometry to assess T lymphocyte recruitment. Data are means±SEM (n=6 in each group). *P<0.05 vs. OVA/asBLT2.

Figure 9A:
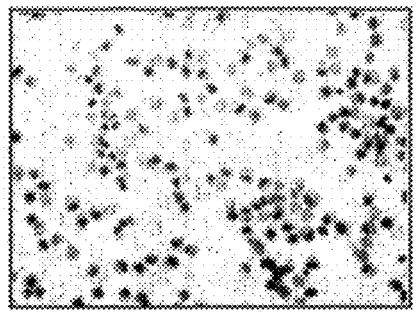
Figure 9A:
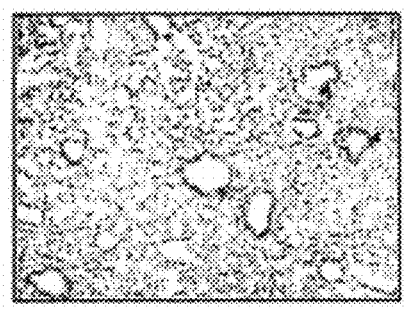
Figure 9A:
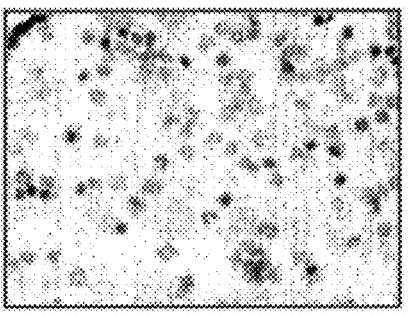
Figure 9A:
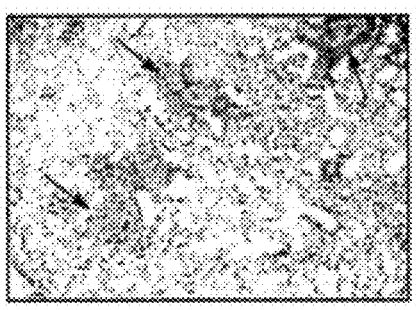
Figure 9A:
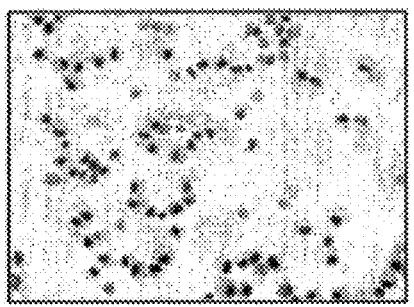
Figure 9A:
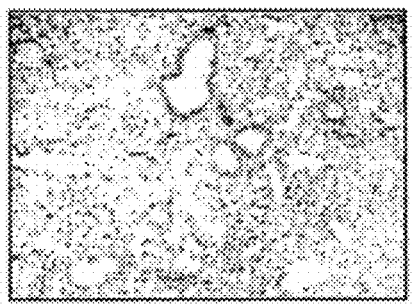
Figure 9A:
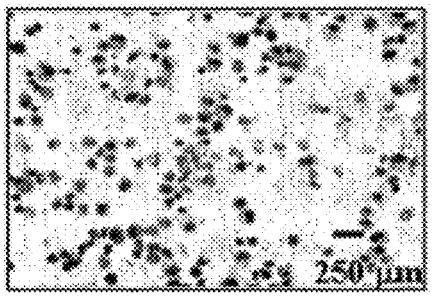
Figure 9A:
Figure 9B:
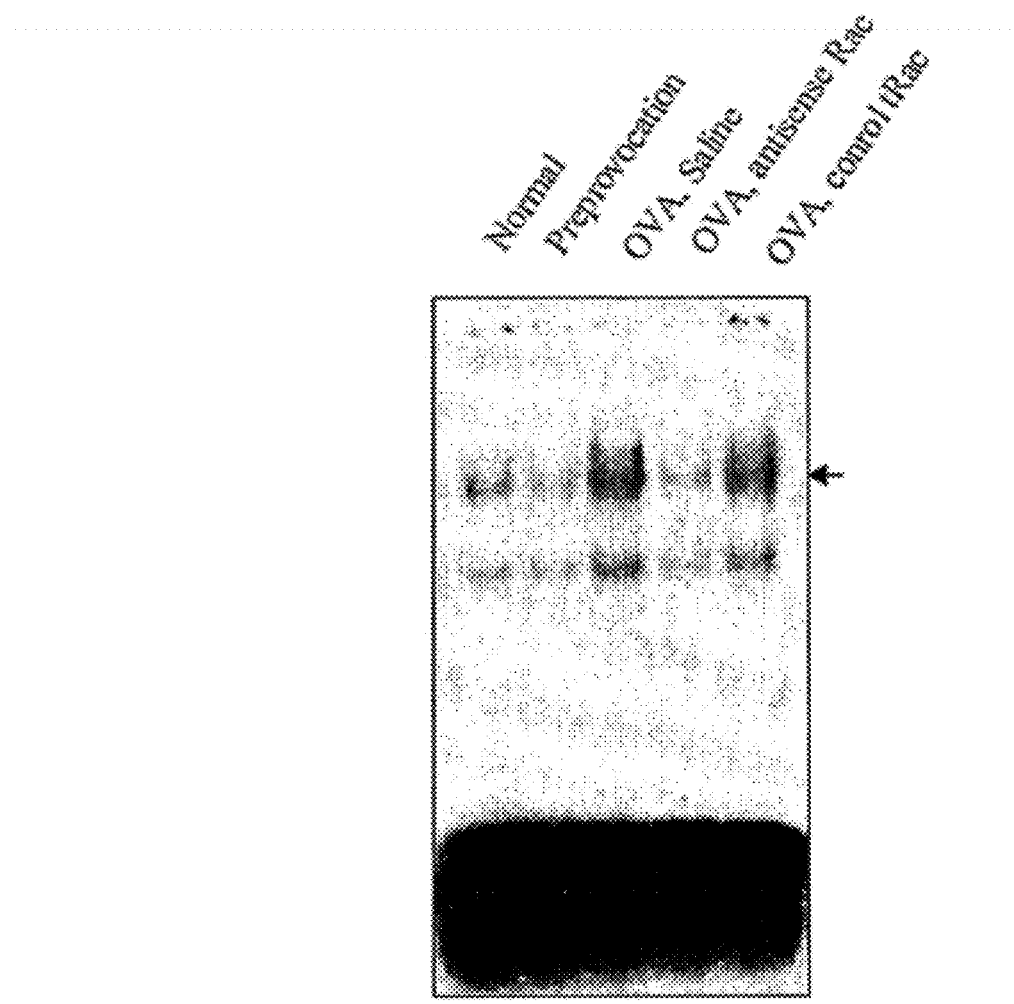

FIGS. 9a-9c shows effect of antisense Rac oligonucleotide treatment on lung inflammation and NF-κB activation. FIG. 9a shows images of lung tissue in mouse model of asthma administered with asRac. To check the involvement of Rac in the process of eosinophil infiltration into the lung airway caused by OVA provocation, antisense oligonucleotides (1.25 mg/kg of weight) were injected into the tail vein of the mice 24 hr and 4 hr before provocation. Forty eight hours after OVA provocation, mice were sacrificed and BAL fluids and lung tissues were obtained. Cells in the BAL fluid were attached to the slide glass and stained with Hemacolour as manufacturer's recommendation. Lung tissues were obtained from normal, buffer, control Rac oligonucleotide (control Rac) or antisense Rac oligonucleotide (asRac) treated mice after OVA provocation. Lung tissues were fixed with 10% formaline, dehydrated and embedded in paraffin. The tissues were cut into 6 μm sections, and stained with Hematoxylin & Eosin. FIG. 9b depicts EMSA analysis of NF-κB in mouse model of asthma administered with asRac. To examine whether OVA provocation induce the NF-κB activity and whether the induced NF-κB is mediated by Rac, electropholetic mobility shift assay (EMSA) was accompanied using antisense Rac oligonucleotide treated mice. Nuclear extracts were purified from the lung tissues and incubated with $^{32}P$-labeled double strand oligonucleotides containing NF-κB binding consensus or mutant sequence at room temperature. DNA-protein complexes were separated by electrophoresis in 6% acrylamide gel under nondenaturing condition, the autoradiography was performed. FIG. 9c depicts Western blot analysis of VCAM-1 expression in mouse model of asthma administered with asRac. To check expression level of VCAM-1, which is known to have critical role in the process of eosinophil transendothelial migration from the blood vessel into the lung parenchyma whole cell lysates were obtained from the lung tissues and Western blot analysis was carried out.

Figure 10A:
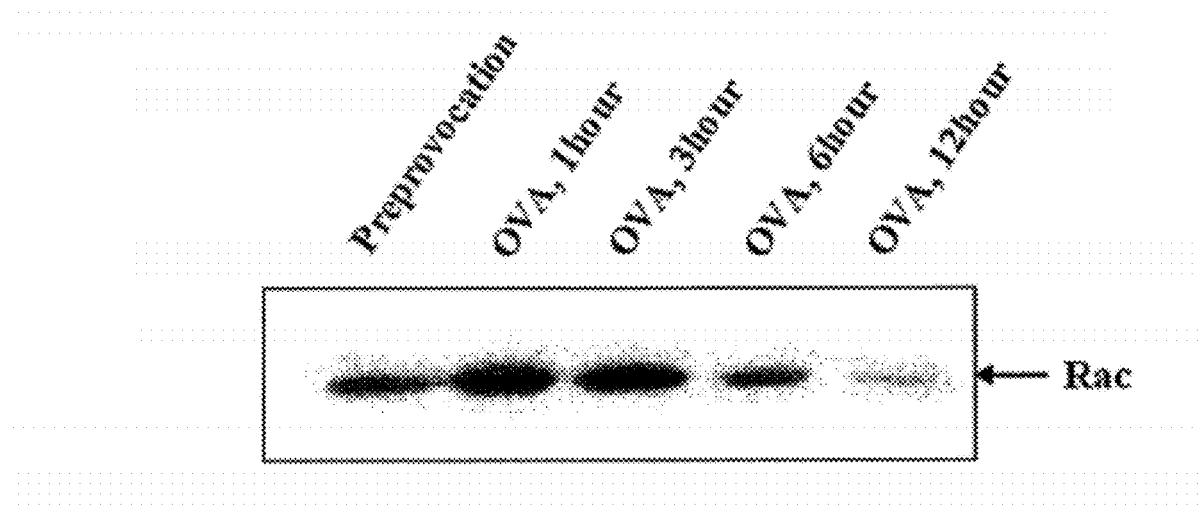
Figure 10B:
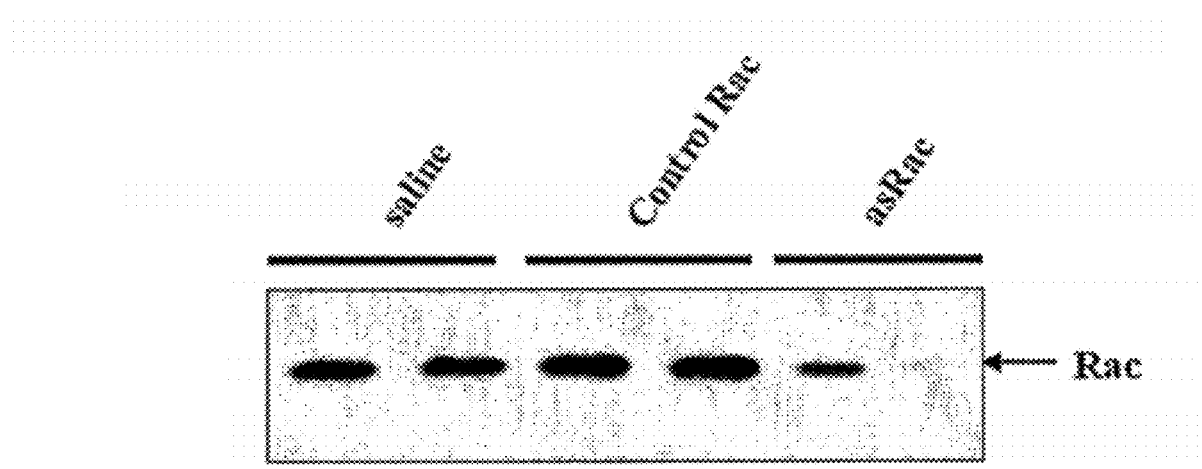

FIGS. 10a and 10b show activation of Rac in the lung tissue by OVA provocation and inhibition of endogenous Rac expression by antisense Rac oligonucleotide treatment. Lung samples were homogenized with micropestle and washed with PBS twice. FIG. 10a depicts Western blot analysis of Rac expression in mouse model of asthma. For membrane protein preparation, cells were suspended in Buffer A and cells were ruptured by passing through 21-G syringe. After ultracentrifugation, protein samples in pelleted membrane fraction were dissolved with buffer A containing 1% Triton X-100. FIG. 10b depicts Western blot analysis of Rac expression in mouse model of asthma administered with asRac. For whole cell lysate preparation, cells from the lung tissues of buffer, control Rac oligonucleotide or antisense Rac oligonucleotide injected mice were suspended with lysis buffer and incubated for 20 min. After centrifugation of the samples, protein quantification was carried out using Bradford reagent and Western blot analysis was performed.

Figure 11A:
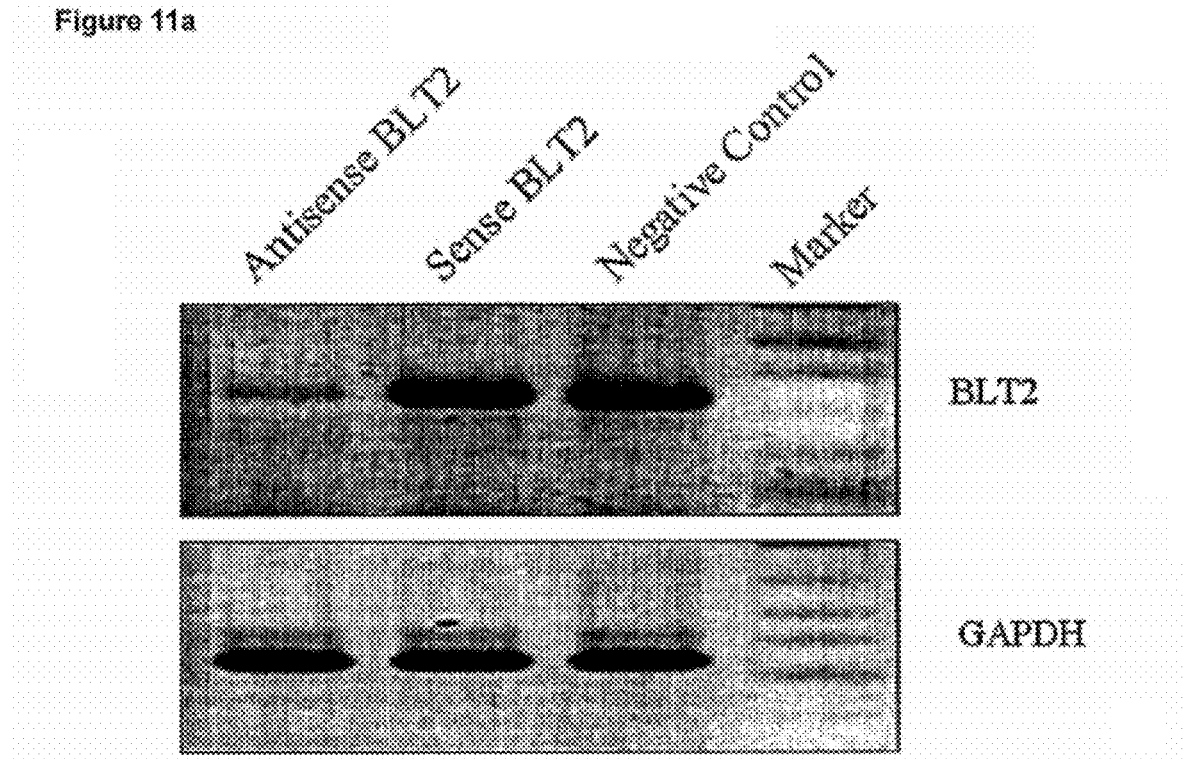
Figure 11B:
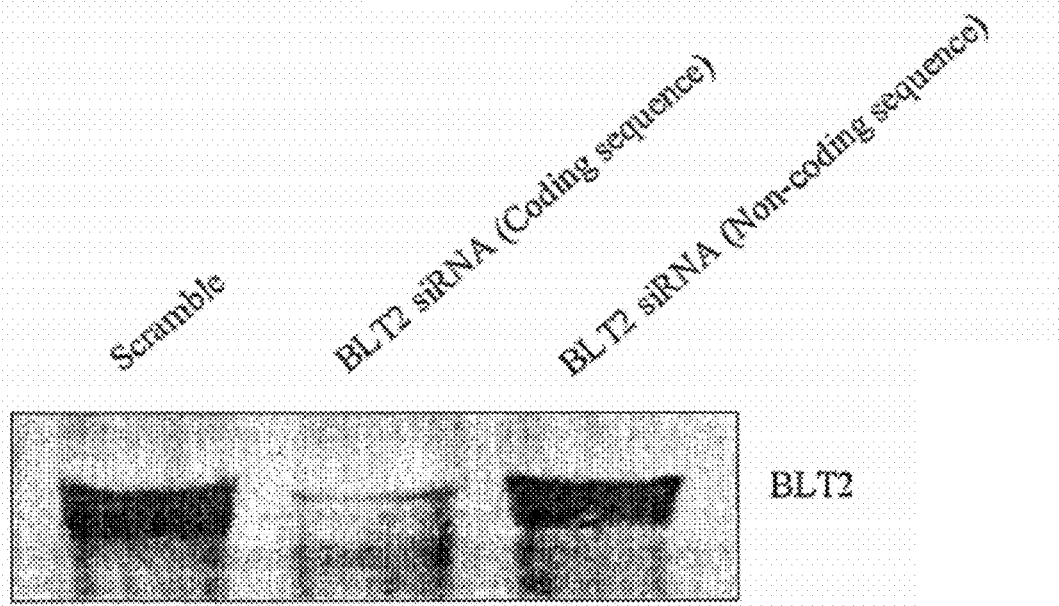

FIG. 11a shows the suppression effect of BLT2 antisense oligonucleotide on BLT2 expression level by RT-PCR. FIG. 11b shows the suppression effect of BLT2 siRNA on BLT2 expression level by Northern blot.

Figure 12:
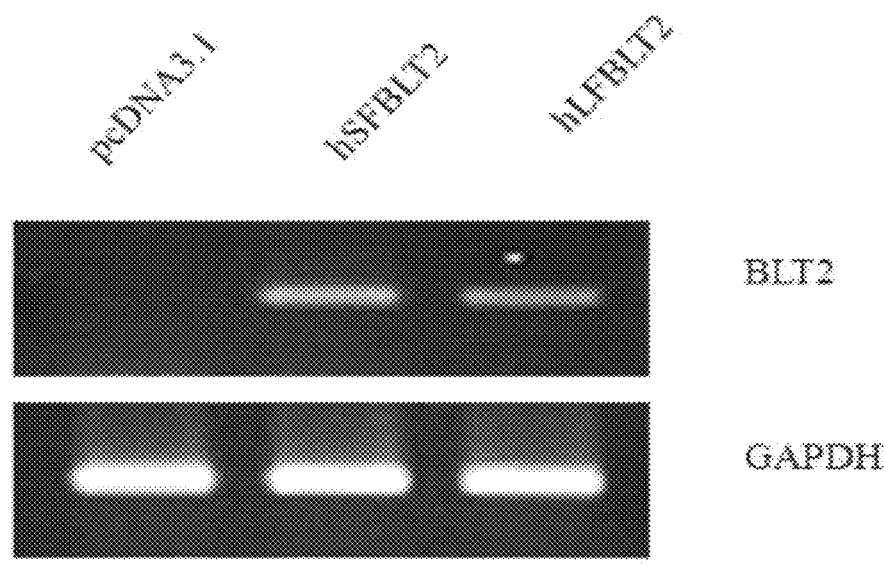
Figure 12:
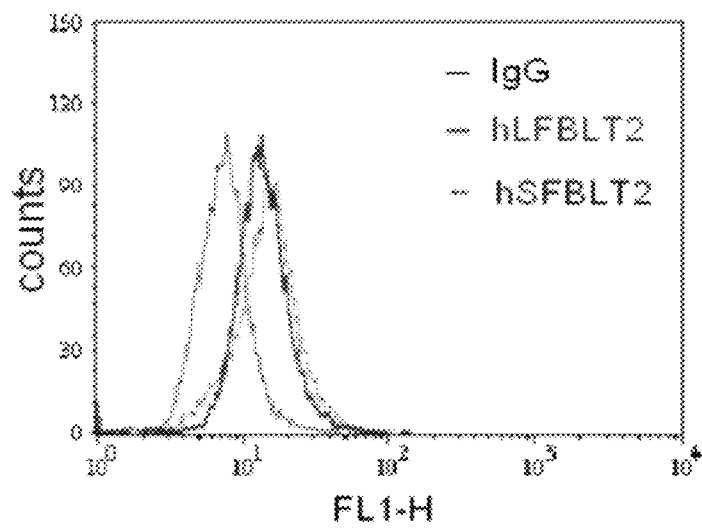

FIGS. 12a and 12b depict similar expression levels of LF-BLT2 or SF-BLT2 when transfected in CHO cells. FIG. 12a depicts RT-PCR analysis showing that LF-BLT2 and SF-BLT2 transcript levels are similar. FIG. 12b is a graph showing that LF-BLT2 or SF-BLT2 protein expression levels were similar as determined by FACS analysis.

Figure 13:
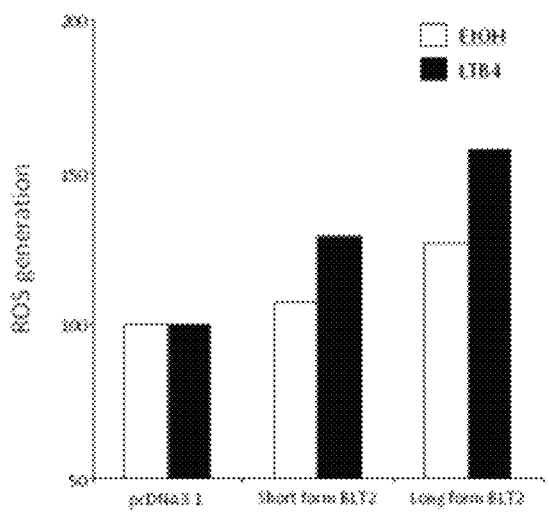
Figure 13:
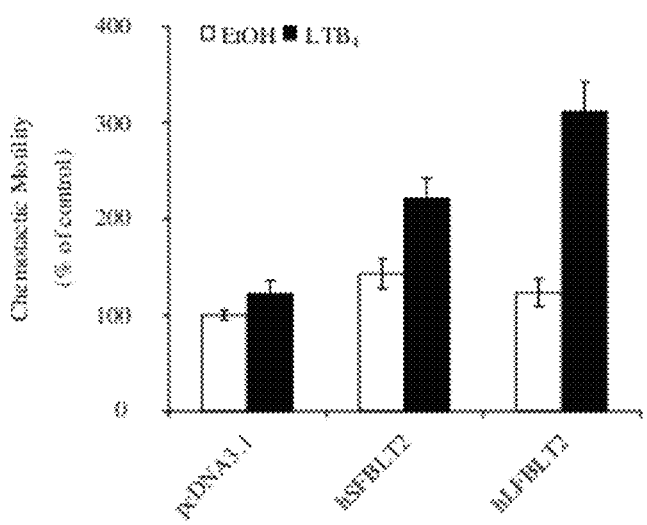

FIGS. 13A and 13B depict that LF-BLT2 is more active in mediating chemotactic signaling and motility in CHO cells compared to SF-BLT2. FIG. 13A is a graph showing enhanced chemotactic motility of LF-BLT2 transfected CHO cells in the presence of $LTB_4$ compared to SF-BLT2 transfected CHO cells. FIG. 13B is a graph showing enhanced ROS generation in LF-BLT2 transfected CHO cells in the presence of $LTB_4$ compared to SF-BLT2 transfected CHO cells.

Figure 14:
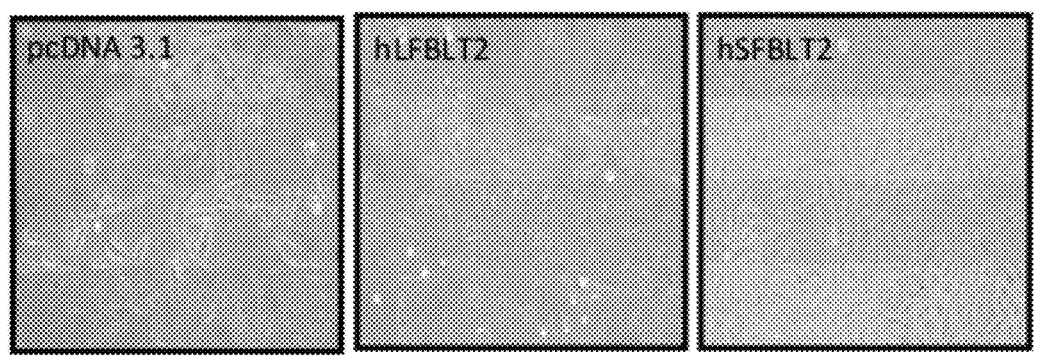
Figure 14:
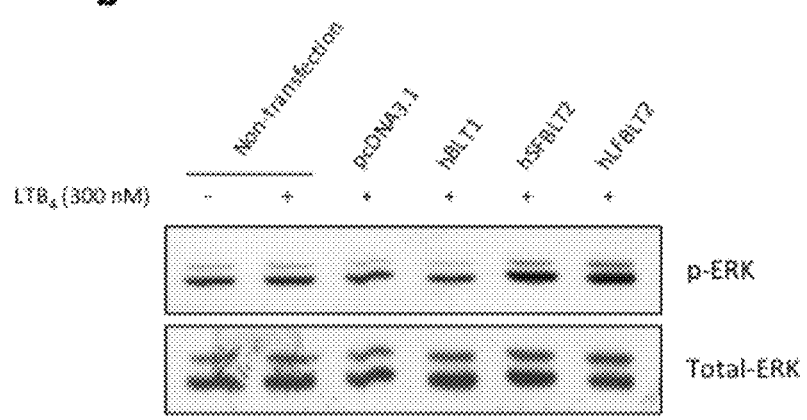

FIGS. 14A and 14B depict that growth and ERK activity were enhanced by LF-BLT2 compared to SF-BLT2. FIG. 14A depicts images of Rat-2 cells transfected with empty vector (left panel), hLFBLT2 construct (middle panel), and hSFBLT2 construct (right panel). FIG. 14B depicts Western blot analysis of ERK in transfected cells, showing that Rat-2 cells transfected with the hLFBLT2 construct had a significantly enhanced ERK activation in the presence of $LTB_4$ compared to Rat-2 cells transfected with the hSF-BLT2 construct.

Figure 15:
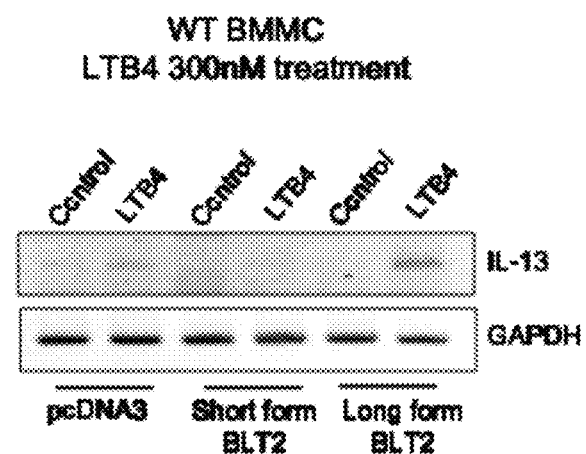

FIG. 15 depicts RT-PCR analysis of IL-13 (top panel) and GADPH (bottom panel) showing that $LTB_4$-evoked IL-13 induction in bone marrow-derived mast cells, indicating a role in allergic response.

Figure 16:
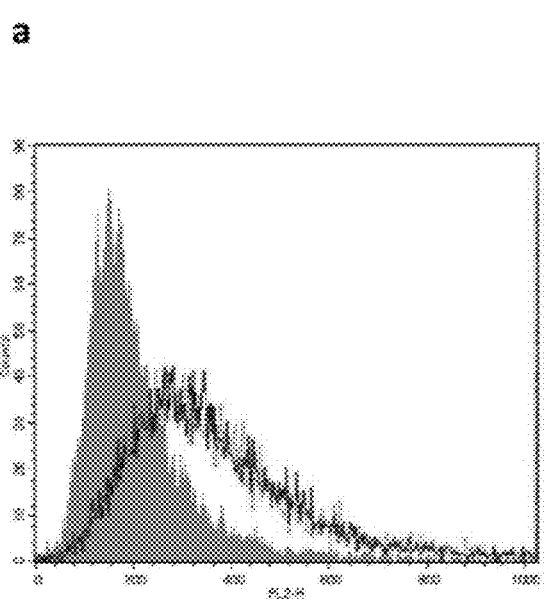

FIGS. 16a and 16b depict the production of antibody to long form BLT2 having BLT neutralizing activity. 253J-BV bladder cancer cells were incubated with FITC-conjugated anti-BLT2 or an isotype control antibody, and BLT2 expression was evaluated by flow cytometry (red and green color). Fluorescence intensity of BLT2 expression level was measured. FIG. 16a depicts representative results of three independent experiments with similar results. FIG. 16b is a chart showing that out of 22 potential candidates, 6 BLT2 (long-form)-recognizing antibodies were selected by FACS analysis. The 6 BLT2-recognizing antibodies are designated in red.

Figure 17:
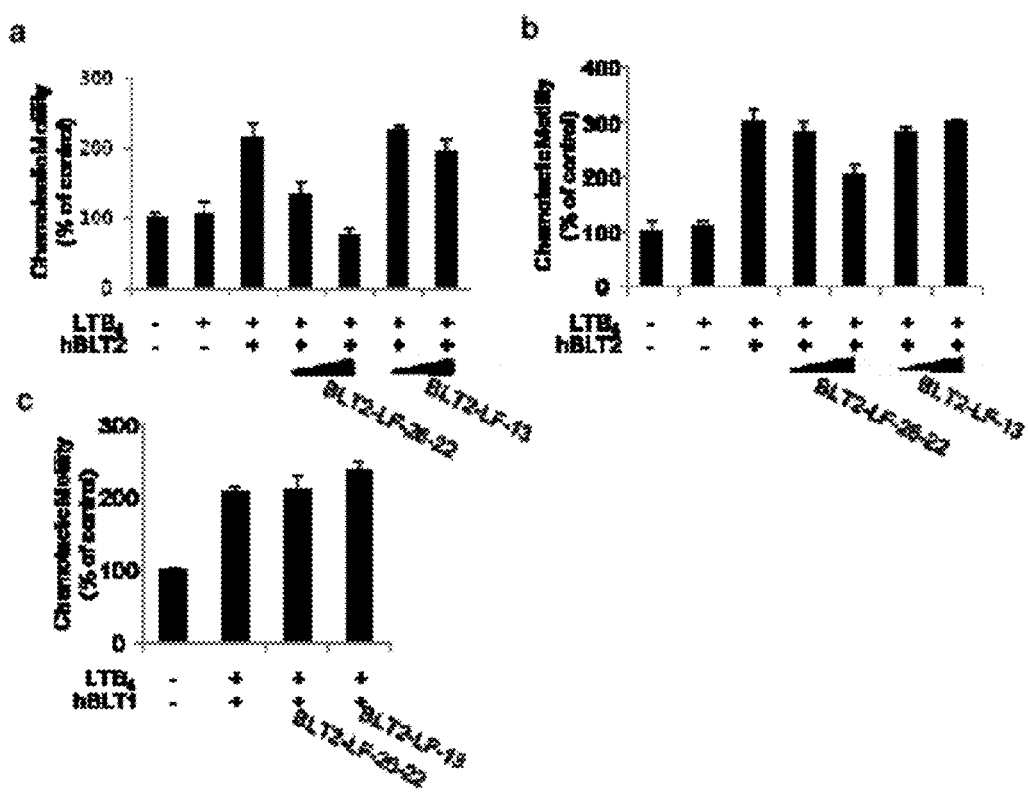

FIGS. 17a-17c are graphs depicting chemotaxis analysis using generated anti-LF BLT2 antibody. FIG. 17a is a graph depicting the effect of anti-LF BLT2 antibody on CHO or CHO-BLT2 stable cells exposed to 300 nM $LTB_4$ for 3 hr. $LTB_4$-induced chemotactic motility was determined in the presence of BLT2 IgG Ab (BLT2-LF-26-22; 10 and 20 μg) and negative antibody control (BLT2-LF-13 IgG Ab; 10 and 20 μg). After migration, cells were fixed and stained with hematoxylin/eosin. FIG. 17b is a graph depicting the effect of anti-LF BLT2 antibody on pcDNA3.1 or BLT2 transfected CHO cells exposed to 300 nM $LTB_4$ for 3 hr. $LTB_4$-induced chemotactic motility was determined in the presence of BLT2 IgG Ab (BLT2-LF-26-22; 10 and 20 μg) or control antibody (BLT2-LF-13 IgG Ab; 10 and 20 μg). After migration, cells were fixed and stained with hematoxylin/eosin. FIG. 17c is a graph showing that BLT1-induced chemotactic migration was not affected by anti-BLT2 Ab (BLT2-LF-26-22), control Ab control (BLT2-LF-13, 20 μg), or pcDNA3.1. The BLT1 transfected CHO cells were exposed to 10 nM $LTB_4$ for 3 hr with BLT2 IgG Ab (BLT2-LF-26-22, 20 μs) and negative IgG Ab control (BLT2-LF-13, 20 μg).

Figure 18:
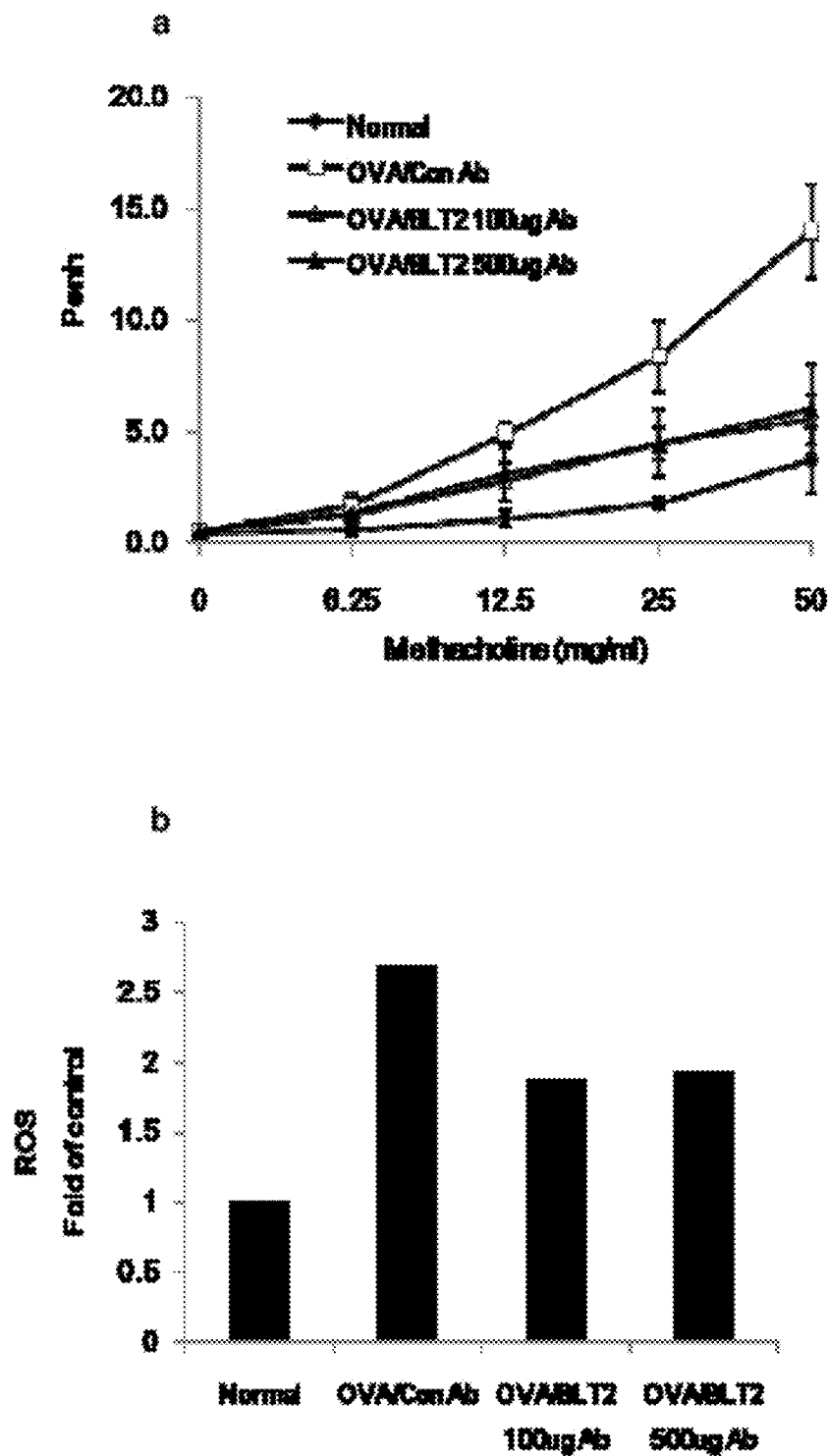

FIGS. 18a and 18b depict AHT inhibition in asthma mouse model assay by anti-LF-BLT2 IgG antibody. FIG. 18a is a graph depicting the effect of BLT2 inhibition on AHR. OVA-challenged mice were pretreated with control antibody (100 μg/mice) and BLT2 IgG Ab (100 μg/mice, 500 μg/mice) 1 hr before 1% OVA challenge and then analyzed at 24 h after the last OVA challenge. FIG. 18b is a graph showing that BLT2 IgG Ab attenuates ROS generation. BALF was collected 48 h after last OVA challenge. OVA-challenged mice were pretreated with control antibody (100 μg/mice), BLT2 IgG Ab (100 μg/mice, 500 μg/mice) 1 hr before 1% OVA challenge and then sacrificed at 48 h after the last OVA challenge. The cells present in the BALF were observed using a FACSCalibur™.

DETAILED DESCRIPTION OF THE INVENTION

The present invention generally features compositions and methods for treating asthma involving inhibitors of leukotriene B4 receptor BLT2, including long form BLT2.

BLT2 is a low-affinity receptor for leukotriene B4 ($LTB_4$), a potent lipid mediator of inflammation generated from arachidonic acid via the 5-lipoxygenase pathway. Unlike BLT1, a high-affinity receptor for $LTB_4$, no physiological role has yet been identified for BLT2, especially with regard to the pathogenesis of asthma. A murine model of allergic asthma was used to evaluate the role of BLT2 in ovalbumin-induced airway inflammation and airway hyperresponsiveness (AHR). The levels of BLT2 mRNA and its ligand $LTB_4$ in the lung airway were highly elevated after OVA challenge, and downregulation of BLT2 with antisense BLT2 oligonucleotides markedly attenuated the airway inflammation and AHR, suggesting a role of BLT2 in the asthmatic response. Further analysis aimed at identifying mediators downstream of BLT2 revealed that BLT2 activation led to elevation of reactive oxygen species (ROS) and subsequent activation of NF-κB, thus inducing the expression of VCAM-1 that is known to be involved in eosinophil infiltration into lung airway. Together the findings suggest that BLT2 plays a pivotal role in the pathogenesis of asthma, acting through a 'ROS-NF-κB'-linked signaling pathway. Finally, immunohistochemical assay of clinical subjects demonstrated that BLT2 expression was high in the airway epithelial layers as well as the microvascular endothelium, as in the murine model of asthma.

According to one aspect of the present invention, there is provided a use of a substance that inhibits the expression or intracellular signaling of BLT2 for the manufacture of a medicament for the treatment of asthma. In this specification, the phrase "inhibit(s) the expression of BLT2" means to inhibit any step among the transcription, mRNA processing, translation, translocation, and maturation of BLT2, and the phrase "inhibit(s) the intracellular signaling of BLT2" means to inhibit any step among the binding of $LTB_4$ to BLT2, the activation of BLT2 and its intracellular signaling pathway to induce asthma.

The nucleotide sequence of human BLT2 gene is available at the NCBI (NM_019839.2) and denoted as SEQ ID NO: 1 in this specification. The BLT2 gene has 2 kinds of CDS form, long form CDS (1618-2787) and short form CDS (1711-2787), the nucleotide sequences of which are denoted as SEQ ID NO: 2 and SEQ ID NO: 4, respectively. The amino acid sequence of the long form BLT2 protein is available at the NCBI (NP_062813.1) and is denoted as SEQ ID NO: 3. The amino acid sequence of the short form BLT2 protein is available at the NCBI (AB029892) and is denoted as SEQ ID NO: 5.

In a preferred embodiment, the substance may be an antibody to BLT2 (e.g., long form BLT2). The antibody to BLT2 inhibits the intracellular signaling of BLT2. The antibody binds to BLT2 competitively with $LTB_4$, so that can inhibit the intracellular signaling of BLT2. The antibody can be produced according to the conventional methods for producing polyclonal or monoclonal antibody by using BLT2 or its fragment as an antigen.

In a preferred embodiment, the substance may be a compound that binds to BLT2 and inhibits the intracellular signaling of BLT2. The compound is also referred to as BLT2 antagonist, which means a compound that antagonizes an action of $LTB_4$ on BLT2. The compound can be screened according to the present screening method from the commercially available chemical DB.

Figure 1A:
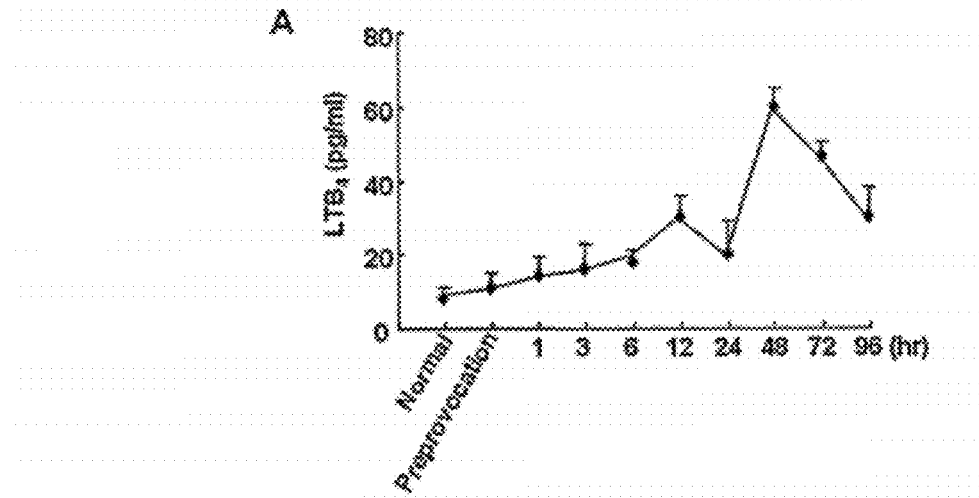
FIGS. 1a-1c show the increased expression of BLT2 mRNA in an OVA-induced murine asthma model.

In a preferred embodiment, the compound may be LY255283 (1-[5-ethyl-2-hydroxy-4-[[6-methyl-6-(1H-tetrazol-5-yl)heptyl]oxy]phenyl]-ethanone). FIG. 1a shows a chemical structure of LY255283. LY255283 is a competitive antagonist of the BLT2 receptor. LY255283 have been known to inhibit eosinophil chemotaxis by 80% at a concentration of 10 μM, and inhibits the binding of radiolabeled $LTB_4$ to eosinophil membranes with an IC50 of 260 nM [Ann N Y Acad Sci 629 274-287 (1991)]. Also, LY255283 have been known to be a novel leukotriene B4 receptor antagonist, which limits activation of neutrophils and prevents acute lung injury induced by endotoxin in pigs [Surgery. 1993 August; 114(2):191-8]. However, the anti-asthma activity of LY25583 was revealed by the present inventors for the first time.

In a preferred embodiment, the substance may be an antisense or siRNA oligonucleotide that inhibits the expression of BLT2. The antisense or siRNA oligonucleotide has a nucleotide sequence complementary to the nucleotide sequence of BLT2 mRNA as set forth in SEQ ID NO: 2.

The term "antisense oligonucleotide" used herein is intended to refer to nucleic acids, preferably, DNA, RNA or its derivatives, that are complementary to the nucleotide sequences of a target mRNA, characterized in that they binds to the target mRNA and interfere its translation to protein. The antisense oligonucleotide of this invention means DNA or RNA sequences complementary and binding to BLT2 mRNA, that are able to inhibit translation, translocation, maturation or other biological functions of BLT2 mRNA. The antisense nucleic acid is 6-100, preferably, 8-60, more preferably, 10-40 nucleotides in length.

The antisense oligonucleotide may comprise at lease one modification in its base, sugar or backbone for its higher inhibition efficacy (De Mesmaeker et al., Curr Opin Struct Biol., 5(3):343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 86:6553 (1989)), cholic acid (Manoharan et al. Bioorg. Med. Chem. Let, 4:1053 (1994)), a thioether, e.g., hexyl-5-tritylthiol (Manoharan et al. Ann. N.Y. Acad. ScL, 660:306 (1992); Manoharan et al. Bioorg. Med. Chem. Let, 3: 2765 (1993)), a thiocholesterol (Oberhauser et al., Nucl. Acids Res., 20:533 (1992)), an aliphatic chain, e.g., dodecandiol or undecyl residues (Saison-Behmoaras et al. EMBO J., 10:111 (1991); Kabanov et al. FEBS Lett, 259:327 (1990); Svinarchuk et al. Biochimie, 75:49 (1993), a phospholipid, e.g., di-hexadecyl-rac-glycerol or triethylammonium 1,2-di-O-hexadecyl-rac-glycero-3-H-phosphonate (Manoharan et al. Tetrahedron Lett, 36:3651 (1995); Shea et al. Nucl. Acids Res., 18:3777 (1990)), a polyamine or a polyethylene glycol chain (Manoharan et al. Nucleosides & Nucleotides, 14:969 (1995)), or adamantane acetic acid (Manoharan et al. Tetrahedron Lett., 36: 3651 (1995)). Oligonucleotides comprising lipophilic moieties, and methods for preparing such oligonucleotides are known in the art, for example, U.S. Pat. Nos. 5,138,045, 5,218,105 and 5,459,255. The modifications described above enhance stability against nuclease degradation and increase affinity of the antisense oligonucleotide toward its target mRNA.

The antisense molecule is conventionally synthesized in vitro and then transmitted to cells. In addition, it is intracellular produced by transcription from foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to peptide.

According to a preferred embodiment, the antisense oligonucleotide may have a nucleotide sequence of SEQ ID NO: 6, which is complementary to the target region (1738-1752) of SEQ ID NO: 2.

According to a preferred embodiment, the siRNA oligonucleotide may have a sense sequence of SEQ ID NO: 7 and an antisense sequence of SEQ ID NO: 8, which is complementary to the target region (1705-1724) of SEQ ID NO: 2.

The term "siRNA" used herein refers to a nucleic acid molecule mediating RNA interference or gene silencing (see WO 00/44895, WO 01/36646, WO 99/32619, WO 01/29058, WO 99/07409 and WO 00/44914). The siRNA to inhibit expression of a target gene provides effective gene knockdown method or gene therapy method. It was been first in plants, insects, Drosophila melanogaster and parasites and recently has been used for mammalian cell researches.

The siRNA molecule of this invention may consist of a sense RNA strand (having sequence corresponding to BLT2 mRNA) and an antisense RNA strand (having sequence complementary to BLT2 mRNA) and form a duplex structure. Alternatively, the siRNA molecule of this invention may have a single strand structure comprising self-complementary sense and antisense strands.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably, 15-80 nucleotides, and more preferably, 20-70 nucleotides. The siRNA may comprise either blunt or cohesive end so long as it enables to silent the BLT2 expression due to RNAi effect. The cohesive end may be prepared in 3'-end overhanging structure or 5'-end overhanging structure.

The siRNA may be constructed by inserting a short nucleotide sequence (e.g., about 5-15 nt) between self-complementary sense and antisense strands. The siRNA expressed forms a hairpin structure by intramolecular hybridization, resulting in the formation of stem-and-loop structure. The stem-and-loop structure is processed in vitro or in vivo to generate active siRNA molecule mediating RNAi.

In a preferred embodiment, the substance may be a compound that inhibits the upstream or downstream signaling pathway of BLT2. In certain embodiments, a compound of the invention can prevent, inhibit, or disrupt, or reduce by at least 10%, 25%, 50%, 75%, or 100% the activity of a BLT2 pathway by binding to BLT, e.g., long-form BLT2. An anti-asthma therapeutic, such as antibody against long-form BLT2, may be administered in combination with any other standard therapy or conventional agent for treating asthma; such methods are known to the skilled artisan and described in Remington's Pharmaceutical Sciences by E. W. Martin.

In the preferred embodiment, the asthma may be characterized by that BLT2 protein is over-expressed in the lung airway. The present inventors have found that BLT2 protein and its ligand $LTB_4$ were over-expressed in the lung airway after OVA challenge, and downregulation of BLT2 with antisense BLT2 oligonucleotides markedly attenuated the airway inflammation and AHR. Therefore, any anti-asthma therapy strategy based on the inhibition of BLT2 overexpression is claimed as the present invention.

In the preferred embodiment, the over-expression, i.e. activation of BLT2 may cause asthmatic symptoms by elevating ROS generation and subsequent NF-KB activation. The present inventors demonstrated that the BLT2 activation led to elevation of reactive oxygen species (ROS) and subsequent activation of NF-κB, thus inducing the expression of VCAM-1 that is known to be involved in eosinophil infiltration into lung airway.

In the preferred embodiment, the treatment of asthma may be accomplished by reducing eosinophil infiltration into lung airway, airway inflammation and airway hyperresponsiveness (AHR). Therefore, any use of BLT2 inhibitors as a therapeutic composition against asthma is claimed in the present invention.

According to another aspect of the present invention, there is provided a use of a combination of (a) a substance that inhibits the expression or intracellular signaling of BLT2, and (b) other anti-asthma drugs for the manufacture of a medicament for the treatment of asthma. According to another aspect of the present invention, there is provided a use of a substance that inhibits the expression or activity of Rac for the manufacture of a medicament for the treatment of asthma. In this specification, the phrase "inhibit(s) the expression of Rac" means to inhibit any step among the transcription, mRNA processing, translation, translocation, and maturation of Rac, and the phrase "inhibit(s) the activity of Rac" means to inhibit any step among the GTPase activity of Rac and its intracellular signaling pathway to induce asthma.

Rac, a member of Rho family GTPases, mediates various cellular responses such as actin polymerization, cell proliferation, cPLA2 activation, and generation of reactive oxygen species (ROS). A mouse model system for asthma was used to determine the role of Rac1 on allergen-induced bronchial inflammation and airway hyperresponsiveness (AHR). Rac1 activity is dramatically stimulated after allergen challenge and administration of antisense oligomers to Rac1 remarkably reduced bronchial inflammation and AHR. In a further study to determine the signaling mechanism by which Rac1 mediates asthmatic inflammation and AHR, Rac1 was important for the NFkB activation critically implicated in the transcription of various inflammatory genes such as VCAM-1. Additionally, Rac1 was shown to mediate the activation of cPLA2, which catalyzes the hydrolysis of membrane phospholipids leading to the release of arachidonic acid (AA) and subsequently eicosanoids such as leukotrienes (LTs). Together, these findings indicate that Rad is critically involved in the pathogenesis of the bronchial asthma. In the preferred embodiment, the substance may be an antisense or siRNA oligonucleotide that inhibits the expression of Rac. The antisense or siRNA oligonucleotide has a nucleotide sequence complementary to the nucleotide sequence of Rac mRNA as set forth in SEQ ID NO: 13. The sequence of mRNA or CDS of human Rac gene is available at the NCBI (gi: 156071511) and its deduced amino acid sequence is denoted as SEQ ID NO: 14.

According to another aspect of the present invention, there is provided a pharmaceutical composition for the treatment of asthma, which comprises a substance that inhibits the expression or intracellular signaling of BLT2 as an active ingredient. In the pharmaceutical composition of the present invention, the substance may be chemical compounds, peptides, antibody proteins, nucleotides, antisense oligonucleotides, siRNA oligonucleotides or extract of natural source. The present pharmaceutical composition may comprise a pharmaceutically acceptable carrier in addition.

According to another aspect of the present invention, there is provided a pharmaceutical composition for the treatment of asthma, which comprises a substance that inhibits the expression or activity of Rac as an active ingredient. In the pharmaceutical composition of the present invention, the substance may be chemical compounds, peptides, antibody proteins, nucleotides, antisense oligonucleotides, siRNA oligonucleotides or extract of natural source. The present pharmaceutical composition may comprise a pharmaceutically acceptable carrier in addition.

According to another aspect of the present invention, there is provided a method for treating a patient with asthma, which comprises administering a therapeutically effective amount of a substance that inhibits the expression or intracellular signaling of BLT2 to the patient. According to another aspect of the present invention, there is provided a method for treating a patient with asthma, which comprises administering a therapeutically effective amount of a substance that inhibits the expression or activity of Rac to the patient.

According to another aspect of the present invention, there is provided a method for screening a substance for treating asthma, which comprises the steps of: (a) contacting the substance to be analyzed to a cell containing BLT2 gene or protein; and, (b) measuring the expression or intracellular signaling level of BLT2, wherein if the expression or intracellular signaling level of BLT2 is down-regulated, the substance is determined to have a potency to treat asthma.

According to the present method, the cell containing the BLT2 gene or protein can be easily prepared by obtaining cells containing their original BLT2 gene or by transfecting cells with a foreign BLT 2 gene. The cells containing the BLT2 gene or protein are first contacted to substances to be analyzed. The term "substance" used herein in conjunction with the present screening method refers to a material tested in the present method for analyzing the influence on the expression level of the BLT2 gene, the amount of the BLT2 protein or the intracellular signaling level of the BLT2 receptor. The substance includes chemical compounds, peptides, antibody proteins, nucleotides, antisense-RNA, siRNA (small interference RNA) and extract of natural source, but not limited to.

Afterwards, the expression level of the BLT2 gene, the amount of the BLT2 protein or the intracellular signaling level of the BLT2 receptor in cells is measured. Where the expression level of the BLT2 gene, the amount of the BLT2 protein or the intracellular signaling level of the BLT2 receptor is measured to be down-regulated, the substance is determined to be a candidate to treat asthma.

The measurement of the expression level of the BLT2 gene could be carried out by a variety of methods known in the art. For example, RT-PCR (Sambrook et al., Molecular Cloning. A Laboratory Manual, 3rd ed. Cold Spring Harbor Press (2001)), Northern blotting (Peter B. Kaufma et al., Molecular and Cellular Methods in Biology and Medicine, 102-108, CRC press), hybridization using cDNA microarray (Sambrook et al., Molecular Cloning. A Laboratory Manual, 3rd ed. Cold Spring Harbor Press (2001)) and in situ hybridization (Sambrook et al., Molecular Cloning. A Laboratory Manual, 3rd ed. Cold Spring Harbor Press (2001)) may be used. Where the expression level of the BLT2 gene is analyzed by RT-PCT, total RNA is first isolated from cells treated with a substance to be analyzed and a first cDNA strand is then synthesized using oligo dT primer and reverse transcriptase. Then, PCR amplifications are performed using the first cDNA strand as templates and a BI_T2-specific primer set. Finally, the PCR amplified products are resolved by electrophoresis and bands are analyzed for assessing the expression level of the BLT2 gene.

The amount of the BLT2 protein may be determined by various immunoassays known in the art. For example, radioimmunoassay, radioimmuno-precipitation, enzyme-linked immunosorbent assay (ELISA), capture-ELISA, inhibition or competition assay and sandwich assay are used for analyzing the amount of the BLT2 protein.

The intracellular signaling level of the BLT2 receptor may be determined by monitoring an event induced by $LTB_4$, e.g., monitoring the rise of the intracellular calcium concentration as described in example using BLT2-expressing cells etc. (e.g., BLT2 overexpressing cells etc.). For example, if the substance reduces the intracellular calcium concentration by $LTB_4$ in BLT2-expressing cells, it can be judged as BLT2 antagonist.

According to another aspect of the present invention, there is provided a method for screening a substance for treating asthma, which comprises the steps of: (a) contacting the substance to be analyzed to a cell containing Rac gene or protein; and, (b) measuring the expression or activity level of Rac, wherein if the expression or activity level of Rac is down-regulated, the substance is determined to have a potency to treat asthma.

According to another aspect of the present invention, there is provided a kit for detecting asthma, which comprises a primer or probe having a nucleotide sequence complementary to the nucleotide sequence of BLT2 as set forth in SEQ ID NO: 2. Therefore, any methodology or kit developed based on the information that BLT2 overexpression is detected in the lung airway of a patient with asthma may be included in the present invention.

The probes or primers used in the present kit has a complementary sequence to the nucleotide sequence of the BLT2 gene. The term "complementary" with reference to sequence used herein refers to a sequence having complementarity to the extent that the sequence anneals or hybridizes specifically with the nucleotide sequence of the BLT2 gene under certain annealing or hybridization conditions. In this regard, the term "complementary" used herein has different meaning from the term "perfectly complementary". The probes or primers used in the present invention can be one or more mismatch, so long as such mismatches are not sufficient to completely preclude specific annealing or hybridization to the BLT2 gene.

As used herein the term "probe" means a linear oligomer of natural or modified monomers or linkages, including deoxyribonucleotides and ribonucleotides, capable of specifically binding to a target polynucleotide. The probe may be naturally occurring or artificially synthesized. The probe is preferably single stranded. Preferably, the probes used in the present invention are oligodeoxyribonucleotides. The probe of this invention can be comprised of naturally occurring dNMP (i.e., dAMP, dGM, dCMP and dTMP), modified nucleotide, or non-natural nucleotide. The primer can also include ribonucleotides. For instance, the probes of this invention may include nucleotides with backbone modifications such as peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl RNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The suitable length of primers will depend on many factors, including temperature, application and source of primer, generally, 15-30 nucleotides in length. Shorter primers generally need lower temperature to form stable hybridization duplexes to templates.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the BLT2 gene as templates; it is sufficient that they have complementarity to the extent that they anneals specifically to the nucleotide sequence of the BLT2 gene for acting as a point of initiation of synthesis. The primer design may be conveniently performed with referring to the BLT2 gDNA or cDNA sequences, preferably, cDNA sequence. For instance, the primer design may be carried out using computer programs for primer design (e.g., PRIMER 3 program). Exemplified primers of this invention is set forth in SEQ ID NO: 9 (sense primer) and SEQ ID NO: 10 (antisense primer).

According to a preferred embodiment, the diagnosis or detection kit for asthma comprising probes is in the form of microarray, more preferably DNA or cDNA microarray, most preferably cDNA microarray.

In microarray, the present probes serve as hybridizable array elements and are immobilized on substrates. A preferable substrate includes suitable solid or semisolid supporters, such as membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxi compound or aldehyde group or to a polylysin-coated surface. Further, the hybridizable array elements are bound to a substrate through linkers (e.g. ethylene glycol oligomer and diamine).

DNAs to be examined with a microarry of this invention may be labeled, and hybridized with array elements on microarray. Various hybridization conditions are applicable, and for the detection and analysis of the extent of hybridization, various methods are available depending on labels used.

The present method for diagnosing rheumatoid arthritis may be carried out in accordance with hybridization. For such analysis, probes, which have a complementary sequence to the nucleotide sequence of the BLT2 gene, are used.

Using probes hybridizable with the BLT2 gene or cDNA, preferably cDNA, asthma is diagnosed or detected by hybridization-based assay. According to a preferred embodiment, some modifications in the probes of this invention can be made unless the modifications abolish the advantages of the probes. Such modifications, i.e., labels linking to the probes generate a signal to detect hybridization. Suitable labels include fluorophores (e.g., fluorescein), phycoerythrin, rhodamine, lissamine, Cy3 and Cy5 (Pharmacia), chromophores, chemiluminescers, magnetic particles, radioisotopes (e.g., $P^{32}$ and $S^{35}$), mass labels, electron dense particles, enzymes (e.g., alkaline phosphatase and horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, Methods in Enzymology, 65:499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample (preferably, cDNA) to be analyzed may be prepared using mRNA from various biosamples. The biosample is preferably a cell from airway epithelium. Instead of probes, cDNA may be labeled for hybridization-based analysis.

Probes are hybridized with cDNA molecules under stringent conditions for detecting asthma. Suitable hybridization conditions may be routinely determined by optimization procedures. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but not limited to, a pair of peroxidase (e.g., horseradish peroxidase) and chloronaphthol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine; a pair of alkaline phosphatase and bromochloroindolylphosphate (BCIP), nitro blue tetrazolium (NBT), naphthol-AS-B1-phosphate or ECF substrate; and a pair of glucosidase and t-NBT (nitroblue tetrazolium) or m-PMS (phenzaine methosulfate). Where probes are labeled with gold particles, the occurrence of hybridization may be detected by silver staining method using silver nitrate.

In these connections, where the present method for diagnosing asthma is carried out by hybridization, it comprises the steps of (i) contacting a nucleic acid sample to a probe having a nucleotide sequence complementary to the nucleotide sequence of the BLT2 gene; and (ii) detecting the occurrence of hybridization.

The signal intensity from hybridization is indicative of asthma. When the hybridization signal to BLT2 cDNA from a sample to be diagnosed is measured to be stronger than normal samples, the sample can be determined to have asthma.

According to a preferred embodiment, the primers of this invention are used for amplification reactions.

The term used herein "amplification reactions" refers to reactions for amplifying nucleic acid molecules. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., Molecular Cloning. A Laboratory Manual, 3rd ed. Cold Spring Harbor Press (2001)), the methods of Miller, H. I. (WO 89/06700) and Davey, C. et al. (EP 329,822), ligase chain reaction (LCR) (17, 18), Gap-LCR (WO 90/01069), repair chain reaction (EP 439,182), transcription-mediated amplification (TMA)(19) (WO 88/10315), self sustained sequence replication (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification and loop-mediated isothermal amplification (LAMP), but not limited to. Other amplification methods that may be used are described in, U.S. Pat. Nos. 5,242,794, 5,494,810, 4,988,617 and in U.S. Ser. No. 09/854,317.

According to the most preferred embodiment, the amplification reaction is carried out in accordance with PCR (polymerase chain reaction) which is disclosed in U.S. Pat. Nos. 4,683,195, 4,683,202, and 4,800,159.

PCR is one of the most predominant processes for nucleic acid amplification and a number of its variations and applications have been developed. For example, for improving PCR specificity or sensitivity, touchdown PCR(24), hot start PCR(25, 26), nested PCR(2) and booster PCR(27) have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR have been suggested for certain applications. The details of PCR can be found in McPherson, M J., and Moller, S. G. PCR. BIOS Scientific Publishers, Springer-Verlag New York Berlin Heidelberg, N.Y. (2000), the teachings of which are incorporated herein by reference in its entity.

Where the present method for diagnosing asthma is carried out using primers, the nucleic acid amplification is executed for analyzing the expression level of the BLT2 gene. Because the present invention is intended to assess the expression level of the BLT2 gene, the level of the BLT2 mRNA in samples is analyzed.

Therefore, the present invention performs nucleic acid amplifications using mRNA molecules in samples as templates and primers to be annealed to mRNA or cDNA. For obtaining mRNA molecules, total RNA is isolated from samples. The isolation of total RNA may be performed by various methods (Sambrook, J. et al., Molecular Cloning. A Laboratory Manual, 3rd ed. Cold Spring Harbor Press (2001); Tesniere, C. et al., Plant MoI. Biol. Rep., 9:242 (1991); Ausubel, F. M. et al., Current Protocols in Molecular Biology, John Willey & Sons (1987); and Chomczynski, P. et al., Anal. Biochem. 162:156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (PNAS USA, 85:8998 (1988); Libert F, et al., Science, 244:569 (1989); and Sambrook, J. et al., Molecular Cloning. A Laboratory Manual, 3rd ed. Cold Spring Harbor Press (2001)). cDNA molecules synthesized are then amplified by amplification reactions.

The primers used for the present invention is hybridized or annealed to a region on template so that double-stranded structure is formed. Conditions of nucleic acid hybridization suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu).

When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

Annealing or hybridization in the present method is performed under stringent conditions that allow for specific binding between the primer and the template nucleic acid. Such stringent conditions for annealing will be sequence-dependent and varied depending on environmental parameters.

The amplified BLT2 cDNA molecules are then analyzed to assess the expression level of the BLT2 gene. For example, the amplified products are resolved by a gel electrophoresis and the bands generated are analyzed to assess the expression level of the BLT2 gene. When the expression level of the BLT2 gene from a sample to be diagnosed is measured to be higher than normal samples, the sample can be determined to have asthma.

In these connections, where the present method for diagnosing asthma is carried out by amplification, it comprises the steps of (i) amplifying a nucleic acid sample by use of a primer having a nucleotide sequence complementary to the nucleotide sequence of the BLT2 gene; and (ii) analyzing the amplified products to determine the expression level of the BLT2 gene. In a preferred embodiment, the kit may comprise a pair of primers having a forward sequence of SEQ ID NO: 9 and a reverse sequence of SEQ ID NO: 10. This primer set can detect both of the long form and short form BLT2.

In a preferred embodiment, the kit may comprise a pair of primers having a forward sequence of SEQ ID NO: 11 and a reverse sequence of SEQ ID NO: 12. This primer set can detect only long form of BLT2 because the primer recognizes the front part of long form CDS. According to another aspect of the present invention, there is provided a kit for detecting asthma, which comprises an antibody binding specifically to BLT2 protein. The diagnosing kit for asthma may be constructed by incorporating an antibody binding specifically to the BLT2 protein.

The antibody against the BLT2 protein used in this invention may polyclonal or monoclonal, preferably monoclonal. The antibody could be prepared according to conventional techniques such as a fusion method (Kohler and Milstein, European Journal of Immunology, 6:511-519 (1976)), a recombinant DNA method (U.S. Pat. No. 4,816,56) or a phage antibody library (Clackson et al, Nature, 352:624-628 (1991) and Marks et al, J. MoI. Biol., 222:58, 1-597 (1991)). The general procedures for antibody production are described in Harlow, E. and Lane, D., Antibodies: A Laboratory Manual, Cold Spring Harbor Press, New York, 1988; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991, which are incorporated herein by references. For example, the preparation of hybridoma cell lines for monoclonal antibody production is done by fusion of an immortal cell line and the antibody producing lymphocytes. This can be done by techniques well known in the art. Polyclonal antibodies may be prepared by injection of the BLT2 protein antigen to suitable animal, collecting antiserum containing antibodies from the animal, and isolating specific antibodies by any of the known affinity techniques.

Where the diagnosing method of this invention is performed using antibodies to the BLT2 protein, it could be carried out according to conventional immunoassay procedures for detecting asthma.

Such immunoassay may be executed by quantitative or qualitative immunoassay protocols, including radioimmunoassay, radioimmuno-precipitation, enzyme-linked immunosorbent assay (ELISA), capture-ELISA, inhibition or competition assay, sandwich assay, flow cytometry, immunofluorescence assay and immunoaffinity assay, but not limited to. The immunoassay and immunostaining procedures can be found in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Press, 1999, which are incorporated herein by references. For example, according to the radioimmunoassay method, the radioisotope (e.g., $C^{14}$, $I^{125}$, $P^{32}$ and $S^{35}$) labeled antibody may be used to detect the BLT2 protein.

In addition, according to the ELISA method, the example of the present method may comprise the steps of: (i) coating a surface of solid substrates with cell lysate to be analyzed; (ii) incubating the coated cell lysate with a primary antibody to the BLT2 protein; (iii) incubating the resultant with a secondary antibody conjugated with an enzyme; and (iv) measuring the activity of the enzyme.

The solid substrate useful in this invention includes carbohydrate polymer (e.g., polystyrene and polypropylene), glass, metal and gel, most preferably microtiter plates.

The enzyme conjugated with the secondary antibody is that catalyzing colorimetric, fluorometric, luminescence or infrared reactions, e.g., including alkaline phosphatase, β-galactosidase, luciferase, Cytochrome $P_{450}$ and horseradish peroxidase. Where using alkaline phosphatase, bromochloroindolylphosphate (BCIP), nitro blue tetrazolium (NBT) or ECF may be used as a substrate for color-developing reactions; in the case of using horseradish peroxidase, chloronaphthol, aminoethylcarbazol, diaminobenzidine, D-luciferin, lucigenin (bis-W-methylacridinium nitrate), resorufin benzyl ether, luminol, Amplex Red reagent (10-acety 1-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

Where the present method is performed in accordance with the capture-ELISA method, the specific example of the present method may comprise the steps of: (i) coating a surface of a solid substrate with a capturing antibody capable of binding specifically to the BLT2 protein; (ii) incubating the capturing antibody with a cell sample to be analyzed; (iii) incubating the resultant of step (ii) with a detecting antibody which is capable of binding specifically to the BLT2 protein and conjugated with a label generating a detectable signal; and (iv) detecting the signal generated from the label conjugated with the detecting antibody.

The detecting antibody has a label generating a detectable signal. The label includes, but not limited to, a chemical (e.g., biotin), an enzymatic (e.g., alkaline phosphatase, horseradish peroxidase, β-galactosidase and Cytochrome $P45_0$), a radioactive (e.g., $C^{14}$, $I^{125}$, $P^{32}$ and $S^{35}$), a fluorescent (e.g., fluorescein), a luminescent, a chemiluminescent and a FRET (fluorescence resonance energy transfer) label. Various labels and methods for labeling antibodies are well known in the art (Ed Harlow and David Lane, Using Antibodies, A Laboratory Manual, Cold Spring Harbor Laboratory Press, 1999).

The detection of the signal generated from the label conjugated with the detecting antibody can be carried out by various processes well known in the art. The detection of the signal enables to analyze the BLT2 protein in a quantitative or qualitative manner. Where biotin and luciferase are used as labels, the signal detection may be achieved by use of streptavidin and luciferin, respectively.

The measurement of signal intensities generated from the immunoassay described above is indicative of asthma. When the signal to the BLT2 protein in a biosample to be diagnosed is measured to be higher than normal samples, the biosample can be determined to have asthma. The kit of the present invention may optionally include other reagents along with primers, probes or antibodies described above. For instance, where the present kit may be used for nucleic acid amplification, it may optionally include the reagents required for performing PCR reactions such as buffers, DNA polymerase (thermostable DNA polymerase obtained from *Thermus aquaticus* (Taq), *Thermus thermophilus* (Tth), *Thermus filiformis, Thermis flavus, Thermococcus literalis*, and *Pyrococcus furiosus* (Pfu)), DNA polymerase cofactors, and deoxyribonucleotide-5-triphosphates. The kits, typically, are adapted to contain in separate packaging or compartments the constituents afore-described.

The kits for detecting or diagnosing asthma permit to determine the development, aggravation and alleviation of asthma. In this regard, the term used herein "detecting or diagnosing" with reference to disease means not only the determination of the existence of disease but also the development, aggravation and alleviation of disease.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

According to another aspect of the present invention, there is provided a kit for detecting asthma, which comprises a primer or probe having a nucleotide sequence complementary to the nucleotide sequence of the Rac gene. Therefore, any methodology or kit developed based on the information that Rac overexpression is detected in the lung airway of a patient with asthma may be included in the present invention.

According to another aspect of the present invention, there is provided a kit for detecting asthma, which comprises an antibody binding specifically to Rac protein. The diagnosing kit for asthma may be constructed by incorporating an antibody binding specifically to the Rac protein. A pharmaceutical composition of this invention may be administered orally or parenterally (e.g., intravenous injection, subcutaneous injection, intramuscular injection and local injection).

The administration of a compound or a combination of compounds for the treatment of asthma may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The term "therapeutically effective amount" as used herein means an amount of the substance that is capable of producing a medically desirable result in a treated subject. The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. According to a preferred embodiment of this invention, a daily suitable dosage unit for human host ranges from 0.001-100 mg/kg (body weight). Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Asthma is a chronic inflammatory disease of the airway characterized by eosinophil infiltration, mucus hypersecretion and AHR. Although there have been many studies of the role of BLT1 in asthma, the role of BLT2 has not yet been defined. By employing a pharmacological BLT2 antagonist and an antisense nucleotide sequence that blocked endogenous BLT2 expression, BLT2 was demonstrated to play a critical role in the development of AHR and airway inflammation. Results showed that BLT2 mediates the asthmatic response by stimulating ROS generation and subsequent NF-κB activation. This is the first report that BLT2 is induced by allergenic stimuli and that blockade of BLT2 mitigates the asthmatic response.

A number of earlier studies have shown that the 'LTB$_4$-BLT1' pathway plays a central role in the early chemoattraction of granulocytes such as eosinophils to inflamed tissues, thereby acting as a local inflammatory mediator (3, 35). The LTB$_4$-BLT1 pathway is also considered pivotal for the allergen-mediated recruitment of effector CD4+ and CD8+ T lymphocytes into airways, thereby controlling the immunological response, as well (10-12, 36). LTB$_4$-BLT1 is therefore believed to contribute to the development of asthma through recruitment of granulocytes and effector CD4+ and CD8+ T lymphocytes. In contrast to BLT1, BLT2 has a low affinity for LTB$_4$, and no clear physiological function has yet been identified for it. Surprisingly and unexpectedly, BLT2 was dramatically upregulated during OVA-induced allergic pulmonary inflammation in the asthma model. Unlike BLT1, which is mainly expressed in myeloid leukocytes and specific classes of T cells, BLT2 was induced in the airway epithelium and in parts of the endothelium (FIG. 1C), where LTB$_4$ is abundantly generated in response to allergen challenge. After aerosol challenge with OVA, airway mast cells and alveolar macrophages are activated. These cells are thought to be the major source of LTB$_4$ in the airways at early times following allergen challenge. Although LTB$_4$ is believed to attract eosinophils, neutrophils and differentiated T cells to airways via the BLT1 they express, LTB$_4$ may also interact with BLT2 induced in the airway epithelium in the local microenvironment and stimulate intracellular signaling leading to upregulation of VCAM-1 and other proinflammatory proteins. The induced VCAM-1 could in turn enhance trafficking of inflammatory leukocytes across the epithelial layer to the airways, thereby contributing to a development of airway inflammation and AHR. In fact, leukocyte emigration into the alveolar compartments is a prominent feature of acute and chronic inflammatory lung injuries such as asthma (37). During this emigration process, airway epithelial cells are probably important not only for retention and activation of leukocytes, but also for regulating their passage into the airways. In any event, the distribution and function of 'LTB$_4$-BLT2' during the asthmatic response appear to be unique and distinguishable from that of LTB$_4$-BLT1. BLT2 clearly plays only a minimal role in T cell recruitment; consequently, T cell recruitment to airways remained intact after administration of antisense BLT2 (FIG. 8), while AHR and airway inflammation were attenuated (FIG. 8). This means the mechanism by which BLT2 inhibition suppresses AHR and airway inflammation is independent of T cell recruitment. On the other hand, no expression of BLT2 was detected in CD4+ T cells and CD8+ TEFF cells, though they strongly express BLT1 (10, 38).

Without being bound to a particular theory, ROS is a major downstream component of the LTB$_4$-BLT2 pathway mediating AHR and airway inflammation in allergic asthma. Accumulating evidence suggests that ROS and the oxidative stress they cause play crucial roles in the pathogenesis of airway inflammation and AHR (29, 39-41). At later stages, moreover, the inflammatory cells recruited to the asthmatic airways have the capability to produce ROS, and the ROS released by eosinophils and other leukocytes infiltrating the airways cause the tissue injury observed in asthma (42).

That said, in this case it is not believed that ROS are acting merely as nonspecific pathogenic mediators of oxidative stress. Instead, they appear to have a specific signaling function in the pathway leading to upregulation of target genes associated with asthma. In support of this idea, BLT2 activity was previously shown to leads to enhanced ROS generation, which in turn mediates specific intracellular signaling responses (7, 37). Although the molecular basis of ROS-mediated induction of AHR and inflammation remains unknown, recent studies have shown that ROS generation in asthma leads to activation of the redox-sensitive transcription factor NF-κB (32, 43), which is present in most cell types and plays a critical role in immune and inflammatory responses, including asthma (44). For instance, NF-κB activation contributes to the development and maintenance of asthma in the bronchial epithelium (45), and has been observed in airway epithelial cells (46) in which BLT2 mRNA is induced during the OVA-induced allergic response. Consistent with those observations, in the present study NF-κB levels were substantially elevated in extracts of lung tissue from mice with OVA-induced asthma and were specifically suppressed by BLT2 antisense (FIG. 6A). It is known that activation of NF-κB induces a variety of pro-inflammatory genes, including adhesion molecules (e.g., VCAM-1) (33, 34). As expected, expression of VCAM-1 increased following allergen challenge, and BLT2 antisense or a receptor antagonist reduced its expression (FIGS. 6C and 6E), whereas BLT1 antisense had no effect (data not shown).

BLT2−/− knockout mice are difficult to generate because the BLT2 gene resides within the BLT1 locus (47). Disruption of BLT2 therefore interferes with BLT1 expression, making it difficult to interpret the outcome. Therefore, transgenic mice were prepared overexpressing BLT2 and detected elevated levels of ROS in their BAL fluid (Cho et al., unpublished observation). In addition, significant induction of AHR was observed, even before OVA challenge, which further supports the proposed mediatory role of BLT2 in the pathogenesis of asthma (Cho et al., unpublished observation).

Applicants have discovered a relationship between asthma and a BLT2-linked signaling cascade. Without being bound to a particular theory, LTB$_4$ exerts its effects through both BLT1- and BLT2-dependent signaling pathways and that the two may cooperate during the development of allergic asthma, although attenuation of either pathway suppressed asthmatic symptoms. A better understanding of the BLT2-linked pathway and possible cross-regulation between the BLT1 and BLT2 pathways should help to clarify their role in LTB$_4$-mediated allergic pathogenesis. The finding that a LTB$_4$-BLT2-ROS pathway is involved in asthma could serve as the b for the development of new diagnostic tools and treatments for allergic disease.

Practical and presently preferred embodiments of the present invention are illustrated as shown in the following Examples. However, it will be appreciated that those skilled in the art, on consideration of this disclosure, may make modifications and improvements within the spirit and scope of the present invention.

EXAMPLES

Example 1

Sensitization and Challenge of Mice

Female BALB/c mice and C57BL/6 mice (7 weeks old; 18-20 g) were obtained from Orientbion Inc. (Seoungnam, Korea). Sensitization and challenge were carried out as described previously with some modification (28). Briefly, female C57BL/6 mice (7 weeks old; 18-20 g) were immunized by intraperitoneal (i.p.) injection of 200 µg ovalbumin (OVA) emulsified in 2.5 mg of adjuvant aluminum hydroperoxide gel (alum) (Pierce, Rockford, Ill.). A second i.p. injection of 20 µg OVA adsorbed onto alum (2.5 mg) was administered 10 days later. After an additional 10 days, mice were exposed to an aerosol of 1% OVA in saline for 30 min daily on 3 consecutive days. On day 25, mice were finally challenged by provocation with 10% OVA aerosol. For inhibition experiments, sense or antisense BLT2 (1.6 mg/kg) was injected intravenously 24 h and then 1 h before the 10% OVA challenge. The mice were then killed on day 27 to assess asthmatic phenotypes. Antisense BLT2 oligonucleotide (5'-GCTCAGTAGTGTCTCATTCC-3' (SEQ ID NO: 15)), sense BLT2 oligonucleotide (5'-GGAATGAGACACTACTGAGC-3' (SEQ ID NO: 16)).

Alternatively, BALB/c mice were sensitized on day 1 by i.p. injection of 20 µg OVA emulsified in 2.5 mg of alum (Pierce, Rockford, Ill.), followed by an identical booster injection administered on day 14. On days 21, 22 and 23 after initial sensitization, the mice were challenged for 30 min with an aerosol of 1% OVA using an ultrasonic nebulizer. LY255283 (2.5 mg/kg) or vehicle control (DMSO) was administered intravenously 1 h before 1% OVA challenge. Mice were killed on day 25, to assess asthmatic phenotypes. 2',7'-dichorofluorescein diacetate (DCF-DA) was purchased from Molecular Probes (Eugene, Oreg.). BSA and DMSO were from Sigma-Aldrich (St. Louis, Mo.). Acetyl-methacholine chloride was purchased from Sigma-Aldrich (St. Louis, Mo.). All other chemicals were from standard sources and were of molecular biology grade or higher. All mice were maintained and bred under specific pathogen-free conditions in the Korea University mouse facility, and experiments were conducted within the parameters of an approved protocol by the Animal Research Committee.

Example 2

Induction of BLT2 mRNA in the Ova-Induced Asthmatic Mouse Lung

1) Quantification of $LTB_4$ (FIG. 1a)

Levels of $LTB_4$ were quantified with the leukotriene B4 enzyme immunoassay (EIA) Biotrak™ system (Amersham Biosciences, UK). Briefly, 200 µl BAL fluid were concentrated by freeze-drying for 12 h and reconstituted in assay buffer. The sensitivity of the assay was 0.3 pg/well, which is equivalent to 6 pg/ml.

Figure 1B:
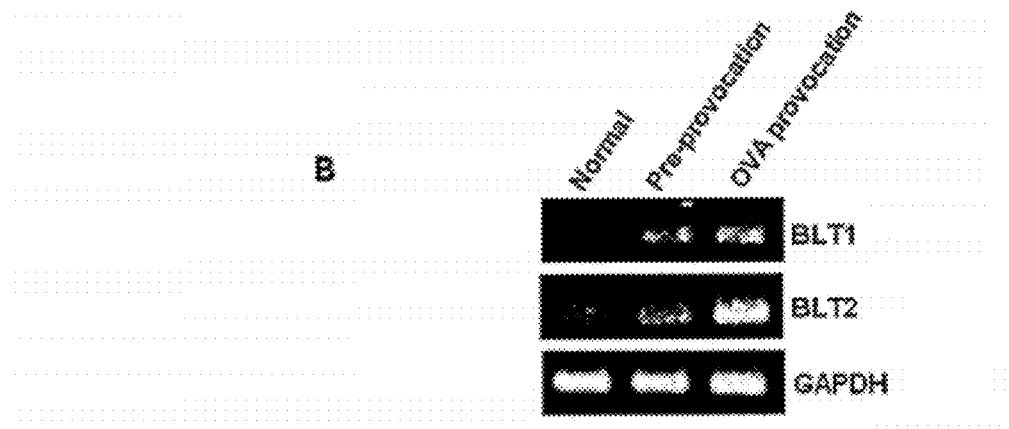

2) Semiquantitative RT-PCR (FIG. 1b)

Total RNA was extracted from lung samples using Easy-blue RNA extraction reagent (Intron, Korea). The extracted RNA (1 µg) was reverse transcribed for 1 hr at 42° C. and amplified by PCR using the following primers: for mouse BLT2,5'-CAGCATGTACGCCAGCGTGC-3' (sense; SEQ ID NO: 17) and 5'-CGATGGCGCTCACCAGACG-3' (antisense; SEQ ID NO: 18); and for mouse BLT1,5'-GCATGTCCCTGTCTCTGTTG-3' (sense; SEQ ID NO: 19) and 5'-CGGGCAAAGGCCTTAGTACG-3' (antisense; SEQ ID NO: 20). For the semiquantitative analysis of transcripts, the optimal PCR conditions were first determined by linear amplification of glyceraldehyde-3-phosphate dehydrogenase (GAPDH). Thereafter, 28 cycles was used for BLT amplification and was found to be in the linear range. The amplified PCR products were separated by electrophoresis on 1.2% agarose gel and stained with ethidium bromide.

Figure 1C:
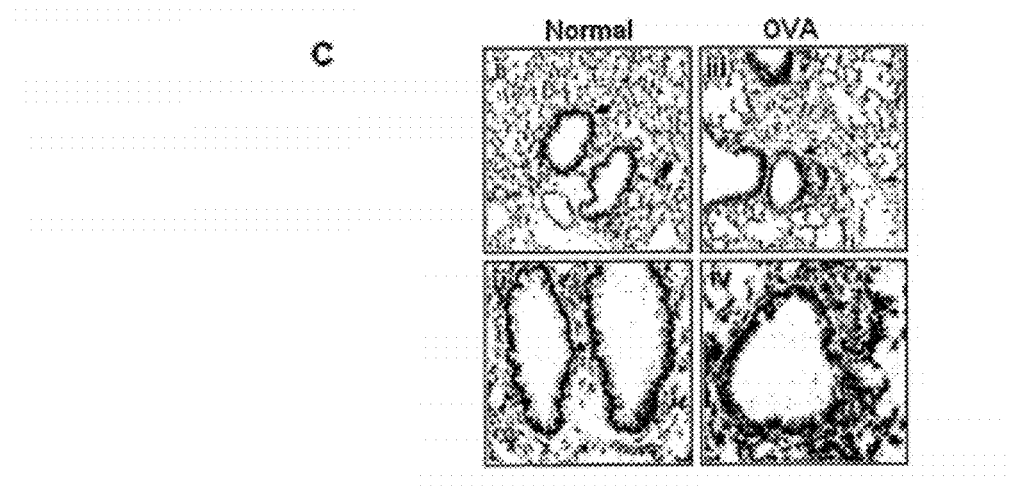

3) In Situ Hybridization for BLT2 in Mouse (FIG. 1c)

The cDNA encoding mouse BLT2 was amplified by PCR with the mouse BLT2 primers and confirmed by sequencing. All linearized vectors were transcribed with T7 RNA polymerase and digoxigenin (DIG) RNA labeling mix (Roche, Germany). Embedded mouse lung tissues were deparaffinized with xylene, after which in situ hybridization was carried out using an in situ hybridization detection kit (InnoGenex, CA) according to the manufacturer's protocol.

Example 3

Figure 2A:
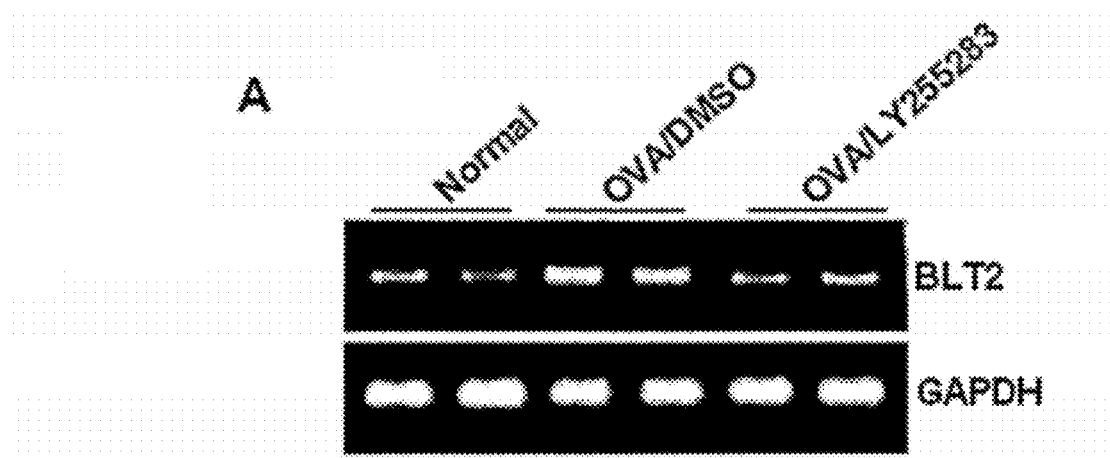
FIGS. 2a-2d show that LY255283 attenuated airway inflammation in asthma. BALB/c mice were intravenously injected with LY255283 (2.5 mg/kg) or vehicle (DMSO) 1 hr before 1% OVA challenge. The mice were then killed on day 25 to assess asthmatic phenotypes.

Blockade of BLT2 Signaling Using a Pharmacological Antagonist (LY255283) Suppresses Airway Inflammation 1) Semiquantitative RT-PCR (FIG. 2a)

Total RNA was extracted from lung samples using Easy-blue RNA extraction reagent (Intron, Korea). The extracted RNA (1 µg) was reverse transcribed for 1 hr at 42° C. and amplified by PCR using the following primers: for mouse BLT2,5'-CAGCATGTACGCCAGCGTGC-3' (sense; SEQ ID NO: 17) and 5'-CGATGGCGCTCACCAGACG-3' (antisense; SEQ ID NO: 18); and for mouse BLT1, 5'-GCATGTCCCTGTCTCTGTTG-3' (sense; SEQ ID NO: 19) and 5'-CGGGCAAAGGCCTTAGTACG-3' (antisense; SEQ ID NO: 20). For the semiquantitative analysis of transcripts, the optimal PCR conditions were first determined by linear amplification of glyceraldehyde-3-phosphate dehydrogenase (GAPDH). Thereafter, 28 cycles was used for BLT amplification and was found to be in the linear range. The amplified PCR products were separated by electrophoresis on 1.2% agarose gel and stained with ethidium bromide.

Figure 2B:
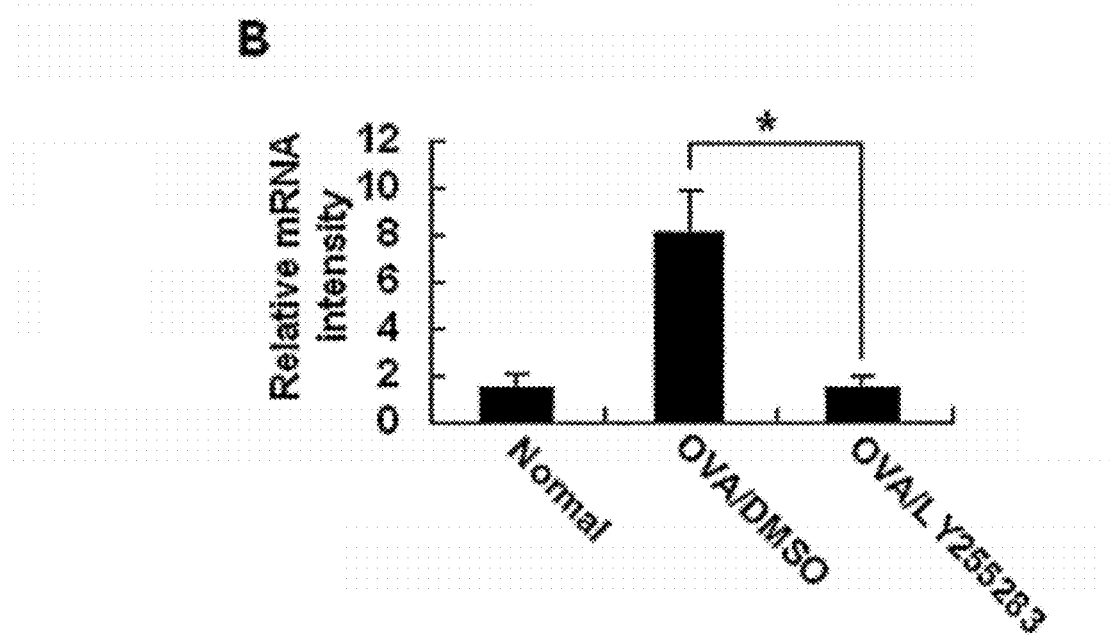

2) Real-Time PCR (FIG. 2b)

For real-time PCR, total RNA were extracted from lung tissue using Easy-blue RNA extraction reagent (Intron, Korea), after which the extracted RNA was reverse transcribed using M-MLV reverse transcriptase (Invitrogen, CA). The PCR reactions were then carried out using LightCycler 480 SYBR Green I Master (Roche, Germany) according to the manufacturer's instructions.

Figure 2C:
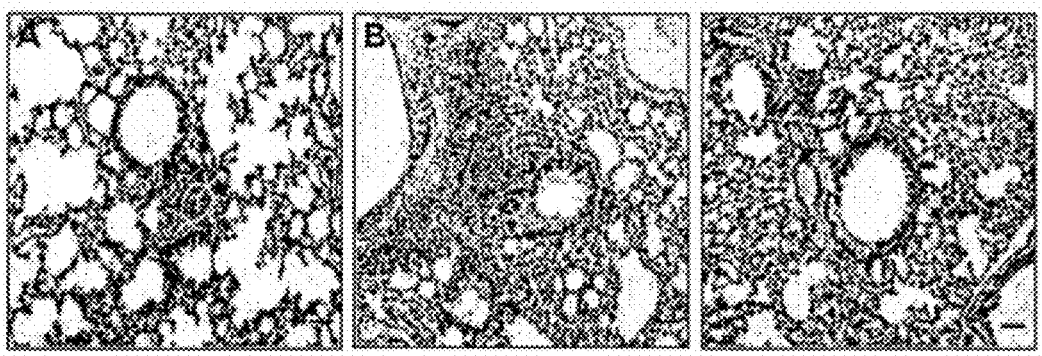
Figure 2D:
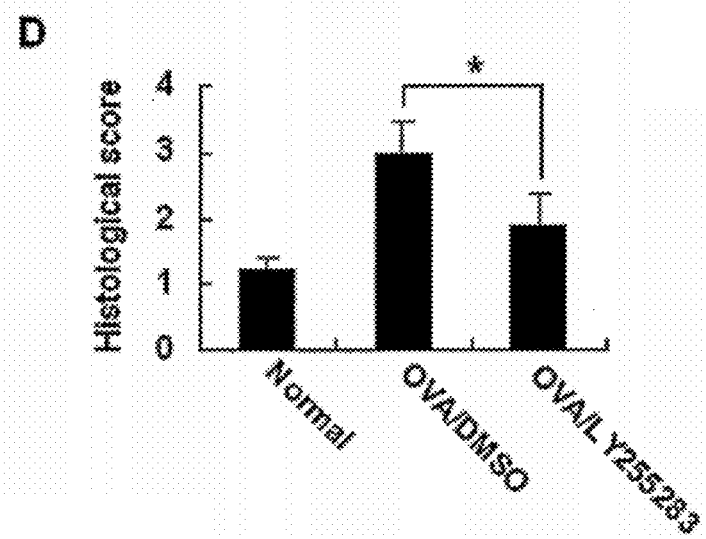

3) BAL and Histological Analysis of Lung (FIGS. 2c and 2d)

Inflammatory cells in the BAL fluid were collected by centrifugation (1,000 g for 3 min) and washed once in PBS. Cells were counted using a hemocytometer, and viability was assessed by trypan blue exclusion. In addition, cytospin was carried out for each BAL sample, which was then stained with Diff-Quick (Merck, Dorset, U.K.), enabling differential cell counts to be made. For histological analysis, the lungs of the mice were dissected 48 h after OVA challenge and fixed with 10% formaldehyde in PBS, dehydrated in ethanol-xylene, and embedded in paraffin. Multiple paraffin-embedded 6 µm sections were placed on 0.5% gelatin-coated slides, deparaffinized, and stained with hematoxylin-eosin (HE). Images were acquired using a BX51 microscope (Olympus, Tokyo, Japan) equipped with a DP71 digital camera (Olympus, Tokyo, Japan).

Example 4

Figure 3A:
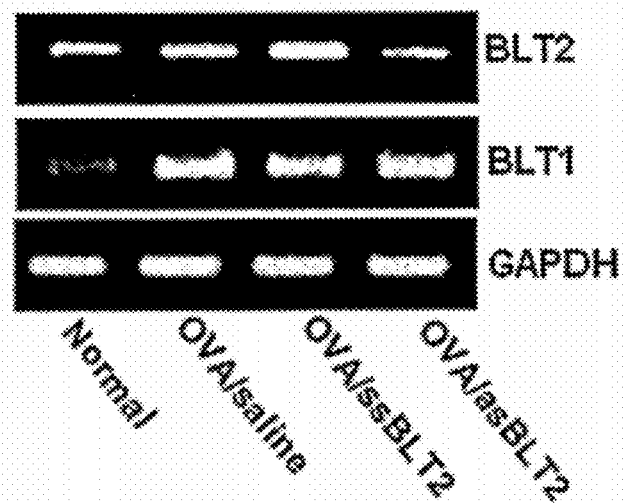
FIGS. 3a-3d show that antisense BLT2 attenuated airway inflammation in asthma.

Blockade of BLT2 Signaling Using a Pharmacological Antisense BLT2 Suppresses Airway Inflammation 1) Semiquantitative RT-PCR (FIG. 3a)

Total RNA was extracted from lung samples using Easy-blue RNA extraction reagent (Intron, Korea). The extracted RNA (1 µg) was reverse transcribed for 1 h at 42° C. and amplified by PCR using the following primers: for mouse BLT2,5'-CAGCATGTACGCCAGCGTGC-3' (sense; SEQ ID NO: 17) and 5'-CGATGGCGCTCACCAGACG-3' (antisense; SEQ ID NO: 18); and for mouse BLT1,5'-GCATGTC-CCTGTCTCTGTTG-3' (sense; SEQ ID NO: 19) and 5'-CGGGCAAAGGCCTTAGTACG-3' (antisense; SEQ ID NO: 20). For the semiquantitative analysis of transcripts, the optimal PCR conditions were first determined by linear amplification of glyceraldehyde-3-phosphate dehydrogenase (GAPDH). Thereafter, 28 cycles was used for BLT amplification and was found to be in the linear range. The amplified PCR products were separated by electrophoresis on 1.2% agarose gel and stained with ethidium bromide.

Figure 3B:
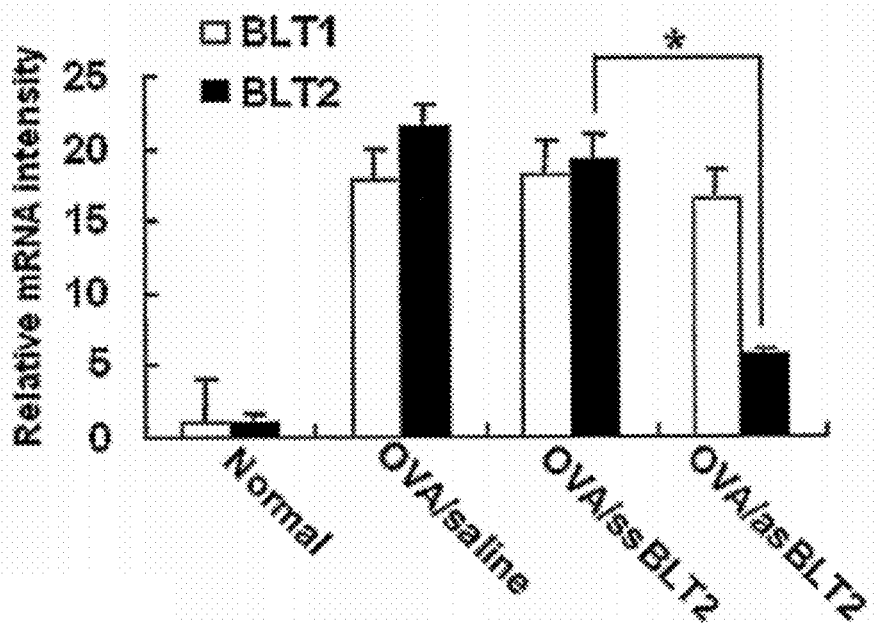

2) Real-Time PCR (FIG. 3b)

For real-time PCR, total RNA were extracted from lung tissue using Easy-blue RNA extraction reagent (Intron, Korea), after which the extracted RNA was reverse transcribed using M-MLV reverse transcriptase (Invitrogen, CA). The PCR reactions were then carried out using LightCycler 480 SYBR Green I Master (Roche, Germany) according to the manufacturer's instructions.

Figure 3C:
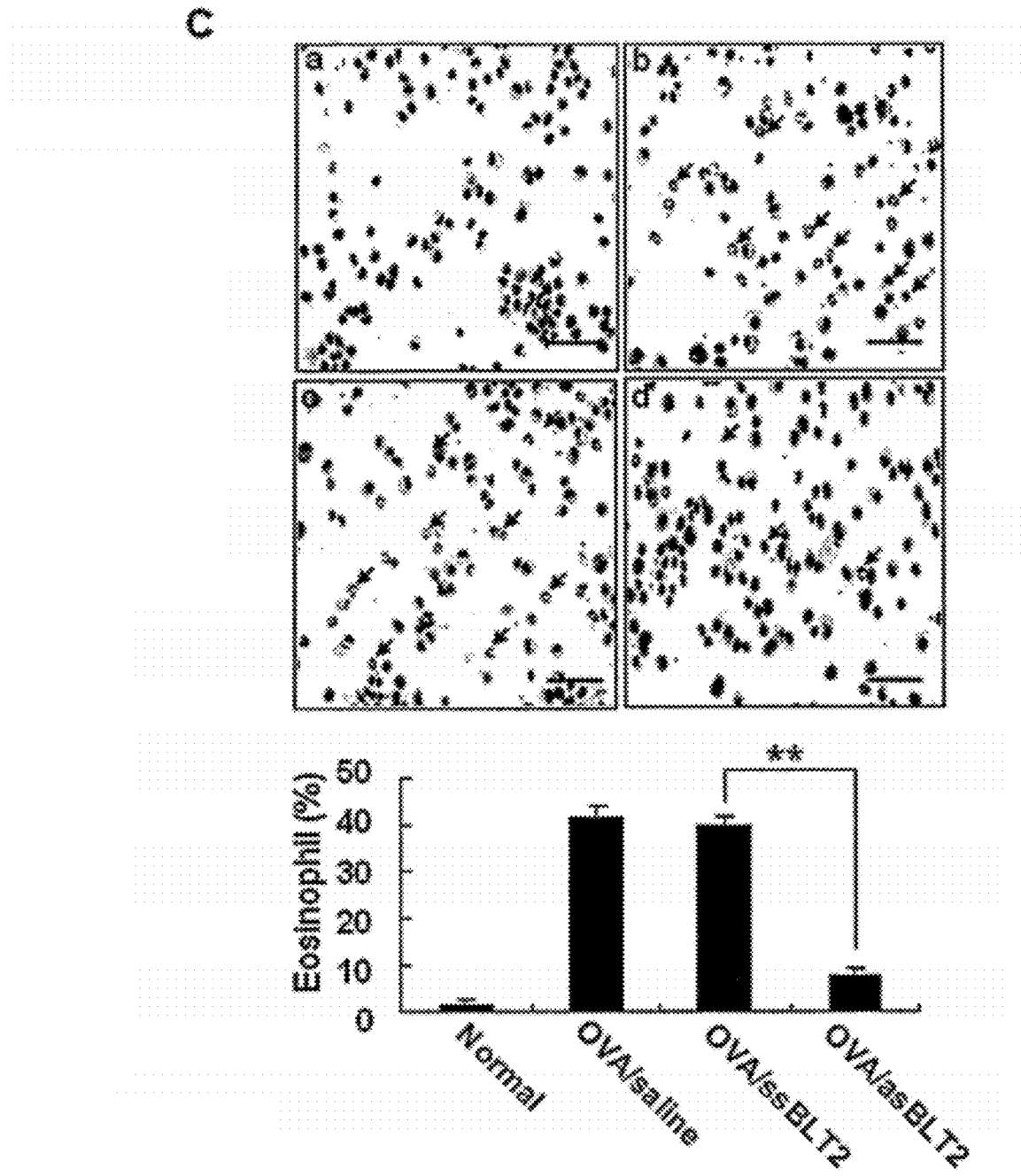
Figure 3D:
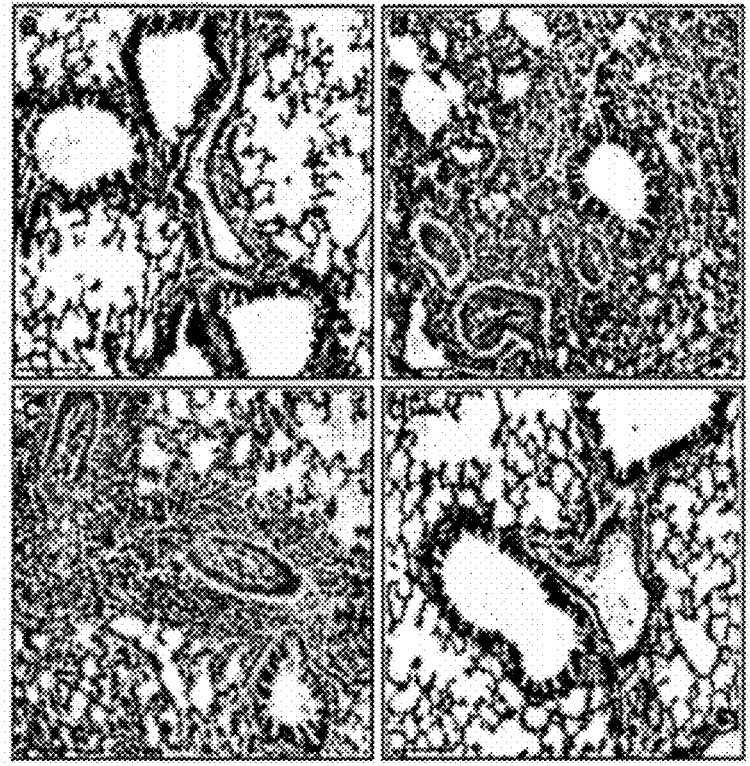
Figure 3D:
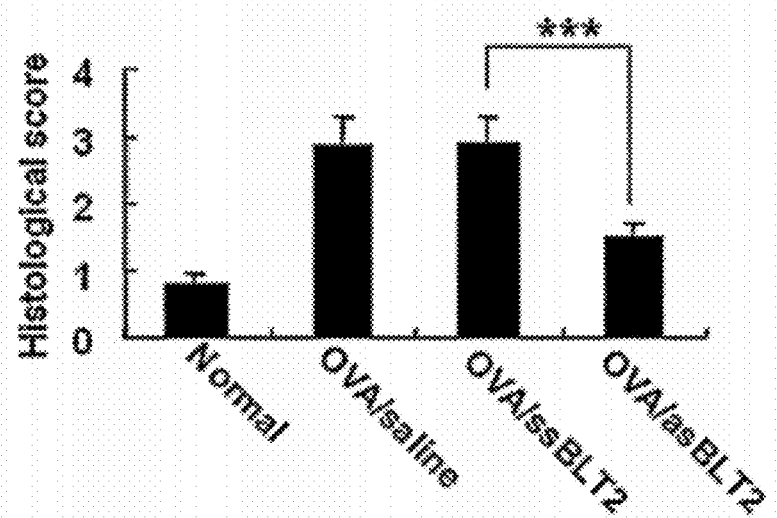

3) BAL and Histological Analysis of Lung (FIGS. 3c and 3d)

Inflammatory cells in the BAL fluid were collected by centrifugation (1,000 g for 3 min) and washed once in PBS. Cells were counted using a hemocytometer, and viability was assessed by trypan blue exclusion. In addition, cytospin was carried out for each BAL sample, which was then stained with Diff-Quick (Merck, Dorset, U.K.), enabling differential cell counts to be made. For histological analysis, the lungs of the mice were dissected 48 h after OVA challenge and fixed with 10% formaldehyde in PBS, dehydrated in ethanol-xylene, and embedded in paraffin. Multiple paraffin-embedded 6 µm sections were placed on 0.5% gelatin-coated slides, deparaffinized, and stained with hematoxylin-eosin (HE). Images were acquired using a BX51 microscope (Olympus, Tokyo, Japan) equipped with a DP71 digital camera (Olympus, Tokyo, Japan).

Example 5

Effect of BLT2 Inhibition on Airway AHR

1) Determination of AHR in Response to Methacholine (FIGS. 4a and 4b)

Airway AHR was measured in unrestrained, conscious mice 24 h after the final OVA challenge using a whole-body plethysmograph, as previously described (29). Mice were placed in a barometric plethysmographic chamber (All Medicus Co., Seoul, Korea), and baseline readings were taken and averaged for 3 min. Aerosolized methacholine in increasing concentrations (from 6.25 mg/ml~50 mg/ml) was nebulized through an inlet of the main chamber for 3 min. Readings were taken and averaged for 3 min after each nebulization, and enhanced pause (Penh) was determined. Signals were analyzed to derive whole body flow parameters including respiratory rate, tidal volume, inspiratory time (Ti), expiratory time (Te)$_1$. peak inspiratory flow (PIF), peak expiratory flow (PEF), and relaxation time (RT). These parameters were used to calculate enhanced pause (Penh), a unitless parameter that is used as a measure of airway responsiveness to methacholine. Penh reflects changes in pulmonary resistance during bronchoconstriction according to the following equation: Penh=[(Te−RT)÷RT]×(PEF÷PIF). Baseline Penh measurements for each animal were recorded for 3 min and averaged. Results are expressed as the percentage increase of Penh following challenge with each concentration of methacholine, where the baseline Penh (after saline challenge) is expressed as 100%. Penh values averaged for 3 min after each nebulization were evaluated.

Example 6

Attenuation of ROS Generation by BLT2 Inhibition

1) Measurement of ROS Levels in BAL Fluid (FIG. 5a)

ROS levels in BAL fluids were measured as a function of DCF fluorescence as described previously (30). Briefly, cells in the BAL fluid were collected by centrifugation (1,000 g for 3 min) and the pelleted cells were washed with PBS and incubated for 10 min with the H2O2-sensitive fluorophore 2',7'-dichorofluorescein diacetate (DCF-DA, 10 µM) (Molecular Probes, Eugene, Oreg.), which, when taken up, fluorescently labels intracellular H2O2 with DCF. Following washing, the cells were immediately observed using a FACS Calibur™ (Becton Dickinson, Franklin Lakes, N.J.). DCF fluorescence was excited at 488 nm and the evoked emission was filtered with a 515-nm long-pass filter.

2) Quantification of LTB$_4$ (FIG. 5b)

Levels of LTB$_4$ were quantified with the leukotriene B4 enzyme immunoassay (EIA) Biotrak™ system (Amersham Biosciences, UK). In brief, 200 µl BAL fluid was concentrated by freeze-drying for 12 h and reconstituted in assay buffer. The assay was calibrated with standard LTB$_4$ ranging from 0.31 to 40 pg/well. Samples of BAL fluid and standard LTB$_4$ in 96-well plates were incubated with antiserum for 2 hr, followed by LTB$_4$ peroxidase conjugate for 1 h at room temperature. To remove unbound ligand, the wells were aspirated and washed 4 times with buffer. Substrate (tetramethylbenzidine) was then added, and the reaction was stopped by adding an acid solution and the color read at 450 nm in a spectrophotometer. The sensitivity of the assay was 0.3 pg/well, which is equivalent to 6 pg/ml. Statistical significance of differences between groups was assessed by analysis of variance, and $P<0.05$ was considered significant.

Example 7

Attenuation of NF-κB Activation by BLT2 Inhibition

1) Electrophoretic Mobility Shift Assay (EMSA) (FIG. 6a)

A double-strand oligonucleotide corresponding to the consensus NF-κB binding motif and a mutant sequence were purchased from Santa Cruz Biotechnology Inc. (Santa Cruz, Calif.) and labeled with γ-32P-ATP using T4 polynucleotide kinase (Roche, Germany). Labeled oligonucleotide was then separated from free γ-32P-ATP on ProbeQuart™ G-50 microcolumns (Amersham Pharmacia Biotech, Ltd., UK) according to the manufacturer's protocol. Labeled oligonucleotide, 10 µg of nuclear extract and EMSA buffer were incubated for 1 h at room temperature in a final volume of 20 µl, after which the reaction mixture was subjected to electrophoresis.

2) SDS-PAGE and Immunoblot Analysis of Lung Cell Lysates (FIGS. 6b-6e)

Lung samples were prepared as described for preparation of total protein. The cell lysates were centrifuged at 13,000 g for 10 min and the supernatants subjected to SDS-PAGE on 10% acrylamide gels, followed by transfer to polyvinylidene difluoride (PVDF) membranes with a Novex wet transfer system (for 2 h at 100 V). The membranes were blocked for 1 h in Tris-buffered saline (TBS) containing 0.05% (v/v) Tween 20 plus 5% (w/v) nonfat dry skim milk, and then incubated for 2 h with the primary antibody in TBS containing 0.05% (v/v) Tween 20 plus 3% (w/v) BSA, followed for 1 h with horseradish peroxidase (HRP)-conjugated secondary antibody before development by enhanced chemiluminescence (ECL) (Amersham Pharmacia Biotech, Ltd., UK).

Example 8

Enhanced Expression of BLT2 in Samples from Clinically Asthmatic Subjects

1) Bronchoscopy (FIG. 7)

Bronchial biopsy specimens were obtained from 4 nonasthmatic controls (normal), 4 mild bronchial asthma patients and 5 moderate bronchial asthma patients. The patients studied were recruited from the outpatient clinic of Soonchunhyang University Hospital, Korea. The subjects in the nonasthmatic control group had no history of broncho-pulmonary disease and had an FEV1>80% of predicted and an FEV1/FVC %>70%. The mild bronchial asthmatic group had an FEV1>70% and moderate bronchial asthmatic group had an FEV1<70%. All specimens were formalin-fixed, paraffin-embedded and processed for routine histological diagnosis. The study was approved by the ethics committee of Soonchunhyang University Hospital, and the patients provided written informed consent. The pattern of BLT2 expression in the bronchial biopsy specimens was detected immunohistochemically using an alkaline phosphatase substrate system.

Example 9

BLT2 Inhibition does not Interfere with Recruitment of T Lymphocytes into Airways 1) Flow Cytometric Analysis of Cells in BAL Fluid (FIGS. 8a-8b)

For flow cytometric analysis, the cells in the BAL fluid were suspended in 50 µl of PBS containing 0.01% sodium azide and 0.1% BSA. BAL leukocytes were incubated for 30 min with 2.4G2 anti-FcγIII/II receptor (BD PharMingen) and stained for 30 min at 4° C. with FITC-conjugated anti-mouse TCR. chain (BD PharMingen) and PE-cy5 anti-mouse CD8a (BD PharMingen) or PE rat anti-mouse CD4 (BD PharMingen). Cytofluorimetry was performed with a FACS Calibur™ (Becton Dickinson, Franklin Lakes, N.J.), and the results were analyzed with CellQuest software (Becton-Dickinson).

Example 10

Antisense Rac Oligonucleotide Experiment

Oligonucleotides, from Genotech Co. (Korea), were synthesized with a phosphorothioate backbone to improve the resistance to endonuclease. The antisense oligonucleotide consisted of 17 nucleotides analogues to the 5' end of the murine Rac mRNA sequence, which spans the translation initiation site. The control Rac oligonucleotide contained the same nucleotide composition as the antisense oligonucleotide. Oligonucleotides (1.25 mg/kg of weight) were injected into the tail veins of the mice 24 and 4 hr before OVA provocation. The sequences of the oligonucleotides used in this study were as follows. Control Rac: 5'-GATCAGTGCACA-CAGTG-3' (SEQ ID NO: 21); Antisense Rac: 5'-CACT-TGATGGCCTGCAT-3' (SEQ ID NO: 22).

1) BAL and Histological Analysis of Lung (FIG. 9a)

Inflammatory cells in the BAL fluid were collected by centrifugation (1,000 g for 3 min) and washed once in PBS. Cells were counted using a hemocytometer, and viability was assessed by trypan blue exclusion. In addition, cytospin was carried out for each BAL sample, which was then stained with Diff-Quick (Merck, Dorset, U.K.), enabling differential cell counts to be made. For histological analysis, the lungs of the mice were dissected 48 hr after OVA challenge and fixed with 10% formaldehyde in PBS, dehydrated in ethanol-xylene, and embedded in paraffin. Multiple paraffin-embedded 6 µm sections were placed on 0.5% gelatin-coated slides, deparaffinized, and stained with hematoxylin-eosin (HE). Images were acquired using a BX51 microscope (Olympus, Tokyo, Japan) equipped with a DP71 digital camera (Olympus, Tokyo, Japan).

2) Electrophoretic Mobility Shift Assay (EMSA) (FIG. 9b)

A double-strand oligonucleotide corresponding to the consensus NF-κB binding motif and a mutant sequence were purchased from Santa Cruz Biotechnology Inc. (Santa Cruz, Calif.) and labeled with γ-32P-ATP using T4 polynucleotide kinase (Roche, Germany). Labeled oligonucleotide was then separated from free γ-32P-ATP on ProbeQuart™ G-50 microcolumns (Amersham Pharmacia Biotech, Ltd., UK) according to the manufacturer's protocol. Labeled oligonucleotide, 10 µg of nuclear extract and EMSA buffer were incubated for 1 h at room temperature in a final volume of 20 µA after which the reaction mixture was subjected to electrophoresis.

3) SDS-PAGE and Immunoblot Analysis of Lung Cell Lysates (FIG. 9c)

Lung samples were prepared as described for preparation of total protein. The cell lysates were centrifuged at 13,000 g for 10 min and the supernatants subjected to SDS-PAGE on 10% acrylamide gels, followed by transfer to polyvinylidene difluoride (PVDF) membranes with a Novex wet transfer system (for 2 h at 100 V).

The membranes were blocked for 1 h in Tris-buffered saline (TBS) containing 0.05% (v/v) Tween 20 plus 5% (w/v) nonfat dry skim milk, and then incubated for 2 h with the primary antibody in TBS containing 0.05% (v/v) Tween 20 plus 3% (w/v) BSA, followed for 1 h with horseradish peroxidase (HRP)-conjugated secondary antibody before development by enhanced chemiluminescence (ECL) (Amersham Pharmacia Biotech, Ltd., UK).

Result 1: Induction of BLT2 mRNA in the Ova-Induced Asthmatic Mouse Lung

To assess the role of BLT2 in OVA-induced allergic asthma, levels of BLT2 and its ligand $LTB_4$ were measured. As shown in FIG. 1a, $LTB_4$ levels in BAL fluid increased following OVA challenge in this murine model of asthma, and peaked 48 h after the challenge. Semiquantitative RT-PCR analysis showed that levels of BLT2 mRNA in the lung increased dramatically after OVA challenge, while levels of BLT1 mRNA increased only slightly (FIG. 1b). To determine the distribution of BLT2 expression in the lung, in situ hybridization with an antisense BLT2 probe were next carried out and substantial elevation of BLT2 expression was detected in the epithelium with some induction in the endothelium (FIG. 1c). Thus, both LTB$_4$ and its receptor BLT2 appear to be upregulated in asthma.

Result 2: Blockade of BLT2 Signaling Using a Pharmacological Antagonist or Antisense BLT2 Suppresses Airway Inflammation To assess the possible mediatory role of BLT2 in asthmatic airway inflammation, a specific BLT2 antagonist, LY255283, was administrated intravenously 1 hr before the 1% OVA challenge, and the mice were then sacrificed 48 h after challenge. Semiquantitative RT-PCR (FIG. 2a) or real-time PCR analysis (FIG. 2b) showed that the level of BLT2 mRNA in the lung was greatly elevated after the OVA challenge, and administration of LY255283 significantly reduced BLT2 levels. Histological analysis of the infiltration of inflammatory cells into the lung revealed increased airway obstruction and leukocyte infiltration following OVA challenge (FIGS. 2c and 2d); again, LY255283 diminished the effect (FIG. 2e). Quantitative analysis of the histological samples, which entailed grading the airway inflammation as described in Materials and Methods, revealed that LY255283 reduced the inflammation score by ~66%, as compared to control (FIG. 2f).

To further evaluate the role of BLT2 in the pathogenesis of asthma, the effect of antisense BLT2 was analyzed. In this experiment, antisense BLT2 was administrated intravenously 24 hr and 1 hr before 10% OVA challenge, and the mice were sacrificed 48 hr after challenge. Subsequent semiquantitative RT-PCR analysis showed that the antisense BLT2 reduced BLT2 expression in the lung without interfering with that of BLT1 (FIG. 3a). Similar results were also obtained with real-time PCR analysis (FIG. 3b). Airway eosinophil accumulation is a hallmark of asthmatic pulmonary inflammation, and accumulation of eosinophils was detected in BAL fluid, which peaked 48 hr after the 10% OVA challenge. Administration of antisense BLT2 reduced eosinophil infiltration in BAL fluids by ~87%, whereas sense BLT2 had no inhibitory effect (FIG. 3c). In addition, histological analysis revealed increased airway obstruction and leukocyte infiltration following OVA challenge, and this effect, too, was diminished by antisense BLT2 (FIG. 3d). Consistent with those findings, administration of antisense BLT2 reduced inflammation scores by ~67%, as compared to control.

Result 3: Effect of BLT2 Inhibition on Airway AHR

To examine the contribution of BLT2 to AHR, the increase in Penh (enhanced pause) was determined to be elicited by methacholine (6.25-50 mg/ml). OVA-challenged mice developed significant AHR to the inhaled methacholine, and LY255283 or antisense BLT2 dramatically reduced Penh by ~70% (based on area-under-the-curve calculations), which suggests that BLT2 is in some way critical for the AHR reaction (FIGS. 4a-4b).

Result 4: Attenuation of ROS Generation by BLT2 Inhibition

The 'LTB$_4$-BLT2' cascade was previously shown to lead to enhanced ROS generation, which mediates various cellular effects (7). Therefore ROS levels were measured in BAL fluid following OVA challenge. As expected, the ROS levels in BAL fluid increased in the OVA-challenged mice. Notably, injection of antisense BLT2, but not sense BLT2, dramatically reduced ROS levels by ~70% (FIG. 5a), suggesting ROS act as a mediator in the 'LTB$_4$-BLT2' signaling leading to asthmatic symptoms. Administration of antisense BLT2 suppressed the level of LTB$_4$ in BAL fluid by ~72% (FIG. 5b), suggesting there may be cross-talk between LTB$_4$ and BLT2, such that each affects the other. Indeed, similar instances of crosstalk between eicosanoid lipid ligands and their receptors have been described previously (30, 31).

Result 5: Attenuation of NF-κB Activation by BLT2 Inhibition

ROS were previously reported to affect redox-sensitive factors such as NF-κB and AP-1 (32). To investigate the downstream signaling mechanism by which 'LTB$_4$-BLT2' causes asthmatic symptoms in vivo, EMSA was used to assess NF-κB activation in the lungs of OVA-challenged mice. Nuclear extracts from lung tissue were tested for their ability to bind a 32P-labeled oligonucleotide corresponding to the NF-κB consensus sequence. OVA challenge elicited an increase in NF-κB binding activity, which was attenuated by prior administration of antisense BLT2 (FIG. 6a). Moreover, competition assays using excess unlabeled oligonucleotide (cold) confirmed that the binding was specific. NF-κB normally resides in the cytoplasm in an inactivated form complexed with 1κB-α. Upon stimulation, 1κB-α is rapidly phosphorylated and degraded, allowing NF-κB to translocate into the nucleus. As a further indication of NF-κB activation, the level of IκB-α following BLT2 inhibition was analyzed. Substantial degradation of IκB-α following OVA challenge was detected, but antisense BLT2 (FIG. 6b) or LY255283 (FIG. 6d) reduced that degradation by ~50%. It is known that activation of NF-κB induces a variety of inflammatory genes, including adhesion molecules (e.g., VCAM-1) (33). Therefore the effect of BLT2 blockade on levels of VCAM-1, which is regulated by NF-κB and is reportedly involved in eosinophil infiltration (34), was also examined. As shown in FIGS. 6c and 6e, OVA challenge caused induction of VCAM-1 in lung tissue, and antisense BLT2 or LY255283 suppressed this effect by ~60%.

Result 6: Enhanced Expression of BLT2 in Samples from Clinically Asthmatic Subjects Immunohistochemical analysis was used to determine whether BLT2 levels are also elevated in human asthmatic subjects. Bronchial biopsy specimens were obtained from nonasthmatic controls (n=4) and patients with mild (n=4) or moderate (n=5) bronchial asthma. In accordance with the results obtained with the murine model of asthma (FIG. 1c), BLT2 expression was found to be significantly elevated in all mild and moderate bronchial asthma specimens (FIG. 7). Representative bronchial specimens from asthma patients (FIG. 7, panels D-F) show highly induced expression of BLT2, whereas those from healthy controls do not (FIG. 7, panels A-C), which indicates a role of BLT2 in the clinical pathogenesis of asthma. BLT2 expression was mainly elevated in the airway epithelial layers and microvascular endothelium in patient lung samples, which is similar to the pattern observed in the murine model of asthma.

Result 7: BLT2 Inhibition does not Interfere with Recruitment of T Lymphocytes into Airways BLT1 was found to be responsible for early recruitment of CD4+ and CD8+ T cells into the airways in a model of allergic pulmonary inflammation, suggesting that the LTB$_4$-BLT1 pathway is involved in linking early immune system activation and effector T cell recruitment (11). Thus, BLT2 might plays a similar role in T cell trafficking into airways. Significant numbers of CD4+ and CD8+ T cells were recruited into BAL fluid 12 hr after OVA challenge (FIGS. 8a and 8b). Importantly, antisense BLT2 had no inhibitory effect on T cell trafficking into airways, while injection of antisense BLT1 markedly diminished this recruitment of CD4+ and CD8+ T cells by ~93% and ~95%, respectively. This suggests that the actions mediated by 'LTB$_4$-BLT2' are quite distinct from those mediated by 'LTB$_4$-BLTT' during the asthmatic response.

Result 8: Antisense Rac Inhibit Airway Inflammation

To examine the involvement of Rac in OVA-induced allergic inflammatory responses, the activation of Rac by OVA provocation in lung lysate was examined. It is well known that Rac translocates to the membrane from the cytosol when it is activated. Therefore, the membrane proteins from the lung tissues of OVA challenged mice was prepared, and the amount of Rac in the membrane fraction as a marker of Rac activation was compared. Rac was activated by OVA provocation in early time point (1 to 3 hr) and returned to normal at 6 hr after provocation (FIG. 10a).

Because there is no specific inhibitor for Rac, antisense Rac oligonucleotide was designed analogous to the 5' end of murine Rac mRNA sequence, which spans the translation initiation site, to inhibit the endogenous expression of Rac. To confirm the effect of antisense Rac oligonucleotides on the expression of endogenous Rac, the oligonucleotides were injected into the tail veins of the mice, which were sacrificed after 12 hr. As expected, antisense Rac oligonucleotide inhibited the endogenous expression of Rac, while the control oligonucleotide didn't show significant effect on the expression of Rac in the lung tissues of the mice (FIG. 10b).

To assess the possible mediatory role of Rac in asthmatic airway inflammation, a specific Rac antisense, was administrated intravenously 24 hr and 1 hr before the 10% OVA challenge, and the mice were then sacrificed 48 hr after challenge. Histological analysis of the infiltration of inflammatory cells into the lung revealed increased airway obstruction and leukocyte infiltration following OVA challenge (FIG. 9a); again, Rac antisense diminished the effect.

Nuclear extracts from lung tissue were tested for their ability to bind a $^{32}$P-labeled oligonucleotide corresponding to the NF-κB consensus sequence. OVA challenge elicited an increase in NF-κB binding activity, which was attenuated by prior administration of antisense Rac (FIG. 9b). Moreover, competition assays using excess unlabeled oligonucleotide (cold) confirmed that the binding was specific.

It is known that activation of NF-κB induces a variety of inflammatory genes, including adhesion molecules (e.g., VCAM-1) (33). Therefore the effect of Rac blockade on levels of VCAM-1, which is regulated by NF-κB and is reportedly involved in eosinophil infiltration (34), was also examined. As shown in FIG. 8C, OVA challenge caused induction of VCAM-1 in lung tissue, and antisense Rac suppressed this effect (FIG. 9c).

Result 9: BLT2 Antisense Oligonucleotide Suppression Effect on BLT2 Expression

Suppressed BLT2 expression level was determined by RT-PCR. Rat2-BI_T2 stable cells were plated at a density of $5 \times 10^4$ cells/plate on 6 well plates. After 24 hr, cells were transiently transfected with BLT2 specific antisense and sense oligonucleotide plasmid with Lipofectamin reagent and then incubated in fresh DMEM supplemented with 10% FBS for an additional 24 h. After additional incubation, the transfected cells were harvested for BLT2 transcripts analysis. Total RNA was reverse-transcribed and PCR amplify were performed with BLT2 forward primer: 5'-tctcatcgggcatcacaggt-3' (SEQ ID NO: 23) and reverse primer: 5'-ccaagctccacaccacgaag-3' (SEQ ID NO: 24). Non-transfected Rat2-BLT2 stable cells cDNA was used the negative control and GAPDH was shown as internal control. FIG. 9 shows the suppression effect of BLT2 antisense oligonucleotide on BLT2 expression level by RT-PCR. The result showed that the level of BLT2 mRNA was reduced by the antisense oligonucleotide, however the level of BLT2 mRNA was not affected by the sense oligonucleotide.

Result 10: BLT2 siRNA Suppression Effect on BLT2 Expression

BLT2 siRNA expression effect on BLT2 expression was addressed by Northern blotting. CHO-BLT2 stable cells were plated at a density of $1 \times 10^5$ cells/plate on 60-mm dish. After 24 hr, cells were transiently transfected with BLT2 specific siRNA, targeting for 1705-1724 bp in NM_019839; 5'-GAAGGATGTCGGTCTGCTA-3' (SEQ ID NO: 25), with oligofectamin reagent and then incubated in fresh RPMI 1640 supplemented with 10% FBS for an additional 24 h. after additional incubation, total RNA was performed Northern blot with [$^{32}$P]-dCTP labeled BLT2 probe. Scramble RNA and non-coding sequence BLT2 siRNA were used the negative control. A 110 bp PCR fragment was amplified with pcDNA3.1-BLT2 clone using the following two primers, forward primer: 5'-cttctcatcgggcatcacag-3' (SEQ ID NO: 26) and reverse primer: 5'-atccttctgggcctacaggt-3' (SEQ ID NO: 27). This probe was located mainly in the BLT2 coding region. Total RNA was extracted with TRIzol reagent and then loaded the ten microgram total RNA for 2 hr in MOPS containing agarose gel. After this step, the total RNA was transferred the Hybond N$^+$ membrane for overnight with 20×SSC buffer. The membrane was hybridized with [$^{32}$P]-dCTP labeled BLT2 probe in the hybridization buffer for 18 h at 68° C. And then, washed in 0.1×SSC (0.1% SDS) for 1 h at 68° C. and subjected to autoradiography. FIG. 10 shows the suppression effect of BLT2 siRNA on BLT2 expression level by Northern blot. The result showed that the level of BLT2 mRNA was reduced by the BLT2 siRNA (coding sequence), however the level of BLT2 mRNA was not affected by the BLT2 siRNA (non-coding sequence).

As disclosed above, the present inventors investigated the role of BLT2 in the pathogenesis of asthma using a murine model and demonstrated that BLT2 plays a critical role in the development of AHR and airway inflammation by employing BLT2 inhibitors, such as antisense oligonucleotide. Therefore, the BLT 2 inhibitors according to the present invention can be effectively used as a therapeutic composition for treating asthma.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

Example 11

Long Form BLT2 is Involved in Chemotactic Signaling, Chemotactic Motility, Cell Growth, ERK Activation, and Release of Th2 Cytokine IL-13

To investigate the roles of long form BLT2 (LF-BLT2) and short form BLT2 (SF-BLT2), experiments were performed to examine their properties. In CHO cells transfected with LF-BLT2 and SF-BLT2 expression constructs (2 μg DNA), levels of mRNA expression were similar as determined by RT-PCR assay using GAPDH transcript levels as a control (FIG. 12a). The RT-PCR was performed under the following conditions: BLT2: lab primer (melting temperature 69° C.) for 30 cycles and GAPDH (melting temperature 58° C.) for 22 cycles. Additionally, FACS analysis of the CHO cells transfected with LF-BLT2 and SF-BLT2 expression constructs indicated similar levels of protein expression (FIG. 12b). FACS analysis was performed under the using non-permeabilization, anti-HA antibody (Roche), and anti-mouse FITC antibody.

CHO cells transfected with LF-BLT2 and SF-BLT2 expression constructs were examined for reactive oxygen species (ROS) generation and chemotactic motility in the presence of $LTB_4$. LF-BLT2 showed a significantly enhanced ROS generation in the presence of $LTB_4$ compared to SF-BLT2 (~25% more ROS generation; FIG. 13a). LF-BLT2 also showed a significantly enhanced chemotactic migration in the presence of $LTB_4$ compared to SF-BLT2 (~30% more chemotactic mobility; FIG. 13b). Thus, LF-BLT2 was observed to be more active or efficient than SF-BLT2 in mediating chemotactic signaling and motility. Rat-2 cells transfected with LF-BLT2 and SF-BLT2 were examined for growth and proliferation and ERK activity in the presence of $LTB_4$. SF-BLT2 transfected cells showed about the same growth as LF-BLT2 transfected cells, but, in the presence of $LTB_4$, significantly enhanced growth was observed by LF-BLT2 compared to SF-BLT2 (FIG. 14a). SF-BLT2 transfected cells showed about the same ERK activity as LF-BLT2, but, in the presence of $LTB_4$, a significantly enhanced ERK activation was observed by LF-BLT2 compared to SF-BLT2 (FIG. 14b).

To examine the roles of long form BLT2 (LF-BLT2) and short form BLT2 (SF-BLT2) in asthma, LF-BLT2 and SF-BLT2 expression constructs were transfected into bone marrow-derived mast cells (BMMCs), which are involved in the asthmatic allergic response. LF-BLT2 and SF-BLT2 nucleic acid sequences were inserted into the pcDNA3.1-LF-BLT2 plasmid. BMMC were transiently transfected with pcDNA3, pcDNA3-short form BLT2 or pcDNA3-long form BLT2 for 24 hr, and allowed to overexpress LF-BLT2 and SF-BLT2. BMMC were transfected using a MP-100 Microporator (Digital Bio, Seoul, Korea) according to the manufacturer's instructions. Briefly, $1 \times 10^6$ cells in 100 µl of resuspension buffer (Digital Bio) containing pcDNA3, pcDNA3-short form BLT2 or pcDNA3-long form BLT2 were electroporated using one pulse of 1,400 V for 30 ms. Cells were cultured in complete medium without antibiotics for 48 h, and the mRNA level of BLT2 was then analyzed by RT-PCR. For cells exposed to $LTB_4$, cells were incubated with 300 nM of $LTB_4$ for 1 hr and then harvested for detection of IL-13 transcripts by semi-quantitative RT-PCR with specific primers. The data show that expression of IL-13, a critical asthma-associated Th2 cytokine, was highly induced by transient transfection with long form BLT2-expression plasmid, and not by short form BLT2 plasmid in the presence of $LTB_4$ (FIG. 15) The $LTB_4$-evoked IL-13 induction in mast cells indicated that LF-BLT2 acted in an allergic response. Thus, in an asthmatic role, long form BLT2 demonstrated a distinguishable function from short form BLT2 in BMMCs.

Example 12

Generation of Anti-Long Form BLT2 Antibody Having BLT2 Neutralizing Activity

To study long form BLT2, a long form BLT2 antibody was generated using a 14-mer peptide present on long form BLT2 (PTPERPLWRLPPTC; peptide Ab-1; N-terminal sequences 14-27 amino acid residues), and not short form BLT2. Mice were immunized intraperitoneally with peptide Ab-1 (PTPERPLWRLPPTC) conjugated with BSA (peptide 2.0; 100 µg/CFA/head). Mice were immunized every 3 weeks. Four days after the last booster, mice were sacrificed and spleen cells were collected.

Spleen cells were fused with SP2 cells (American Type Culture Collection) by using PEG 4000 (Boehringer) at a 1:1 ratio. The PEG mediated fusion were performed according to the procedures previously described by Harlow and Lane (Harlow, E.; Lane, D., Eds.; Antibodies, a laboratory manual; Cold Spring Harbor Laboratory: New York, 1988; pp 139-243). Fused cells were distributed over 96 well tissue culture plates at 2,000 cells per well in complete DMEM medium containing 100 µM hypoxanthine, 0.4 µM aminopterin, and 16 µM thymidine (HAT; Sigma). Medium was replaced weekly.

For the identification of antigen-reacting mAbs, ELISA-based screening was performed. Briefly, microtiter plates were coated at 4° C. overnight with 100 µl per well of peptide Ab-1 conjugated with BSA (peptide 2.0; 10 µg/ml) diluted in PBS. Plates were blocked with blocking buffer (PBS containing 1% BSA (Sigma) and 0.05% Tween 20 (Sigma)) for 1 hr at room temperature. Hybridoma supernatant (100 µl per well) was transferred into the ELISA plates. Binding reaction was carried out at room temperature for 2 h. Subsequently, plates were washed four times with washing buffer (PBS containing 0.05% Tween 20 (Sigma)), and 100 µl of HRP-conjugated goat anti-human Fab (Sigma) diluted 1:10,000 in binding buffer (PBS containing 1% BSA (Sigma)) was added, and reactions were carried out at room temperature for 1 hr. Finally, plates were washed four times, and 100 µl of TMB substrate (Kirkegaard & Perry Laboratories) per well was added. The absorbance was determined at 490 nm.

To analyze the level of BLT2 expression, 253J-BV bladder cancer cells were fixed with 3% paraformaldehyde and permeabilized with 0.1% Triton X-100 in PBS. After being blocked with 2% BSA for 30 min, cells were incubated with the primary BLT2 antibody. Cells were then washed 3 times with PBS and incubated with FITC-conjugated anti-rabbit IgG (Invitrogen, Carlsbad, Calif.). Cells (10,000 per sample) were then analyzed with a flow cytometer (FACSCalibur™) using Cell Quest software, as described previously. Data are expressed as the mean fluorescence intensity. The FACS results shown in FIG. 16a are representative of three independent experiments with similar results.

Of 22 potential candidates, FACS analysis indicated at least 6 LF-BLT2-recognizing positive antibodies were obtained (FIG. 16b). Positive antibodies included: BLT2-LF-38 (#9 in FIG. 16b), BLT2-LF-45 (#10 in FIG. 16b) BLT2-LF-62-5 (#19 in FIG. 16b), BLT2-LF-26-22 (#20 in FIG. 16b), BLT2-LF-20 (#21 in FIG. 16b), BLT2-LF-12-3 (#22 in FIG. 16b). In addition to using or characterizing the 6 positive antibodies, antibody BLT2-LF-13 (#4 in FIG. 16b) which did not recognize LF-BLT2 was used as a negative control.

To test whether anti-LF-BLT2 antibodies have selective inhibitory activity of BLT2 function and, thus, BLT2 neutralizing activity, the effect of anti-LF-BLT2 antibody on the chemotaxis property of stably expressing BLT2 CHO cells, BLT2 transiently transfected CHO cells, and BLT1 transiently transfected CHO cells was examined. BLT2 expressing cells were prepared and maintained in the media with 0.5 mg/mL G418. Transiently transfected CHO cells (CHO-vector, CHO-BLT1, and CHO-BLT2) were transfected with pcDNA3.1, pcDNA3.1-long form BLT2 or pcDNA3.1-BLT1 plasmid. Chemotactic motility was assayed using Transwell chambers with 6.5-mm-diameter polycarbonate filters (8-1 µm pore size, Corning Costar), as previously described. Briefly, the lower surfaces of the filters were coated with 10 µg/mL fibronectin in serum-free RPMI 1640 medium for 1 hr at 37° C. Dry, coated filters containing various amounts of $LTB_4$ were placed in the lower wells of the Transwell chambers, after which 100 µL of CHO cells stably expressing BLT2 or transiently expressing BLT1 and BLT2 in serum-free RPMI 1640 were loaded into the top wells, yielding a final concentration of $2.5 \times 10^4$ cells/mL. When assessing the effects of inhibitors, cells were pretreated with the respective inhibitor for 30 min before seeding. After incubation at 37° C. in 5% $CO_2$ for 3 hr, the filters were fixed for 3 min with methanol and stained for 10 min with hematoxylin and eosin. Chemotaxis was quantified by counting the cells on the lower side of the filter under an optical microscope (magnification, ×200). Six fields were counted in each assay; each sample was assayed in duplicate; and the assays were repeated twice.

Chemotactic migration was dramatically inhibited by anti-LF-BLT2 antibody (BLT2-LF-26-22; #20 in FIG. 16b) in both CHO-BLT2 stable cells and BLT2-transiently transfected CHO cells (FIG. 17a), but no inhibitory effect by control antibody (BLT2-LF-13) (#4 in FIG. 16b) was detected (FIG. 17b). However, BLT2 neutralizing antibody did not show any inhibitory effect on the chemotactic migration caused by BLT1 transfected CHO cells (FIG. 17c), indicating that the inhibitory effect of anti-LF-BLT2-#26-22 (#20 in FIG. 16b) was specific to BLT2. Thus, anti-LF-BLT2 antibody display neutralizing activity specific for BLT2.

Example 13

Anti-Asthma Activities of Anti-Long Form BLT2 Neutralizing Antibody

LF-BLT2 IgG Ab were tested to determine if they had anti-BLT2-neutralizing effect in a mouse model of asthma. Anti-LF-BLT2 antibodies showed specific inhibitory activities on the asthmatic AHR (airway hyperresponsiveness) phenotype asthma-induced mouse (induced by methacholine).

Female BALB/c mice and C57BL/6 mice (7 weeks old; 18-20 g) were obtained from ORIENT BIO Inc. (Seoungnam, Korea). BALB/c mice were sensitized on day 1 by i.p. injection of 20 g OVA emulsified in 2.5 mg of alum (Pierce, Rockford, Ill.), followed by an identical booster injection administered on day 14. On days 21, 22 and 23 after initial sensitization, the mice were challenged for 30 min with an aerosol of 1% OVA using an ultrasonic nebulizer. BLT2 IgM and IgG Ab (100 μg or 500 μg/mice) or control antibody (100 μg/mice) was administered intravenously 1 hr before 1% OVA challenge. Mice were killed on day 25 to assess asthmatic phenotypes. All experimental animals used in this study were treated according to guidelines approved by the Institutional Animal Care and Use Committee of Korea University.

AHR was measured in unrestrained, conscious mice 24 hr after the final OVA challenge, using a whole-body plethysmograph as previously described. Aerosolized methacholine in increasing concentrations (from 6.25 mg/ml-50 mg/ml) was nebulized through an inlet of the main chamber for 3 min. Readings were taken and averaged for 3 min after each nebulization, and the enhanced pause (Penh) was determined.

The effect of BLT2 inhibition on AHR in response to methacholine was examined in the OVA-challenged mice. OVA-challenged mice were pretreated with control antibody (100 μg/mice) and BLT2 IgG Ab (100 μg/mice, 500 μg/mice) 1 h before 1% OVA challenge and then analysis at 24 h after the last OVA challenge. For each sample, 5 mice were used. Treatment with BLT2 IgG Ab at both doses used (100 μg/mice, 500 μg/mice) decreased Penh in response to methacholine compared to treatment with control antibody (FIG. 18A). The Penh of mice treated with BLT2 IgG Ab was similar to that of normal mice.

BLT2 IgG Ab attenuated ROS generation (FIG. 18B). BALF was collected 48 hr after last OVA challenge. OVA-challenged mice were pretreated with control antibody (100 μg/mice), BLT2 IgG Ab (100 μg/mice, 500 μg/mice) 1 hr before 1% OVA challenge and then sacrificed at 48 h after the last OVA challenge. The cells present in the BALF were observed using a FACSCalibur™.

As disclosed above, the invention makes use of BLT2 inhibitors for (1) suppressing an allergic response (e.g., asthma), (2) suppressing immune responses of mast cells, (3) suppressing Th2 cytokine IL-13 release, and (4) suppressing one or more of eosinophil infiltration into lung airway, airway inflammation, and airway hyperresponsiveness. Also, this invention include (4) a novel strategy for screening BLT2 signaling inhibitors by measuring the cell growth of Rat2-BLT2 stable cells. Thus, the invention provides strategies for targeting BLT2 overexpression or over-activation for developing therapeutic compositions against asthma.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

All patents and publications mentioned in this specification are herein incorporated by reference to the same extent as if each independent patent and publication was specifically and individually indicated to be incorporated by reference.

REFERENCES

The following documents are cited herein.
1. Lewis R A., Austen K F, Soberman R J (1990) N Engl J Med 323:645-655.
2. Samuelsson B, Dahlen S E, Lindgren J A., Rouzer C A, Serhan C N (1987) Science 237:1171-1176.
3. Yokomizo T, Izumi T, Shimizu T (2001) Arch Biochem Biophys 385:231-241.
4. Serhan C N (1996) Nature 384:23-24.
5. Gaudreault E, Thompson C, Stankova J, Rola-Pleszczynski M (2005) J Immunol 174:3617-3625.
6. Lindsay M A, Perkins R S, Barnes P J, Giembycz M A (1998) J Immunol 160:4526-4534.
7. Woo C H, You H J, Cho S H, Eom Y W, Chun J S, Yoo Y J, Kim J H (2002) J Biol Chem 277:8572-8578.
8. Tager A M, Dufour J H, Goodarzi K, Bercury S D, von Andrian U H, Luster A D (2000) J Exp Med 192:439-446.
9. Silbaugh S A, Stengel P $W_5$ Williams G D, Herron D K, Gallagher P, Baker S R (1987) Am Rev Respir Dis 136: 930-934.

10. Goodarzi K, Goodarzi M, Tager A M, Luster A D, von Andrian U H (2003) Nat Immunol 4:965-973.
11. Tager A M, Bromley S K, Medoff B D, Islam S A, Bercury S D, Friedrich E B, Carafone A D, Gerszten R E, Luster A D (2003) Nat Immunol 4:982-990.
12. Ott V L, Cambier J C, Kappler J, Marrack P, Swanson B J (2003) Nat Immunol 4:974-981.
13. Gelfand E W, Dakhama A (2006) J Allergy Clin Immunol 117:577-582.
14. Taube C, Miyahara N, Ott V, Swanson B, Takeda K, Loader J, Shultz L D, Tager A M, Luster A D, Dakhama A, et al (2006) J Immunol 176:3157-3164.
15. Islam S A, Thomas S Y, Hess C, Medoff B D, Means T K, Brander C, Lilly C M, Tager A M, Luster A D (2006) Blood 107:444-453.
16. Steiner D R, Gonzalez N C, Wood J G (2001) J Appl Physiol 91: 1160-1167.
17. Turner C R, Breslow R, Conklyn M J, Andresen C J, Patterson D K, Lopez-Anaya A, Owens B, Lee P, Watson J W, Showell H J (1996) J Clin Invest 97:381-367.
18. Montuschi P, Barnes P J (2002) J Allergy Clin Immunol 109:615-620.
19. Shindo K, Koide K, Fukumura M (1997) Thorax 52:1024-1029.
20. Henderson W R, Jr Lwis D B, Albert R K, Zhang Y, Lamm W J, Chiang G K, Jones F, Eriksen P, Tien Y T, Jonas M, et al (1996) J Exp Med 184:1483-1494.
21. Kamohara M, Takasaki J, Matsumoto M, Saito T, Ohishi T, Ishii H, Furuichi K (2000) J Biol Chem 275:27000-27004.
22. Yokomizo T, Izumi T, Chang K, Takuwa, Shimizu T (1997) Nature 387:620-624.
23. Yokomizo T, Kato K, Terawaki K, Izumi T, Shimizu T (2000) J Exp Med 192:421-432.
24. Qiu H, Johansson A S, Sjostrom M, Wan M, Schroder O, Palmblad J, Haeggstrom J Z (2006) Proc Natl Acad Sd USA 103:6913-6918.
25. Terawaki K, Yokomizo T, Nagase T, Toda A, Taniguchi M, Hashizume K, Yagi T, Shimizu T (2005) J Immunol 175: 4217-4225.
26. Miyahara N, Takeda K, Miyahara S, Taube C, Joetham A, Koya T, Matsubara S, Dakhama A, Tager A M, Luster A D, et al (2005) J Immunol 174:4979-4984.
27. Miyahara N, Takeda K, Miyahara S, Matsubara S, Koya T, Joetham A, Krishnan E, Dakhama A, Haribabu B, Gelfand E W (2005) Am J Respir Crit. Care Med 172:161-167.
28. Kanehiro A, Ikemura T, Makela M J, Lahn M, Joetham A, Dakhama A, Gelfand E W (2001) Am J Respir Crit. Care Med 163:173-184.
29. Cho S H, You H J, Woo C H, Yoo Y J, Kim J H (2004) J Immunol 173:624-631.
30. Lee Y C, Lee K S, Park S J, Park H S, Lim J S, Park K H, Im M J, Choi I W, Lee H K, Kim U H (2004) Faseb J 18:1917-1919.
31. Dohadwala M, Batra R K, Luo J, Lin Y, Krysan K, Pold M, Sharma S, Dubinett S M (2002) J Biol Chem 277:50828-50833.
32. Yoo M H, Song H, Woo C H, Kim H, Kim J H (2004) Oncogene 23:9259-9268.
33. Henderson W R, Jr Chi E Y, Teo J L, Nguyen C, Kahn M (2002) J Immunol 169:5294-5299.
34. Wilson S J, Wallin A, Della-Cioppa G, Sandstrom T, Holgate S T (2001) Am J Respir Crit. Care Med 164:1047-1052.
35. Huang W W, Garcia-Zepeda E A, Sauty A, Oettgen H C, Rothenberg M E, Luster A D (1998) J Exp Med 188:1063-1074.
36. Miyahara N, Miyahara S, Takeda K, Gelfand E W (2006) Allergol Int 55:91-97.
37. Woo C H, Lim J H, Kim J H (2005) Am J Physiol Lung Cell Mol Physiol 288:L307-L316.
38. Luster A D, Tager A M (2004) Nat Rev Immunol 4:711-724.
39. Boldogh I, Bacsi A, Choudhury B K, Dharajiya N, Alam R, Hazra T K, Mitra S, Goldblum R M, Sur S (2005) J Clin Invest 115:2169-2179.
40. Cortijo J, Marti-Cabrera M, de la Asuncion J Q Pallardo F V, Esteras A, Bruseghini L, Vina J, Morcillo E J (1999) Free Radio Biol Med 27:392-400.
41. MacNee W (2001) Eur J Pharmacol 429:195-207.
42. Dworski R (2000) Thorax 55 Suppl 2:S51-S53.
43. Lee S H, Seo M J, Choi S M, Sohn Y S, Kang K K, Ahn B O, Kwon J W, Yoo M (2005) Arch Pharm Res 28:1350-1357.
44. Barnes P J, Karin M (1997) N Engl J Med 336:1066-1071.
45. Hamilton L M, Davies D E, Wilson S J, Kimber I, Dearman R J, Holgatem S T (2001) Monaldi Arch Chest Dis 56:48-54.
46. Hart L A, Krishnan V L, Adcock I M, Barnes P J, Chung K F (1998) Am J Respir Crit. Care Med 158:1585-1592.
47. Shao W H, Del Prete A, Bock C B, Haribabu B (2006) J Immunol 176:6254-6261.

What is claimed is:

1. A method of treating asthma in a patient, the method comprising administering to the patient a therapeutically effective amount of an antibody or fragment thereof that specifically binds to and inhibits the expression or intracellular signaling of long-form BLT2.

2. The method of claim 1, wherein the agent selectively reduces the expression or intracellular signaling of long-form BLT2 to the patient while the expression or intracellular signaling of short-form BLT2 is not disrupted.

3. The method of claim 1, wherein the antibody or fragment thereof specifically binds long-form BLT-2 in the region set forth by amino acids 1-31 of SEQ ID NO: 3.

4. The method of claim 1, wherein the antibody or fragment thereof specifically binds long-form BLT-2 in the region set forth by amino acids 14-27 of SEQ ID NO: 3.

5. The method of claim 1, wherein the antibody is a polyclonal or monoclonal antibody.

6. The method of claim 1, wherein the expression or activity of an asthma-associated Th2 cytokine selected from the group consisting of IL-13 is reduced.

7. The method of claim 1, wherein one or more of eosinophil infiltration into lung airway, airway inflammation, or airway hyperresponsiveness (AHR) is reduced.

8. The method of claim 1, wherein the asthma is characterized by the overexpression of long-form BLT2 in the lung airway.

9. The method of claim 8, wherein long-form BLT2 activation increases ROS generation and NF-κB activation.

10. The method of claim 1, further comprising administering to the patient a therapeutically effective amount of an agent that inhibits the expression or activity of Rac.

* * * * *